(12) United States Patent
Davoren et al.

(10) Patent No.: US 8,822,494 B2
(45) Date of Patent: Sep. 2, 2014

(54) HETEROAROMATIC COMPOUNDS AND THEIR USE AS DOPAMINE D1 LIGANDS

(71) Applicant: Pfizer Inc., New York, NY (US)

(72) Inventors: Jennifer Elizabeth Davoren, Cambridge, MA (US); Amy Beth Dounay, Colorado Springs, CO (US); Ivan Viktorovich Efremov, Chestnut Hill, MA (US); David Lawrence Firman Gray, Groton, MA (US); Scot Richard Mente, Arlington, MA (US); Steven Victor O'Neil, East Lyme, CT (US); Bruce Nelsen Rogers, Belmont, MA (US); Chakrapani Subramanyam, South Glastonbury, CT (US); Lei Zhang, Auburndale, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/072,563

(22) Filed: Nov. 5, 2013

(65) Prior Publication Data
US 2014/0128374 A1    May 8, 2014

Related U.S. Application Data

(60) Provisional application No. 61/723,995, filed on Nov. 8, 2012.

(51) Int. Cl.
| C07D 401/04 | (2006.01) |
| C07D 401/14 | (2006.01) |
| A61K 31/437 | (2006.01) |

(52) U.S. Cl.
CPC ............ *C07D 401/04* (2013.01); *C07D 401/14* (2013.01); *A61K 31/437* (2013.01)
USPC ............ 514/300; 514/303; 546/113; 546/119

(58) Field of Classification Search
CPC ... C07D 401/14; C07D 401/04; A61K 31/437
USPC ............................ 546/113, 119; 514/300, 303
See application file for complete search history.

(56) References Cited

U.S. PATENT DOCUMENTS

| 2008/0194557 A1 | 8/2008 | Barbosa et al. |
| 2008/0200458 A1 | 8/2008 | Barbosa et al. |
| 2010/0317646 A1* | 12/2010 | Mciver et al. ............ 514/210.18 |
| 2013/0267513 A1 | 10/2013 | Chan et al. |

FOREIGN PATENT DOCUMENTS

| WO | 91/11172 | 8/1991 |
| WO | 94/02518 | 2/1994 |
| WO | 98/55148 | 12/1998 |
| WO | 00/35298 | 6/2000 |
| WO | 2004/113303 | 12/2004 |
| WO | 2006/077401 | 7/2006 |
| WO | 2010/106333 | 9/2010 |
| WO | 2014072881 | 5/2014 |

OTHER PUBLICATIONS

Almarsson and M. J. Zaworotko, Chem. Commun. 2004, 17, 1889-1896.
Bringmann, G. et al., Atroposelective Synthesis of Axially Chiral Biaryl Compounds. Angew. Chem., Int. Ed. 2005, 44, 5384-5427.
Erdik, Tetrahedron 1992, 48, 9577-9648.
Finnin and Morgan, J. Pharm. Sci. 1999, 88, 955-958.
Freedman, T. B. et al., Absolute Configuration Determination of Chiral Molecules in the Solution State Using Vibrational Circular Dichroism. Chirality 2003, 15, 743-758.
Goldman-Rakic PS et al., "Targeting the dopamine D1 receptor in schizophrenia: insights for cognitive dysfunction", Psychopharmacology 174(1):3-16 (2004).
Goulet M, Madras BK "D(1) dopamine receptor agonists are more effective in alleviating advanced than mild parkinsonism in 1-methyl-4-phenyl-1,2,3,6-tetrahydropyridine-treated monkeys", Journal of Pharmacology and Experimental Therapy 292(2):714-24 (2000).
Haleblian, J. Pharm. Sci. 1975, 64, 1269-1288.
Harris et al., Tetrahedron 2011, 67, 9063-9066.
Kalaitzakis et al., Tetrahedron: Asymmetry 2007, 18, 2418-2426.
Liang and Chen, Expert Opinion in Therapeutic Patents 2001, 11, 981-986.
Littke et al., J. Am. Chem. Soc. 2000, 122, 4020-4028.
Missale C, Nash SR, Robinson SW, Jaber M, Caron MG "Dopamine receptors: from structure to function", Physiological Reviews 78:189-225 (1998).
Miyaura and A. Suzuki, Chem. Rev. 1995, 95, 2457-2483.
Ryman-Rasmussen et al., "Differential activation of adenylate cyclase and receptor internalization by novel dopamine D1 receptor agonists", Molecular Pharmacology 68(4):1039-1048 (2005).
Surmeier DJ et al., "The role of dopamine in modulating the structure and function of striatal circuits", Prog. Brain Res. 183:149-67 (2010).
Suzuki, J. Organomet. Chem. 1999, 576, 147-168.
Verma et al., Pharmaceutical Technology On-line, 25(2), 1-14 (2001).
Search Report and Written Opinion of PCT/IB2013/059768.

* cited by examiner

*Primary Examiner* — Niloofar Rahmani
(74) *Attorney, Agent, or Firm* — Feng Shao

(57) ABSTRACT

The present invention provides, in part, compounds of Formula I:

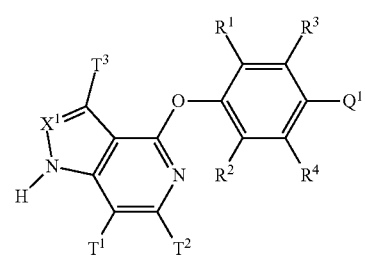

and pharmaceutically acceptable salts thereof and N-oxides of the foregoing; processes for the preparation of; intermediates used in the preparation of; and compositions containing such compounds, salts or N-oxides, and their uses for treating D1-mediated (or D1-associated) disorders including, e.g., schizophrenia (e.g., its cognitive and negative symptoms), cognitive impairment (e.g., cognitive impairment associated with schizophrenia, AD, PD, or pharmacotherapy therapy), ADHD, impulsivity, compulsive gambling, overeating, autism spectrum disorder, MCI, age-related cognitive decline, dementia, RLS, Parkinson's disease, Huntington's chorea, anxiety, depression, MDD, TRD, and bipolar disorder.

54 Claims, No Drawings

HETEROAROMATIC COMPOUNDS AND THEIR USE AS DOPAMINE D1 LIGANDS

This application claims the benefit of priority to U.S. provisional patent application Ser. No. 61/723,995 filed Nov. 8, 2012, the disclosure of which is hereby incorporated by reference in its entirety.

FIELD OF THE INVENTION

The present invention generally relates to heteroaromatic compounds, which are dopamine D1 ligands, for example dopamine D1 agonists or partial agonists.

BACKGROUND OF THE INVENTION

Dopamine acts upon neurons through two families of dopamine receptors, D1-like receptors (D1Rs) and D2-like receptors (D2Rs). The D1-like receptor family consists of D1 and D5 receptors which are expressed in many regions of the brain. D1 mRNA has been found, for example, in the striatum and nucleus accumbens. See e.g., Missale C, Nash S R, Robinson S W, Jaber M, Caron M G "Dopamine receptors: from structure to function", *Physiological Reviews* 78:189-225 (1998). Pharmacological studies have reported that D1 and D5 receptors (D1/D5), namely D1-like receptors, are linked to stimulation of adenylyl cyclase, whereas D2, D3, and D4 receptors, namely D2-like receptors, are linked to inhibition of cAMP production.

Dopamine D1 receptors are implicated in numerous neuropharmacological and neurobiological functions. For example, D1 receptors are involved in different types of memory function and synaptic plasticity. See e.g., Goldman-Rakic P S et al., "Targeting the dopamine D1 receptor in schizophrenia: insights for cognitive dysfunction", *Psychopharmacology* 174(1):3-16 (2004). Moreover, D1 receptors have been implicated in a variety of psychiatric, neurological, neurodevelopmental, neurodegenerative, mood, motivational, metabolic, cardiovascular, renal, ophthalmic, endocrine, and/or other disorders described herein including schizophrenia (e.g., cognitive and negative symptoms in schizophrenia), cognitive impairment associated with D2 antagonist therapy, ADHD, impulsivity, autism spectrum disorder, mild cognitive impairment (MCI), age-related cognitive decline, Alzheimer's dementia, Parkinson's disease (PD), Huntington's chorea, depression, anxiety, treatment-resistant depression (TRD), bipolar disorder, chronic apathy, anhedonia, chronic fatigue, post-traumatic stress disorder, seasonal affective disorder, social anxiety disorder, post-partum depression, serotonin syndrome, substance abuse and drug dependence, Tourette's syndrome, tardive dyskinesia, drowsiness, sexual dysfunction, migraine, systemic lupus erythematosus (SLE), hyperglycemia, dislipidemia, obesity, diabetes, sepsis, post-ischemic tubular necrosis, renal failure, resistant edema, narcolepsy, hypertension, congestive heart failure, postoperative ocular hypotonia, sleep disorders, pain, and other disorders in a mammal. See e.g., Goulet M, Madras B K "D(1) dopamine receptor agonists are more effective in alleviating advanced than mild parkinsonism in 1-methyl-4-phenyl-1,2,3,6-tetrahydropyridine-treated monkeys", *Journal of Pharmacology and Experimental Therapy* 292(2):714-24 (2000); Surmeier D J et al., "The role of dopamine in modulating the structure and function of striatal circuits", *Prog. Brain Res.* 183:149-67 (2010).

New or improved agents that modulate (such as agonize or partially agonize) D1 are needed for developing new and more effective pharmaceuticals to treat diseases or conditions associated with dysregulated activation of D1, such as those described herein.

SUMMARY OF THE INVENTION

The present invention provides, in part, a compound of Formula I:

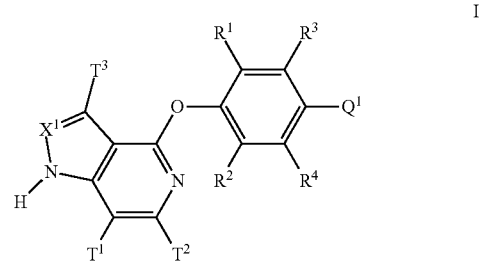

or a pharmaceutically acceptable salt thereof, wherein:
$X^1$ is N or $CT^4$;
$Q^1$ is an N-containing 5- to 6-membered heteroaryl or an N-containing 5- to 6-membered heterocycloalkyl, each optionally substituted with one $R^9$ and further optionally substituted with 1, 2, 3, or 4 $R^{10}$;
each of $T^1$, $T^2$, $T^3$, and $T^4$ is independently selected from the group consisting of H, halogen, —CN, $C_{1-4}$ alkyl, $C_{1-4}$ haloalkyl, cyclopropyl, fluorocyclopropyl, $C_{1-4}$ alkoxy, $C_{1-4}$ haloalkoxy, and —C(=O)—O—($C_{1-4}$ alkyl);
each of $R^1$ and $R^2$ is independently selected from the group consisting of H, halogen, —CN, $C_{1-6}$ alkyl, $C_{1-6}$ haloalkyl, $C_{1-6}$ alkoxy, $C_{1-6}$ haloalkoxy, $C_{3-6}$ cycloalkyl, —C(=O)OH, and —C(=O)—O—($C_{1-4}$ alkyl), wherein each of said $C_{1-6}$ alkyl and $C_{3-6}$ cycloalkyl is optionally substituted with 1, 2, 3, 4, or 5 substituents each independently selected from halo, —OH, —CN, $C_{1-4}$ alkyl, $C_{1-4}$ haloalkyl, $C_{1-4}$ alkoxy, and $C_{1-4}$ haloalkoxy;
each of $R^3$ and $R^4$ is independently selected from the group consisting of H, halogen, —OH, —$NO_2$, —CN, —$SF_5$, $C_{1-6}$ alkyl, $C_{1-6}$ haloalkyl, $C_{1-6}$ haloalkoxy, $C_{2-6}$ alkenyl, $C_{2-6}$ alkynyl, $C_{3-7}$ cycloalkyl, a 4- to 10-membered heterocycloalkyl, —$N(R^5)(R^6)$, —$N(R^7)(C(=O)R^8)$, —C(=O)—$N(R^5)(R^6)$, —C(=O)—$R^8$, —C(=O)—$OR^8$, —$N(R^7)(S(=O)_2R^8)$, —$S(=O)_2$—$N(R^5)(R^6)$, —$SR^8$, and —$OR^8$, wherein each of said $C_{1-6}$ alkyl, $C_{3-7}$ cycloalkyl, and heterocycloalkyl is optionally substituted with 1, 2, or 3 substituents each independently selected from the group consisting of halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, —$N(R^5)(R^6)$, —$N(R^7)(C(=O)R^8)$, —C(=O)—$OR^8$, —C(=O)H, —C(=O)$R^8$, —C(=O)$N(R^5)(R^6)$, —$N(R^7)(S(=O)_2R^8)$, —$S(=O)_2$—$N(R^5)(R^6)$, —$SR^8$, and —$OR^8$;
$R^5$ is H, $C_{1-4}$ alkyl, $C_{1-4}$ haloalkyl, or $C_{3-7}$ cycloalkyl;
$R^6$ is H or selected from the group consisting of $C_{1-4}$ alkyl, $C_{1-4}$ haloalkyl, $C_{3-7}$ cycloalkyl, a 4- to 10-membered heterocycloalkyl, $C_{6-10}$ aryl, a 5- to 10-membered heteroaryl, $C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl-, wherein each of the selections from the group is optionally substituted with 1, 2, 3, or 4 substituents each independently selected from the group consisting of —OH, —CN, $C_{1-4}$ alkyl, $C_{3-7}$ cycloalkyl, $C_{1-4}$ hydroxylalkyl, —S—$C_{1-4}$ alkyl, —C(=O)H, —C(=O)—$C_{1-4}$ alkyl, —C(=O)—O—$C_{1-4}$ alkyl, —C(=O)—NH$_2$, —C(=O)—N(C$_{1-4}$ alkyl)$_2$, C$_{1-4}$ haloalkyl, C$_{1-4}$ alkoxy, and C$_{1-4}$ haloalkoxy;

or R$^5$ and R$^6$ together with the N atom to which they are attached form a 4- to 10-membered heterocycloalkyl or a 5- to 10-membered heteroaryl, each optionally substituted with 1, 2, 3, 4, or 5 substituents each independently selected from the group consisting of halogen, —OH, oxo, —C(=O)H, —C(=O)OH, —C(=O)—C$_{1-4}$ alkyl, —C(=O)—NH$_2$, —C(=O)—N(C$_{1-4}$ alkyl)$_2$, —CN, C$_{1-4}$ alkyl, C$_{1-4}$ alkoxy, C$_{1-4}$ hydroxylalkyl, C$_{1-4}$ haloalkyl, and C$_{1-4}$ haloalkoxy;

R$^7$ is selected from the group consisting of H, C$_{1-4}$ alkyl, and C$_{3-7}$ cycloalkyl;

R$^8$ is selected from the group consisting of C$_{1-6}$ alkyl, C$_{3-7}$ cycloalkyl, a 4- to 14-membered heterocycloalkyl, C$_{6-10}$ aryl, a 5- to 10-membered heteroaryl, (C$_{3-7}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl-, wherein each of the selections from the group is optionally substituted with 1, 2, or 3 substituents each independently selected from the group consisting of halogen, —CF$_3$, —CN, —OH, oxo, —S—C$_{1-4}$ alkyl, C$_{1-4}$ alkyl, C$_{1-4}$ haloalkyl, C$_{2-6}$ alkenyl, C$_{2-6}$ alkynyl, C$_{3-7}$ cycloalkyl, C$_{1-4}$ alkoxy, and C$_{1-4}$ haloalkoxy;

R$^9$ is C$_{1-4}$ alkyl, C$_{1-4}$ haloalkyl, —CN, —SF$_5$, —N(R$^5$)(R$^6$), C$_{1-6}$ alkoxy, C$_{1-6}$ haloalkoxy, C$_{3-7}$ cycloalkyl, or C$_{3-7}$ cycloalkyl, wherein each of the C$_{1-4}$ alkyl and C$_{3-7}$ cycloalkyl is optionally substituted with 1, 2, 3, 4, or 5 substituents each independently selected from the group consisting of halogen, —N(R$^5$)(R$^6$), C$_{1-4}$ alkyl, C$_{1-4}$ haloalkyl, C$_{3-7}$ cycloalkyl, C$_{1-4}$ alkoxy, and C$_{1-4}$ haloalkoxy;

each R$^{10}$ is independently selected from the group consisting of halogen, —OH, —CN, —SF$_5$, —NO$_2$, oxo, thiono ("=S"), C$_{1-6}$ alkyl, C$_{1-6}$ haloalkyl, C$_{1-6}$ hydroxylalkyl, C$_{1-6}$ alkoxy, C$_{1-6}$ haloalkoxy, C$_{3-7}$ cycloalkyl, C$_{2-6}$ alkenyl, C$_{2-6}$ alkynyl, C$_{6-10}$ aryl, a 4- to 10-membered heterocycloalkyl, a 5- to 10-membered heteroaryl, (C$_{3-7}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, (5- to 10-membered heteroaryl)-C$_{1-4}$ alkyl-, —N(R$^5$)(R$^6$), —N(R$^7$)(C(=O)R$^8$), —S(=O)$_2$N(R$^5$)(R$^6$), —C(=O)—N(R$^5$)(R$^6$), —C(=O)—R$^8$, —C(=O)—OR$^8$, —SR$^8$, and —OR$^8$, wherein each of said C$_{1-6}$ alkyl, C$_{3-7}$ cycloalkyl, C$_{6-10}$ aryl, 4- to 10-membered heterocycloalkyl, 5- to 10-membered heteroaryl, (C$_{3-7}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl- is optionally substituted with 1, 2, 3, or 4 substituents each independently selected from the group consisting of halogen, OH, —CN, —NO$_2$, C$_{1-4}$ alkyl, C$_{1-4}$ hydroxylalkyl, C$_{1-4}$ alkoxy, —N(R$^5$)(R$^6$), —S—(C$_{1-4}$ alkyl), —S(=O)$_2$—(C$_{1-4}$ alkyl), C$_{6-10}$ aryloxy, [(C$_{6-10}$ aryl)-C$_{1-4}$ alkyloxy-optionally substituted with 1 or 2 C$_{1-4}$ alkyl], oxo, —C(=O)H, —C(=O)—C$_{1-4}$ alkyl, —C(=O)O—C$_{1-4}$ alkyl, —C(=O)NH$_2$, —NHC(=O)H, —NHC(=O)—(C$_{1-4}$ alkyl), C$_{3-7}$ cycloalkyl, a 5- or 6-membered heteroaryl, C$_{1-4}$ haloalkyl, and C$_{1-4}$ haloalkoxy;

or R$^9$ and an adjacent R$^{10}$ together with the two ring atoms on Q$^1$ to which they are attached form a fused benzene ring or a fused 5- or 6-membered heteroaryl, each optionally substituted with 1, 2, 3, 4, or 5 independently selected R$^{10a}$; and each R$^{10a}$ is independently from the group consisting of halogen, —OH, —N(R$^5$)(R$^6$), —C(=O)OH, —C(=O)—C$_{1-4}$ alkyl, —C(=O)—NH$_2$, —C(=O)—N(C$_{1-4}$ alkyl)$_2$, —CN, —SF$_5$, C$_{1-4}$ alkyl, C$_{1-4}$ alkoxy, C$_{1-4}$ hydroxylalkyl, C$_{1-4}$ haloalkyl, and C$_{1-4}$ haloalkoxy;

provided that the compound of Formula I is not 4-(4-imidazol-1-yl-phenoxy)-3-methyl-1H-pyrazolo[4,3-c]pyridine.

The present invention also provides a composition (e.g., a pharmaceutical composition) comprising a compound of Formula I (including an N-oxide thereof or a pharmaceutically acceptable salt of the compound or the N-oxide).

Compounds of Formula I (including N-oxides thereof and pharmaceutically acceptable salts of the compounds or the N-oxides) are D1 modulators (e.g., D1 agonists or partial agonists). According, the present invention further provides a method for treating a D1-mediated (or D1-associated) disorder (e.g., cognitive impairment such as cognitive impairment associated with schizophrenia or cognitive impairment associated with Alzheimer's disease; schizophrenia; Alzheimer's disease; or Parkinson's disease), comprising administering to a mammal (e.g., a human) in need thereof an amount of a compound of Formula I (including a pharmaceutically acceptable salt thereof or an N-oxide of the compound or salt) effective in modulating (e.g., agonizing or partially agonizing) D1.

As used herein, the term "adjacent" in describing the relative positions of two substituent groups on a ring structure refers to two substituent groups that are respectively attached to two ring-forming atoms of the same ring, wherein the two ring-forming atoms are directly connected through a chemical bond. For example, in each of the following structures:

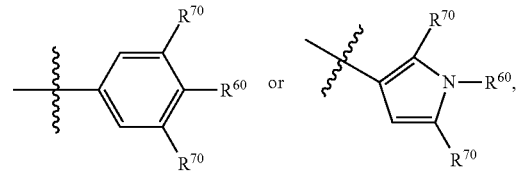

either of the two R$^{70}$ groups is an adjacent group of R$^{60}$.

As used herein, the term "n-membered" where n is an integer typically describes the number of ring-forming atoms in a moiety where the number of ring-forming atoms is n. For example, pyridine is an example of a 6-membered heteroaryl ring and thiophene is an example of a 5-membered heteroaryl group.

At various places in the present specification, substituents of compounds of the invention are disclosed in groups or in ranges. It is specifically intended that the invention include each and every individual subcombination of the members of such groups and ranges. For example, the term "C$_{1-6}$ alkyl" is specifically intended to include C$_1$ alkyl(methyl), C$_2$ alkyl (ethyl), C$_3$ alkyl, C$_4$ alkyl, C$_5$ alkyl, and C$_6$ alkyl. For another example, the term "a 5- to 10-membered heteroaryl group" is specifically intended to include any 5-, 6-, 7-, 8-, 9- or 10-membered heteroaryl group.

As used herein, the term "alkyl" is defined to include saturated aliphatic hydrocarbons including straight chains and branched chains. In some embodiments, the alkyl group has 1 to 6, e.g., 1 to 4, carbon atoms. For example, as used herein, the term "C$_{1-6}$ alkyl," as well as the alkyl moieties of other groups referred to herein (e.g., C$_{1-6}$alkoxy) refers to linear or branched radicals of 1 to 6 carbon atoms (e.g., methyl, ethyl, n-propyl, isopropyl, n-butyl, isobutyl, sec-butyl, tert-butyl, n-pentyl, or n-hexyl), optionally substituted by 1 or more (such as 1 to 5) suitable substituents. The term "C$_{1-4}$ alkyl" refers to linear or branched aliphatic hydrocarbon chains of 1 to 4 carbon atoms (i.e., methyl, ethyl, n-propyl, isopropyl, n-butyl, isobutyl, sec-butyl, tert-butyl). The term "C$_{1-3}$ alkyl" refers to linear or branched aliphatic hydrocarbon chains of 1 to 3 carbon atoms As used herein, the term "alkenyl" refers to aliphatic hydrocarbons having at least one carbon-carbon double bond, including straight chains and branched chains having at least one carbon-carbon double bond. In some embodiments, the alkenyl group has 2 to 6 carbon atoms. In some embodiments, the alkenyl group has 2 to 4 carbon atoms. For example, as used herein, the term "$C_{2-6}$ alkenyl" means straight or branched chain unsaturated radicals of 2 to 6 carbon atoms, including, but not limited to, ethenyl, 1-propenyl, 2-propenyl (allyl), isopropenyl, 2-methyl-1-propenyl, 1-butenyl, 2-butenyl, and the like, optionally substituted by 1 to 5 suitable substituents. When the compounds of Formula I contain an alkenyl group, the alkenyl group may exist as the pure E form, the pure Z form, or any mixture thereof.

As used herein, the term "alkynyl" refers to aliphatic hydrocarbons having at least one carbon-carbon triple bond, including straight chains and branched chains having at least one carbon-carbon triple bond. In some embodiments, the alkynyl group has 2 to 6 carbon atoms. For example, as used herein, the term "$C_{2-6}$ alkynyl" is used herein to mean straight or branched hydrocarbon chain alkynyl radicals as defined above, having 2 to 6 carbon atoms and one triple bond, optionally substituted by 1 or more (such as 1 to 5) suitable substituents.

As used herein, the term "cycloalkyl" refers to saturated or unsaturated, non-aromatic, monocyclic or polycyclic (such as bicyclic) hydrocarbon rings (e.g., monocyclics such as cyclopropyl, cyclobutyl, cyclopentyl, cyclohexyl, cycloheptyl, cyclooctyl, cyclononyl, or bicyclics including spiro, fused, or bridged systems (such as bicyclo[1.1.1]pentanyl, bicyclo[2.2.1]heptanyl, bicyclo[3.2.1]octanyl or bicyclo[5.2.0]nonanyl, decahydronaphthalenyl, etc.), optionally substituted by 1 or more (such as 1 to 5) suitable substituents. The cycloalkyl group has 3 to 15 carbon atoms. In some embodiments the cycloalkyl may optionally contain one, two or more non-cumulative non-aromatic double or triple bonds and/or one to three oxo groups. In some embodiments, the bicycloalkyl group has 6 to 15 carbon atoms. For example, the term "$C_{3-7}$ cycloalkyl" refers to saturated or unsaturated, non-aromatic, monocyclic or polycyclic (such as bicyclic) hydrocarbon rings of 3 to 7 ring-forming carbon atoms (e.g., cyclopropyl, cyclobutyl, cyclopentyl, cyclohexyl, or bicyclo[1.1.1]pentanyl). For another example, the term "$C_{3-6}$ cycloalkyl" refers to saturated or unsaturated, non-aromatic, monocyclic or polycyclic (such as bicyclic) hydrocarbon rings of 3 to 6 ring-forming carbon atoms. For yet another example, the term "$C_{3-4}$ cycloalkyl" refers to cyclopropyl or cyclobutyl. Also included in the definition of cycloalkyl are moieties that have one or more aromatic rings (including aryl and heteroaryl) fused to the cycloalkyl ring, for example, benzo or thienyl derivatives of cyclopentane, cyclopentene, cyclohexane, and the like (e.g., 2,3-dihydro-1H-indene-1-yl, or 1H-inden-2(3H)-one-1-yl). The cycloalkyl group is optionally substituted by 1 or more (such as 1 to 5) suitable substituents.

As used herein, the term "aryl" refers to all-carbon monocyclic or fused-ring polycyclic aromatic groups having a conjugated pi-electron system. The aryl group has 6 or 10 carbon atoms in the ring(s). Most commonly, the aryl group has 6 carbon atoms in the ring. For example, as used herein, the term "$C_{6-10}$ aryl" means aromatic radicals containing from 6 to 10 carbon atoms such as phenyl or naphthyl. The aryl group is optionally substituted by 1 or more (such as 1 to 5) suitable substituents.

As used herein, the term "heteroaryl" refers to monocyclic or fused-ring polycyclic aromatic heterocyclic groups with one or more heteroatom ring members (ring-forming atoms) each independently selected from O, S and N in at least one ring. The heteroaryl group has 5 to 14 ring-forming atoms, including 1 to 13 carbon atoms, and 1 to 8 heteroatoms selected from O, S, and N. In some embodiments, the heteroaryl group has 5 to 10 ring-forming atoms including one to four heteroatoms. The heteroaryl group can also contain one to three oxo or thiono groups. In some embodiments, the heteroaryl group has 5 to 8 ring-forming atoms including one, two or three heteroatoms. Examples of monocyclic heteroaryls include those with 5 ring-forming atoms including one to three heteroatoms or those with 6 ring-forming atoms including one, two or three nitrogen heteroatoms. Examples of fused bicyclic heteroaryls include two fused 5- and/or 6-membered monocyclic rings including one to four heteroatoms.

Examples of heteroaryl groups include pyridinyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, 1H-imidazo[4,5-c]pyridinyl, imidazo[1,2-a]pyridinyl, 1H-pyrrolo[3,2-c]pyridinyl, imidazo[1,2-a]pyrazinyl, imidazo[2,1-c][1,2,4]triazinyl, imidazo[1,5-a]pyrazinyl, imidazo[1,2-a]pyrimidinyl, 1H-indazolyl, 9H-purinyl, imidazo[1,2-a]pyrimidinyl, [1,2,4]triazolo[1,5-a]pyrimidinyl, [1,2,4]triazolo[4,3-b]pyridazinyl, isoxazolo[5,4-c]pyridazinyl, isoxazolo[3,4-c]pyridazinyl, pyridone, pyrimidone, pyrazinone, pyrimidinone, 1H-imidazol-2(3H)-one, 1H-pyrrole-2,5-dione, 3-oxo-2H-pyridazinyl, 1H-2-oxo-pyrimidinyl, 1H-2-oxo-pyridinyl, 2,4(1H,3H)-dioxo-pyrimidinyl, 1H-2-oxo-pyrazinyl, and the like. The heteroaryl group is optionally substituted by 1 or more (such as 1 to 5) suitable substituents.

As used herein, the term "N-containing" when used in connection with a heteroaryl or heterocycloalkyl means that the heteroaryl or heterocycloalkyl comprises at least one ring-forming nitrogen (N) atom and optionally one or more (e.g., 1, 2, 3, or 4) ring-forming heteroatoms each independently selected from O, S and N. The term "N-containing 5- to 10-membered heteroaryl" refers to a 5- to 10-membered heteroaryl group (including monocyclic or bicyclic systems) comprising at least one ring-forming nitrogen (N) atom and optionally one or more (e.g., 1, 2, 3, or 4) ring-forming heteroatoms each independently selected from O, S and N. The term "N-containing 5- or 6-membered heteroaryl" refers to a 5- or 6-membered heteroaryl group comprising at least one ring-forming nitrogen (N) atom and optionally one or more (e.g., 1, 2, 3, or 4) ring-forming heteroatoms each independently selected from O, S and N. Examples of N-containing 5- to 10-membered heteroaryl groups include pyridinyl, pyrazinyl, pyrimidinyl, pyridazinyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, 1H-imidazo[4,5-c]pyridinyl, imidazo[1,2-a]pyridinyl, 1H-pyrrolo[3,2-c]pyridinyl, imidazo[1,2-a]pyrazinyl, imidazo[2,1-c][1,2,4]triazinyl, imidazo[1,5-a]pyrazinyl, imidazo[1,2-a]pyrimidinyl, 1H-indazolyl, 9H-purinyl, imidazo[1,2-a]pyrimidinyl, [1,2,4]triazolo[1,5-a]pyrimidinyl, [1,2,4]triazolo[4,3-b]pyridazinyl, isoxazolo[5,4-c]pyridazinyl, isoxazolo[3,4-c]pyridazinyl, pyridone, pyrimidone, pyrazinone, pyrimidinone, 1H-imidazol-2(3H)-one, 1H-pyrrole-2,5-dione, 3-oxo-2H-pyridazinyl, 1H-2-oxo-pyrimidinyl (e.g., 1H-2-oxo-pyrimidin-6-yl), 1H-2-oxo-pyridinyl, 2,4(1H,3H)-dioxo-pyrimidinyl, 1H-2-oxo-pyrazinyl, and the like. Examples of N-containing 5- or 6-membered heteroaryl groups include pyridinyl, pyrazinyl, pyrimidinyl, pyridazinyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), 3-oxo-2H-pyridazinyl, 1H-2-oxo-pyrimidinyl (e.g., 1H-2-oxo-pyrimidin-6-yl), 1H-2-oxo-pyridinyl, 2,4(1H,3H)-dioxo-pyrimidinyl, and 1H-2-oxo-pyrazinyl. The N-containing 5- to 10-membered heteroaryl group or the N-containing 5- or 6-membered heteroaryl is optionally substituted by 1 or more (such as 1 to 5) suitable substituents.

As used herein, the term "heterocycloalkyl" refers to a monocyclic or polycyclic [including 2 or more rings that are fused together, including spiro, fused, or bridged systems, for example, a bicyclic ring system], saturated or unsaturated, non-aromatic 4- to 15-membered ring system (such as a 4- to 14-membered ring system, 4- to 10-membered ring system, 5- to 10-membered ring system, 4- to 7-membered ring system, or 5- to 6-membered ring system), including 1 to 14 ring-forming carbon atoms and 1 to 10 ring-forming heteroatoms each independently selected from O, S and N. For example, the term "4- to 10-membered heterocycloalkyl" refers to a monocyclic or polycyclic, saturated or unsaturated, non-aromatic 4- to 10-membered ring system that comprises one or more ring-forming heteroatoms each independently selected from O, S and N. For another example, the term "4- to 7-membered heterocycloalkyl" refers to a monocyclic or polycyclic, saturated or unsaturated, non-aromatic 4- to 7-membered ring system that comprises one or more ring-forming heteroatoms each independently selected from O, S and N. For yet another example, the term "5- to 6-membered heterocycloalkyl" refers to a monocyclic, saturated or unsaturated, non-aromatic 5- to 6-membered ring system that comprises one or more ring-forming heteroatoms each independently selected from O, S and N. The heterocycloalkyl group is optionally substituted by 1 or more (such as 1 to 5) suitable substituents. The heterocycloalkyl group can also include one to three oxo or thiono groups.

Examples of such heterocycloalkyl rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, quinuclidinyl, chromanyl, isochromanyl, benzoxazinyl, 2-azabicyclo[2.2.1]heptanonyl, 3-azabicyclo[3.1.0]hexanyl, 3-azabicyclo[4.1.0]heptanyl and the like. Further examples of heterocycloalkyl rings include tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, 1,4-oxazepan-1-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, oxazolidinonyl, 2-oxo-piperidinyl (e.g., 2-oxo-piperidin-1-yl), and the like. Also included in the definition of heterocycloalkyl are moieties that have one or more aromatic rings (including aryl and heteroaryl) fused to the nonaromatic heterocycloalkyl ring, for example pyridinyl, pyrimidinyl, thiophenyl, pyrazolyl, phthalimidyl, naphthalimidyl, and benzo derivatives of the nonaromatic heterocycloalkyl rings. Examples of such aromatic-fused heterocycloalkyl groups include indolinyl, isoindolinyl, isoindolin-1-one-3-yl, 5,7-dihydro-6H-pyrrolo[3,4-b]pyridin-6-yl, 6,7-dihydro-5H-pyrrolo[3,4-d]pyrimidin-6-yl, 4,5,6,7-tetrahydrothieno[2,3-c]pyridine-5-yl, 5,6-dihydrothieno[2,3-c]pyridin-7(4H)-one-5-yl, 1,4,5,6-tetrahydropyrrolo[3,4-c]pyrazol-5-yl, and 3,4-dihydroisoquinolin-1(2H)-one-3-yl groups. The heterocycloalkyl group is optionally substituted by 1 or more (such as 1 to 5) suitable substituents. Examples of heterocycloalkyl groups include 5- or 6-membered monocyclic rings and 9- or 10-membered fused bicyclic rings.

As used herein, the term "N-containing 4- to 10-membered heterocycloalkyl" refers to a 4- to 10-membered heterocycloalkyl group comprising at least one ring-forming nitrogen (N) atom and optionally one or more ring-forming heteroatoms each independently selected from O, S and N. The term "N-containing 5- or 6-membered heterocycloalkyl" refers to a 5- or 6-membered heterocycloalkyl group comprising at least one ring-forming nitrogen (N) atom and optionally one or more ring-forming heteroatoms each independently selected from O, S and N. Examples of N-containing 4- to 10-membered heterocycloalkyl groups include azetidinyl, piperidin-1-yl, piperidin-4-yl, piperazin-1-yl, 1,3-thiazinan-3-yl, 1,4,5,6-tetrahydropyrrolo[3,4-c]pyrazol-5-yl, and 3,4-dihydroisoquinolin-1(2H)-one-3-yl. Examples of N-containing 5- or 6-membered heterocycloalkyl groups include piperidin-1-yl, piperidin-4-yl, piperazin-1-yl, 1,3-thiazinan-3-yl, and morpholino. The N-containing 4- to 10-membered heterocycloalkyl or the N-containing 5- or 6-membered heterocycloalkyl is optionally substituted by 1 or more (such as 1 to 5) suitable substituents.

As used herein, the term "halo" or "halogen" group is defined to include fluorine, chlorine, bromine or iodine.

As used herein, the term "haloalkyl" refers to an alkyl group having one or more halogen substituents (up to perhaloalkyl, i.e., every hydrogen atom of the alkyl group has been replaced by a halogen atom). For example, the term "$C_{1-6}$ haloalkyl" refers to a $C_{1-6}$ alkyl group having one or more halogen substituents (up to perhaloalkyl, i.e., every hydrogen atom of the alkyl group has been replaced by a halogen atom). The term "$C_{1-4}$ haloalkyl" refers to a $C_{1-4}$ alkyl group having one or more halogen substituents (up to perhaloalkyl, i.e., every hydrogen atom of the alkyl group has been replaced by a halogen atom). The term "$C_{1-3}$ haloalkyl" refers to a $C_{1-3}$ alkyl group having one or more halogen substituents (up to perhaloalkyl, i.e., every hydrogen atom of the alkyl group has been replaced by a halogen atom). The term "$C_1$ haloalkyl" refers to a methyl group having one, two, or three halogen substituents. Examples of haloalkyl groups include $CF_3$, $C_2F_5$, $CHF_2$, $CH_2F$, $CH_2CF_3$, $CH_2Cl$ and the like.

As used herein, the term "alkoxy" or "alkyloxy" refers to an —O-alkyl group. The term "$C_{1-6}$ alkoxy" or "$C_{1-6}$ alkyloxy" refers to an —O—($C_{1-6}$ alkyl) group. The term "$C_{1-4}$ alkoxy" or "$C_{1-4}$ alkyloxy" refers to an —O—($C_{1-4}$ alkyl) group. The term "$C_{1-3}$ alkoxy" or "$C_{1-3}$ alkyloxy" refers to an —O—($C_{1-3}$ alkyl) group. Examples of alkoxy include methoxy, ethoxy, propoxy (e.g., n-propoxy and isopropoxy), tert-butoxy, and the like.

As used here, the term "haloalkoxy" refers to an —O-haloalkyl group. The term "$C_{1-6}$ haloalkoxy" refers to an —O—($C_{1-6}$ haloalkyl) group. The term "$C_{1-4}$ haloalkoxy" refers to an —O—($C_{1-4}$ haloalkyl) group. The term "$C_{1-3}$ haloalkoxy" refers to an —O—($C_{1-3}$ haloalkyl) group. The term "$C_1$ haloalkoxy" refers to a methoxy group having one, two, or three halogen substituents. An example of a haloalkoxy group is —OCF$_3$ or —OCHF$_2$.

As used herein, the term "cycloalkoxy" or "cycloalkyloxy" refers to an —O-cycloalkyl group. The term "$C_{3-7}$ cycloalkoxy" or "$C_{3-7}$ cycloalkyloxy" refers to an —O—

($C_{3-7}$ cycloalkyl) group. Examples of cycloalkoxy include $C_{3-7}$ cycloalkoxy (e.g., cyclopropoxy, cyclobutoxy, cyclopentoxy, and the like).

As used here, the term "$C_{6-10}$ aryloxy" refers to an —O—($C_{6-10}$ aryl) group. An example of a $C_{6-10}$ aryloxy group is —O-phenyl [i.e., phenoxy].

As used herein, the term "fluoroalkyl" refers to an alkyl group having one or more fluorine substituents (up to perfluoroalkyl, i.e., every hydrogen atom of the alkyl group has been replaced by fluorine). For example, the term "$C_{1-6}$ fluoroalkyl" refers to a $C_{1-6}$ alkyl group having one or more fluorine substituents (up to perfluoroalkyl, i.e., every hydrogen atom of the $C_{1-6}$ alkyl group has been replaced by fluorine). The term "$C_1$ fluoroalkyl" refers to a $C_1$ alkyl group (i.e., methyl) having 1, 2, or 3 fluorine substituents). Examples of fluoroalkyl groups include $CF_3$, $C_2F_5$, $CH_2CF_3$, $CHF_2$, $CH_2F$, and the like.

As used here, the term "fluoroalkoxy" refers to an —O-fluoroalkyl group. The term "$C_1$ fluoroalkoxy" refers to a methoxy group having one, two, or three fluorine substituents. An example of a $C_1$ fluoroalkoxy group is —$OCF_3$ or —$OCHF_2$.

As used herein, the term "fluorocyclopropyl" refers to a cyclopropyl group having one or more fluorine substituents (up to perfluorocyclopropyl, i.e., every hydrogen atom of the cyclopropyl group has been replaced by fluorine). Examples of fluorocyclopropyl include 2-fluoro-cyclopropan-1-yl or 2,3-difluorocyclopropan-1-yl.

As used herein, the term "hydroxylalkyl" or "hydroxyalkyl" refers to an alkyl group having one or more (e.g., 1, 2, or 3) OH substituents. The term "$C_{1-6}$ hydroxylalkyl" or "$C_{1-6}$ hydroxyalkyl" refers to a $C_{1-6}$ alkyl group having one or more (e.g., 1, 2, or 3) OH substituents. The term "$C_{1-4}$ hydroxylalkyl" or "$C_{1-4}$ hydroxyalkyl" refers to a $C_{1-4}$ alkyl group having one or more (e.g., 1, 2, or 3) OH substituents. Examples of hydroxylalkyl groups include —$CH_2OH$ and —$CH_2CH_2OH$.

As used herein, the term "oxo" refers to =O. When an oxo is substituted on a carbon atom, they together form a carbonyl moiety [—C(=O)—]. When an oxo is substituted on a sulfur atom, they together form a sulfinyl moiety [—S(=O)—]; when two oxo groups are substituted on a sulfur atom, they together form a sulfonyl moiety [—S(=O)$_2$—].

As used herein, the term "thiono" refers to =S. When an thiono is substituted on a carbon atom, they together form a moiety having the structure of —C(=S)—.

As used herein, the term "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group (up to that every hydrogen atom on the designated atom or moiety is replaced with a selection from the indicated substituent group), provided that the normal valency of the designated atom or moiety is not exceeded, and that the substitution results in a stable compound. For example, if a methyl group (i.e., $CH_3$) is optionally substituted, then up to 3 hydrogen atoms on the carbon atom can be replaced with substituent groups.

As used herein, unless specified, the point of attachment of a substituent can be from any suitable position of the substituent. For example, piperidinyl can be piperidin-1-yl (attached through the N atom of the piperidinyl), piperidin-2-yl (attached through the C atom at the 2-position of the piperidinyl), piperidin-3-yl (attached through the C atom at the 3-position of the piperidinyl), or piperidin-4-yl (attached through the C atom at the 4-position of the piperidinyl). For another example, pyridinyl (or pyridyl) can be 2-pyridinyl (or pyridin-2-yl), 3-pyridinyl (or pyridin-3-yl), or 4-pyridinyl (or pyridin-4-yl).

When a bond to a substituent is shown to cross a bond connecting two atoms in a ring, then such substituent may be bonded to any of the ring-forming atoms in that ring that are substitutable (i.e., bonded to one or more hydrogen atoms). For example, as shown in Formula a-101 below, $R^{10}$ may be bonded to either of the two ring carbon atoms, each of which bears a hydrogen atom. For another example, as shown in Moiety $M^1$ below, an $R^{10}$ may be bonded to any ring-forming atom that is substitutable (i.e., bonded to one or more hydrogen atoms; for example, a C or N ring-forming atom). For yet another example, as shown in Formula a-102 below (a substituted imidazo[1,2-a]pyrazine ring), $R^{10}$ may be bonded to either of the two ring carbon atoms in the pyrazine ring (each of which bears a hydrogen atom), and $R^{10a}$ may be bonded to either of the two ring carbon atoms in the imidazo ring (each of which bears a hydrogen atom).

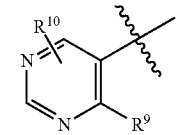

a-101

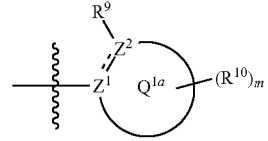

$M^1$

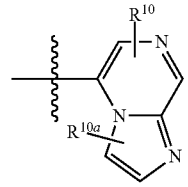

a-102

When a substituted or optionally substituted moiety is described without indicating the atom via which such moiety is bonded to a substituent, then a substituent may be bonded via any appropriate atom in such moiety. For example in a substituted arylalkyl, a substituent on the arylalkyl [e.g., ($C_{6-10}$ aryl)-$C_{1-4}$ alkyl-] can be bonded to any carbon atom on the alkyl part or on the aryl part of the arylalkyl. Combinations of substituents and/or variables are permissible only if such combinations result in stable compounds.

As noted above, the compounds of Formula I may exist in the form of pharmaceutically acceptable salts such as acid addition salts and/or base addition salts of the compounds of Formula I. The phrase "pharmaceutically acceptable salt(s)", as used herein, unless otherwise indicated, includes acid addition or base salts which may be present in the compounds of Formula I.

Pharmaceutically acceptable salts of the compounds of Formula I include the acid addition and base salts thereof.

Suitable acid addition salts are formed from acids which form non-toxic salts. Examples include the acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hibenzate, hydrochloride/ chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulfate and hemicalcium salts.

For a review on suitable salts, see "Handbook of Pharmaceutical Salts: Properties, Selection, and Use" by Stahl and Wermuth (Wiley-VCH, 2002). Methods for making pharmaceutically acceptable salts of compounds of Formula I are known to one of skill in the art.

As used herein the terms "Formula I", "Formula I or pharmaceutically acceptable salts thereof", "pharmaceutically acceptable salts of the compound or the salt [of Formula I]" are defined to include all forms of the compound of Formula I, including hydrates, solvates, isomers (including for example rotational stereoisomers), crystalline and non-crystalline forms, isomorphs, polymorphs, metabolites, and prodrugs thereof.

As it is known to the person skilled in the art, amine compounds (i.e., those comprising one or more nitrogen atoms), for example tertiary amines, can form N-oxides (also known as amine oxides or amine N-oxides). An N-oxide has the formula of $(R^{100}R^{200}R^{300})N^+\!\!-\!\!O^-$ wherein the parent amine $(R^{100}R^{200}R^{300})N$ can be for example, a tertiary amine (for example, each of $R^{100}$, $R^{200}$, $R^{300}$ is independently alkyl, arylalkyl, aryl, heteroaryl, or the like), a heterocyclic or heteroaromatic amine [for example, $(R^{100}R^{200}R^{300})N$ together forms 1-alkylpiperidine, 1-alkylpyrrolidine, 1-benzylpyrrolidine, or pyridine]. For instance, an imine nitrogen, especially heterocyclic or heteroaromatic imine nitrogen, or pyridine-type nitrogen

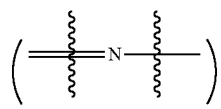

atom [such as a nitrogen atom in pyridine, pyridazine, or pyrazine], can be N-oxidized to form the N-oxide comprising the group

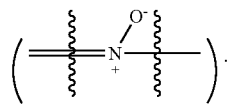

Thus, a compound according to the present invention comprising one or more nitrogen atoms (e.g., an imine nitrogen atom), for example, as a part of $Q^1$ of Formula I, may be capable of forming an N-oxide thereof (e.g., mono-N-oxides, bis-N-oxides or multi-N-oxides, or mixtures thereof depending on the number of nitrogen atoms suitable to form stable N-oxides). For example, a compound of Formula I wherein $Q^1$ is an optionally substituted pyrimidinyl, pyrazinyl, pyridinyl, or pyridazinyl can be oxidized (e.g., in the presence of a suitable oxidizing reagent such as m-chloroperoxybenzoic acid or in the presence of a suitable enzyme) to form its corresponding N-oxide wherein $Q^1$ is converted to its corresponding N-oxide form. For another example, a compound of Formula I wherein $Q^1$ is $Q^1$-101 can be oxidized to form its corresponding N-oxide wherein $Q^1$-101 is converted to $Q^1$-102.

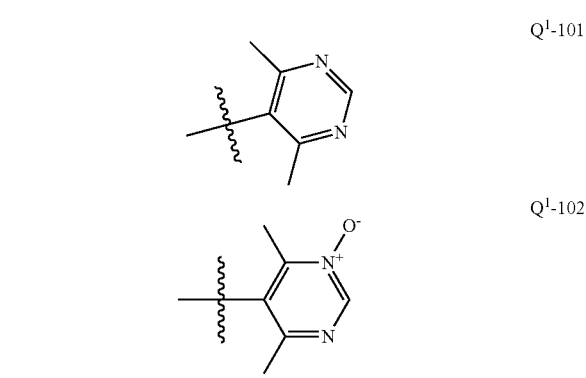

As used herein, the term "N-oxide(s)" refer to all possible, and in particular all stable, N-oxide forms of the amine compounds (e.g., compounds comprising one or more imine nitrogen atoms) described herein, such as mono-N-oxides (including different isomers when more than one nitrogen atom of an amine compound can form a mono-N-oxide) or multi-N-oxides (e.g., bis-N-oxides), or mixtures thereof in any ratio.

The compounds of Formula I can be converted, optionally, into N-oxides thereof, for example, in the presence of a suitable oxidizing reagent in a suitable solvent (e.g., in the presence of hydrogen peroxide in methanol or in the presence of m-chloroperoxybenzoic acid in dichloromethane) or in the presence of an enzyme (e.g. forming an N-oxide thereof as a metabolite). One skilled in the art would readily recognize the reaction conditions suitable for carrying out the N-oxidation reactions.

Compounds of Formula I described herein (compounds of the invention) include N-oxides thereof and pharmaceutically acceptable salts of the compounds or the N-oxides. Examples of N-oxides of compounds of Formula I include those wherein $Q^1$ of Formula I (e.g., an optionally substituted pyrimidinyl such as $Q^1$-101) may be capable of forming an N-oxide thereof.

Compounds of Formula I may exist in a continuum of solid states ranging from fully amorphous to fully crystalline. The term 'amorphous' refers to a state in which the material lacks long-range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from apparent solid to a material with liquid properties occurs, which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

Compounds of Formula I may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of Formula I may exist as clathrates or other complexes (e.g., co-crystals). Included within the scope of the invention are complexes such as clathrates, drug-host inclusion complexes wherein the drug and host are present in stoichiometric or non-stoichiometric amounts. Also included are complexes of the compounds of Formula I containing two or more organic and/or inorganic components, which may be in stoichiometric or non-stoichiometric amounts. The resulting complexes may be ionized, partially ionized, or non-ionized. Co-crystals are typically defined as crystalline complexes of neutral molecular constituents that are bound together through non-covalent interactions, but could also be a complex of a neutral molecule with a salt. Co-crystals may be prepared by melt crystallization, by recrystallization from solvents, or by physically grinding the components together; see O. Almarsson and M. J. Zaworotko, *Chem. Commun.* 2004, 17, 1889-1896. For a general review of multi-component complexes, see J. K. Haleblian, *J. Pharm. Sci.* 1975, 64, 1269-1288.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$CH$_3$)$_3$) polar head group. For more information, see *Crystals and the Polarizing Microscope* by N. H. Hartshorne and A. Stuart, 4$^{th}$ Edition (Edward Arnold, 1970).

The invention also relates to prodrugs of the compounds of Formula I. Thus certain derivatives of compounds of Formula I which may have little or no pharmacological activity themselves can, when administered into or onto the body, be converted into compounds of Formula I having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of Formula I with certain moieties known to those skilled in the art as 'pro-moieties' as described, for example, in Design of Prodrugs by H. Bundgaard (Elsevier, 1985).

Moreover, certain compounds of Formula I may themselves act as prodrugs of other compounds of Formula I.

Also included within the scope of the invention are metabolites of compounds of Formula I, that is, compounds formed in vivo upon administration of the drug. Examples of metabolites of compounds of Formula I include N-oxides of compounds of Formula I wherein Q$^1$ of Formula I may be capable of forming an N-oxide thereof (e.g., wherein Q$^1$ is an optionally substituted pyrimidinyl such as 4,6-dimethylpyrimidin-5-yl).

In some embodiments, the compounds of Formula I include N-oxides thereof and pharmaceutically acceptable salts of the compounds or the N-oxides.

The compounds of Formula I include all stereoisomers and tautomers. Stereoisomers of Formula I include cis and trans isomers, optical isomers such as R and S enantiomers, diastereomers, geometric isomers, rotational isomers, atropisomers, and conformational isomers of the compounds of Formula I, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

In some embodiments, the compounds of Formula I may have asymmetric carbon atoms. The carbon-carbon bonds of the compounds of Formula I may be depicted herein using a solid line (——) a solid wedge ( ▬◀ ), or a dotted wedge ( ·····IIIII ). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

In some embodiments, the compounds of Formula I may exist in and/or be isolated as atropisomers (e.g., one or more atropenantiomers). Those skilled in the art would recognize that atropisomerism may exist in a compound that has two or more aromatic rings (for example, two aromatic rings linked through a single bond). See e.g., Freedman, T. B. et al., Absolute Configuration Determination of Chiral Molecules in the Solution State Using Vibrational Circular Dichroism. *Chirality* 2003, 15, 743-758; and Bringmann, G. et al., Atroposelective Synthesis of Axially Chiral Biaryl Compounds. *Angew. Chem., Int. Ed.* 2005, 44, 5384-5427.

When any racemate crystallizes, crystals of different types are possible. One type is the racemic compound (true racemate) wherein one homogeneous form of crystal is produced containing both enantiomers in equimolar amounts. Another type is a racemic mixture or conglomerate wherein two forms of crystal are produced in equal or different molar amounts each comprising a single enantiomer.

The compounds of Formula I may exhibit the phenomena of tautomerism and structural isomerism. For example, the compounds of Formula I may exist in several tautomeric forms, including the enol and imine form, and the keto and enamine form and geometric isomers and mixtures thereof. All such tautomeric forms are included within the scope of the compounds of Formula I. Tautomers may exist as mixtures of a tautomeric set in solution. In solid form, usually one tautomer predominates. Even though one tautomer may be described, the present invention includes all tautomers of the compounds of Formula I. For example, when one of the following two tautomers of the invention is disclosed in the experimental section herein, those skilled in the art would readily recognize that the invention also includes the other.

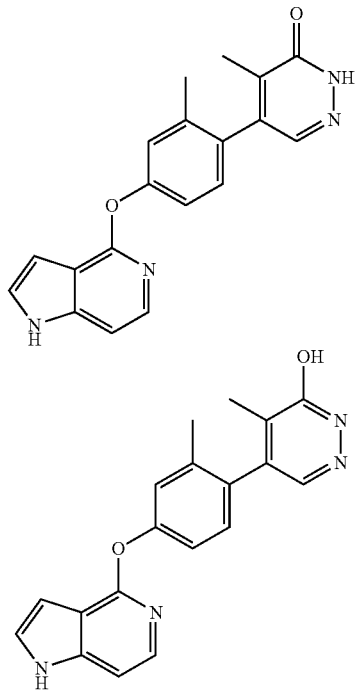

The present invention includes all pharmaceutically acceptable isotopically-labelled compounds of Formula I wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of Formula I, for example, those incorporating a radioactive isotope, are useful in drug and/or substrate tissue distribution studies. The radioactive isotopes tritium, i.e., $^3$H, and carbon-14, i.e., $^{14}$C, are particularly useful for this purpose in view of their ease of incorporation and ready means of detection.

Substitution with heavier isotopes such as deuterium, i.e., $^2$H, may afford certain therapeutic advantages resulting from greater metabolic stability, for example, increased in vivo half-life or reduced dosage requirements, and hence may be preferred in some circumstances.

Substitution with positron-emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of Formula I (or pharmaceutically acceptable salts thereof or N-oxides of the compounds or salts) can generally be prepared by conventional techniques known to those skilled in the art or by processes analogous to those described in the accompanying Examples and Preparations using an appropriate isotopically-labeled reagent in place of the non-labeled reagent previously employed. An embodiment of the present invention is a compound of Formula I wherein $X^1$ is N.

An embodiment of the present invention is a compound of Formula I wherein $X^1$ is $CT^4$.

An embodiment of the present invention is a compound of Formula I wherein each of $T^1$, $T^2$, $T^3$, and $T^4$ is independently selected from the group consisting of H, F, —CN, methoxy, $C_1$ fluoroalkoxy, methyl, and $C_1$ fluoroalkyl. In a further embodiment, $T^1$ is H. In a yet further embodiment, $T^2$ is H. In a still further embodiment, $T^3$ is H, methyl or —CN. In a still further embodiment, $T^3$ is H. In a still further embodiment, $T^4$ is H.

An embodiment of the present invention is a compound of Formula I wherein $T^3$ is H. In a further embodiment, $T^2$ is H and $T^3$ is H.

An embodiment of the present invention is a compound of Formula I wherein the compound is a compound of Formula Ia or Ib:

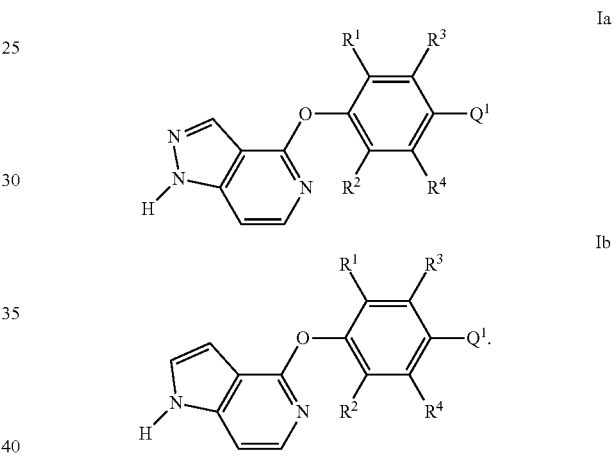

An embodiment of the present invention is a compound of Formula I wherein the compound is a compound of Formula Ia.

An embodiment of the present invention is a compound of Formula I wherein the compound is a compound of Formula Ib.

An embodiment of the present invention is a compound of Formula I (including a compound of Formula Ia or Ib) wherein:

each of $R^1$ and $R^2$ is independently selected from the group consisting of H, halogen, —CN, $C_{1-4}$ alkyl, $C_{1-4}$ haloalkyl, $C_{1-4}$ alkoxy, $C_{1-4}$ haloalkoxy, and $C_{3-4}$ cycloalkyl;

each of $R^3$ and $R^4$ is independently selected from the group consisting of H, halogen, —OH, —CN, $C_{1-4}$ alkyl, $C_{1-4}$ haloalkyl, $C_{1-4}$ haloalkoxy, $C_{3-4}$ cycloalkyl, a 4- to 7-membered heterocycloalkyl, —N($R^5$)($R^6$), and —OR$^8$, each of $R^5$ and $R^6$ independently is H or selected from the group consisting of $C_{1-4}$ alkyl, $C_{1-4}$ haloalkyl, and $C_{3-7}$ cycloalkyl;

or $R^5$ and $R^6$ together with the N atom to which they are attached form a 4- to 7-membered heterocycloalkyl or a 5-membered heteroaryl, each optionally substituted with 1, 2, or 3 substituents each independently selected from the group consisting of halogen, —CN, $C_{1-4}$ alkyl, $C_{1-4}$ alkoxy, $C_{3-6}$ cycloalkyl, $C_{1-4}$ haloalkyl, and $C_{1-4}$ haloalkoxy; and $R^8$ is selected from the group consisting of $C_{1-4}$ alkyl, $C_{3-6}$ cycloalkyl, a 4- to 7-membered heterocycloalkyl, phenyl, and a 5- to 6-membered heteroaryl, each optionally substituted with 1, 2, or 3 substituents each independently selected from the group consisting of halogen, —CN, $C_{1-4}$ alkyl, $C_{1-4}$ haloalkyl, $C_{3-6}$ cycloalkyl, $C_{1-4}$ alkoxy, and $C_{1-4}$ haloalkoxy;

An embodiment of the present invention is a compound of Formula I (including a compound of Formula Ia or Ib) wherein each of $R^1$ and $R^2$ is independently H or halogen. In a further embodiment, each of $R^1$ and $R^2$ is independently H or F. In a yet further embodiment, $R^1$ is H and $R^2$ is H or F. In a still further embodiment, each of $R^1$ and $R^2$ is H An embodiment of the present invention is a compound of Formula I (including a compound of Formula Ia or Ib) wherein each of $R^3$ and $R^4$ is independently H, halogen, —CN, methyl, $C_1$ haloalkyl, methoxy, or $C_1$ haloalkoxy. In a further embodiment, each of $R^3$ and $R^4$ is independently H, halogen, —CN, methyl, or $C_1$ haloalkyl. In a yet further embodiment, $R^3$ is H and $R^4$ is H, F, Cl, —CN, methyl, or $C_1$ haloalkyl. In a still further embodiment, $R^3$ is H and $R^4$ is H, F, or methyl. In a yet still further embodiment, $R^3$ is H and $R^4$ is methyl.

An embodiment of the present invention is a compound of Formula I (including a compound of Formula Ia or Ib) wherein $R^1$ is H; $R^2$ is H or F; $R^3$ is H and $R^4$ is H, F, Cl, —CN, methyl, or $C_1$ haloalkyl. In a further embodiment, each of $R^1$, $R^2$, and $R^3$ is H and $R^4$ is H, or methyl. In a still further embodiment, $R^4$ is methyl.

An embodiment of the present invention is a compound of Formula I (including a compound of Formula Ia or Ib) wherein each of $R^2$ and $R^4$ is H.

An embodiment of the present invention is a compound of Formula I (including a compound of Formula Ia or Ib) wherein:

$Q^1$ is a moiety of

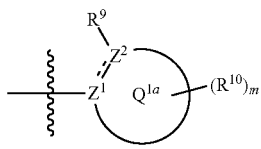

("Moiety $M^1$");

ring $Q^{1a}$ is an N-containing 5- to 6-membered heteroaryl or an N-containing 5- to 6-membered heterocycloalkyl;

===== represents a single bond or double bond;

each of $Z^1$ and $Z^2$ is independently C or N;

$R^9$ is $C_{1-4}$ alkyl, $C_{1-4}$ haloalkyl, $C_{3-7}$ cycloalkyl, —CN, —N($R^5$)($R^6$), $C_{1-6}$ alkoxy, $C_{1-6}$ haloalkoxy, or $C_{3-7}$ cycloalkoxy, wherein each of the $C_{1-4}$ alkyl and $C_{3-7}$ cycloalkyl is optionally substituted with 1, 2, 3, 4, or 5 substituents each independently selected from the group consisting of halogen, —N($R^5$)($R^6$), $C_{1-4}$ alkyl, $C_{1-4}$ haloalkyl, $C_{3-7}$ cycloalkyl, $C_{1-4}$ alkoxy, and $C_{1-4}$ haloalkoxy;

each $R^{10}$ is independently selected from the group consisting of halogen, —OH, —CN, —NO$_2$, oxo, thiono, $C_{1-6}$ alkyl, $C_{1-6}$ haloalkyl, $C_{1-6}$ hydroxylalkyl, $C_{1-6}$ alkoxy, $C_{1-6}$ haloalkoxy, $C_{3-7}$ cycloalkyl, $C_{2-6}$ alkenyl, $C_{2-6}$ alkynyl, $C_{6-10}$ aryl, a 4- to 10-membered heterocycloalkyl, a 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, (5- to 10-membered heteroaryl)-$C_{1-4}$ alkyl-, (5- to 10-membered heteroaryl)-$C_{2-4}$ alkenyl-, —N($R^5$)($R^6$), —N($R^7$)(C(=O)$R^8$), —S(=O)$_2$N($R^5$)($R^6$), —C(=O)—N($R^5$)($R^6$), —C(=O)—$R^8$, —C(=O)—O$R^8$, and —O$R^8$, wherein each of said $C_{1-6}$ alkyl, $C_{3-7}$ cycloalkyl, $C_{6-10}$ aryl, 4- to 10-membered heterocycloalkyl, 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, (5- to 10-membered heteroaryl)-$C_{1-4}$ alkyl-, and (5- to 10-membered heteroaryl)-$C_{2-4}$ alkenyl- is optionally substituted with 1, 2, 3, or 4 substituents each independently selected from the group consisting of halogen, OH, —CN, —NO$_2$, $C_{1-4}$ alkyl, $C_{1-4}$ hydroxylalkyl, $C_{1-4}$ alkoxy, —N($R^5$)($R^6$), —S—($C_{1-4}$ alkyl), —S(=O)$_2$—($C_{1-4}$ alkyl), $C_{6-10}$ aryloxy, ($C_{6-10}$ aryl)-$C_{1-4}$ alkyloxy- optionally substituted with 1 or 2 $C_{1-4}$ alkyl, oxo, —C(=O)H, —C(=O)—$C_{1-4}$ alkyl, —C(=O)O—$C_{1-4}$ alkyl, —C(=O)NH$_2$, —NHC(=O)H, —NHC(=O)—($C_{1-4}$ alkyl), $C_{3-7}$ cycloalkyl, a 5- or 6-membered heteroaryl, $C_{1-4}$ haloalkyl, and $C_{1-4}$ haloalkoxy;

or $R^9$ and the adjacent $R^{10}$ together with the two ring atoms on ring $Q^{1a}$ to which they are attached form a fused benzene ring or a fused 5- or 6-membered heteroaryl, each optionally substituted with 1, 2, 3, 4, or 5 independently selected $R^{10a}$;

each $R^{10a}$ is independently selected from the group consisting of halogen, —OH, —C(=O)OH, —C(=O)—$C_{1-4}$ alkyl, —C(=O)—NH$_2$, —C(=O)—N($C_{1-4}$ alkyl)$_2$, —CN, $C_{1-4}$ alkyl, $C_{1-4}$ alkoxy, $C_{1-4}$ hydroxylalkyl, $C_{1-4}$ haloalkyl, and $C_{1-4}$ haloalkoxy; and m is 0, 1, 2, 3, or 4.

An embodiment of the present invention is a compound of Formula I (including a compound of Formula Ia or Ib) wherein $Q^1$ is Moiety $M^1$ and $Z^1$ is C.

An embodiment of the present invention is a compound of Formula I (including a compound of Formula Ia or Ib) wherein $Q^1$ is Moiety $M^1$ and $Z^1$ is N.

An embodiment of the present invention is a compound of Formula I (including a compound of Formula Ia or Ib) wherein $Q^1$ or ring $Q^{1a}$ (when $Q^1$ is Moiety $M^1$) is an optionally substituted N-containing 6-membered heteroaryl. In a further embodiment, each of the ring-forming atoms of the 6-membered heteroaryl is independently selected from N and C.

An embodiment of the present invention is a compound of Formula I (including a compound of Formula Ia or Ib) wherein $Q^1$ or ring $Q^{1a}$ (when $Q^1$ is Moiety $M^1$) is an optionally substituted pyridinyl, pyrimidinyl, pyridazinyl, or pyrazinyl. In a further embodiment, $Q^1$ or ring $Q^{1a}$ is optionally substituted pyrimidinyl. In a further embodiment, $Q^1$ or ring $Q^{1a}$ is pyrimidinyl substituted with 1 or 2 $C_{1-4}$ alkyl (e.g., $CH_3$).

An embodiment of the present invention is a compound of Formula I (including a compound of Formula Ia or Ib) wherein $Q^1$ is Moiety $M^1$ that is selected from the group consisting of quinolinyl, isoquinolinyl, 1H-imidazo[4,5-c]pyridinyl, imidazo[1,2-a]pyridinyl, 1H-pyrrolo[3,2-c]pyridinyl, imidazo[1,2-a]pyrazinyl, imidazo[2,1-c][1,2,4]triazinyl, imidazo[1,5-a]pyrazinyl, imidazo[1,2-a]pyrimidinyl, 1H-indazolyl, 9H-purinyl, [1,2,4]triazolo[1,5-a]pyrimidinyl, isoxazolo[5,4-c]pyridazinyl, isoxazolo[3,4-c]pyridazinyl, and [1,2,4]triazolo[4,3-b]pyridazinyl, each optionally substituted with 1, 2, or 3 $R^{10}$ and further optionally substituted with 1 or 2 $R^{10a}$; or wherein Moiety $M^1$ is selected from the group consisting of pyrimidinyl, pyrazinyl, pyridinyl, pyridazinyl, 1H-pyrazolyl, 1H-pyrrolyl, 4H-pyrazolyl, 1H-imidazolyl, 3-oxo-2H-pyridazinyl, 1H-2-oxo-pyrimidinyl, 1H-2-oxo-pyridinyl, 2,4(1H,3H)-dioxo-pyrimidinyl, and 1H-2-oxo-pyrazinyl, each substituted with $R^9$ and further optionally substituted with 1, 2, or 3 $R^{10}$.

In a further embodiment, Moiety $M^1$ is selected from the group consisting of pyrimidinyl, pyrazinyl, pyridinyl, and pyridazinyl, each substituted with $R^9$ and further optionally substituted with 1, 2, or 3 $R^{10}$. In a yet further embodiment, Moiety $M^1$ is pyrimidinyl substituted with $R^9$ and further optionally substituted with 1, 2, or 3 $R^{10}$.

An embodiment of the present invention is a compound of Formula I (including a compound of Formula Ia or Ib) wherein $Q^1$ is Moiety $M^1$ that is selected from the group consisting of 3-oxo-2H-pyridazinyl, 2,4(1H,3H)-dioxo-pyrimidinyl, and 1H-2-oxo-pyrazinyl, each substituted with $R^9$ and further optionally substituted with 1, 2, or 3 $R^{10}$.

An embodiment of the present invention is a compound of Formula I (including a compound of Formula Ia or Ib) wherein:
$Q^1$ is Moiety $M^1$ that is

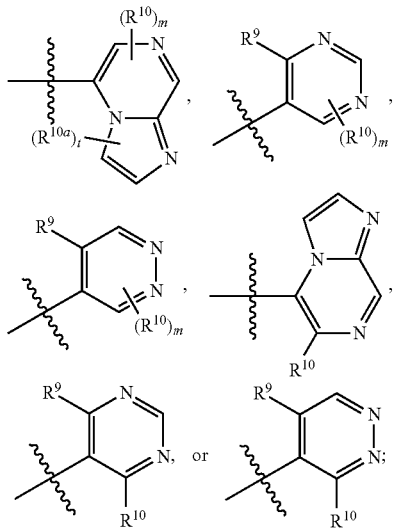

$R^{10a}$ is $C_{1-4}$ alkyl, $C_{1-4}$ haloalkyl, or $C_{3-7}$ cycloalkyl; and t is 0 or 1.

An embodiment of the present invention is a compound of Formula I (including a compound of Formula Ia or Ib) wherein $Q^1$ is Moiety $M^1$ that is

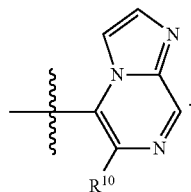

An embodiment of the present invention is a compound of Formula I (including a compound of Formula Ia or Ib) wherein $Q^1$ is

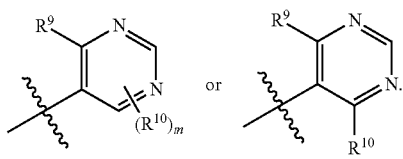

In a further embodiment, $Q^1$ is

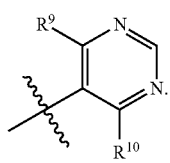

In a yet further embodiment, $Q^1$ is 4,6-dimethylpyrimidin-5-yl.

An embodiment of the present invention is a compound of Formula I (including a compound of Formula Ia or Ib) wherein:
$Q^1$ is Moiety $M^1$ that is

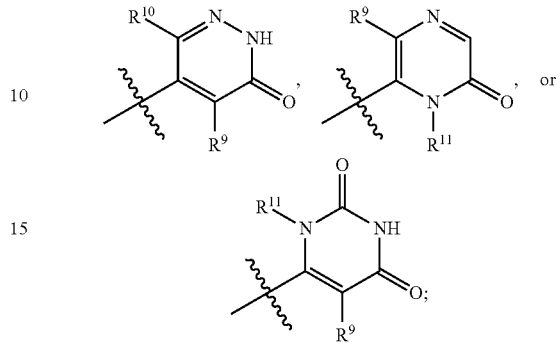

and
$R^{11}$ is H, $C_{1-4}$ alkyl, $C_{1-4}$ haloalkyl, or $C_{3-7}$ cycloalkyl. In a further embodiment, each of $R^9$ and $R^{10}$ (or $R^{11}$) is independently $C_{1-4}$ alkyl (e.g., $CH_3$).

An embodiment of the present invention is a compound of Formula I (including a compound of Formula Ia or Ib) wherein $Q^1$ is 3-oxo-4,6-dimethyl-(2H)pyridazin-5-yl.

An embodiment of the present invention is a compound of Formula I (including a compound of Formula Ia or Ib) wherein $Q^1$ is 2-oxo-1,5-dimethyl-(1H)pyrazin-6-yl.

An embodiment of the present invention is a compound of Formula I (including a compound of Formula Ia or Ib) wherein $Q^1$ is 2,4-dioxo-1,5-dimethyl-(1H,3H)pyrimidin-6-yl.

An embodiment of the present invention is a compound of Formula I (including a compound of Formula Ia or Ib) wherein $R^9$ is $C_{1-4}$ alkyl or —CN. In a further embodiment, $R^9$ is methyl, ethyl, or —CN. In a yet further embodiment, $R^9$ is methyl or —CN. In a still further embodiment, $R^9$ is methyl.

An embodiment of the present invention is a compound of Formula I (including a compound of Formula Ia or Ib) wherein each $R^{10}$ is independently selected from the group consisting of $C_{1-4}$ alkyl, $C_{1-4}$ haloalkyl, —CN, and —N($R^5$)($R^6$), wherein each of $R^5$ and $R^6$ is independently H or is selected from the group consisting of $C_{1-4}$ alkyl, $C_{1-4}$ haloalkyl, and $C_{3-7}$ cycloalkyl; or $R^5$ and $R^6$ together with the N atom to which they are attached form a 4- to 7-membered heterocycloalkyl or a 5-membered heteroaryl, each optionally substituted with 1, 2, or 3 substituents each independently selected from the group consisting of halogen, —CN, $C_{1-4}$ alkyl, $C_{1-4}$ alkoxy, $C_{3-6}$ cycloalkyl, $C_{1-4}$ haloalkyl, and $C_{1-4}$ haloalkoxy. In a further embodiment, each $R^{10}$ is independently selected from the group consisting of methyl, ethyl, and —N($R^5$)($R^6$), wherein $R^5$ and $R^6$ together with the N atom to which they are attached form azetidinyl, pyrrolidinyl, or piperidinyl, each optionally substituted with 1, 2, or 3 substituents each independently selected from the group consisting of halogen, —CN, $C_{1-4}$ alkyl, $C_{1-4}$ alkoxy, $C_{3-6}$ cycloalkyl, $C_{1-4}$ haloalkyl, and $C_{1-4}$ haloalkoxy. In a yet further embodiment, each $R^{10}$ is independently selected from the group consisting of methyl, ethyl, and azetidin-1-yl, wherein the azetidin-1-yl is optionally substituted with 1, 2, or 3, halogen (e.g., F).

An embodiment of the present invention is a compound of Formula I (including a compound of Formula Ia or Ib)

wherein each $R^{10}$ is independently $C_{1-4}$ alkyl. In a further embodiment, each $R^{10}$ is methyl.

In one embodiment, the invention also provides one or more of the compounds described as Examples 1-47 in the Examples section of the subject application, N-oxides thereof, and pharmaceutically acceptable salts of the compounds or the N-oxides.

Another embodiment of the invention relates to a compound selected from the group consisting of:
4-[4-(4,6-dimethylpyrimidin-5-yl)-3-fluorophenoxy]-1H-pyrrolo[3,2-c]pyridine;
(+)-4,6-dimethyl-5-[2-methyl-4-(1H-pyrazolo[4,3-c]pyridin-4-yloxy)phenyl]pyridazin-3(2H)-one;
(−)-4,6-dimethyl-5-[2-methyl-4-(1H-pyrazolo[4,3-c]pyridin-4-yloxy)phenyl]pyridazin-3(2H)-one;
4-[4-(4,6-dimethylpyrimidin-5-yl)-3-methylphenoxy]-1H-pyrrolo[3,2-c]pyridine;
4-[4-(4,6-dimethylpyrimidin-5-yl)-3-methylphenoxy]-1H-pyrazolo[4,3-c]pyridine;
4,6-dimethyl-5-[4-(1H-pyrrolo[3,2-c]pyridin-4-yloxy)phenyl]pyridazin-3(2H)-one;
(−)-1,5-dimethyl-6-[2-methyl-4-(1H-pyrazolo[4,3-c]pyridin-4-yloxy)phenyl]pyrimidine-2,4(1H,3H)-dione;
4,6-dimethyl-5-[2-methyl-4-(1H-pyrrolo[3,2-c]pyridin-4-yloxy)phenyl]pyridazin-3(2H)-one, ENT-1;
4,6-dimethyl-5-[2-methyl-4-(1H-pyrrolo[3,2-c]pyridin-4-yloxy)phenyl]pyridazin-3(2H)-one, ENT-2
4-[4-(4,6-dimethyl-1-oxidopyrimidin-5-yl)-3-methylphenoxy]-1H-pyrazolo[4,3-c]pyridine;
6-methyl-5-[2-methyl-4-(1H-pyrrolo[3,2-c]pyridin-4-yloxy)phenyl]imidazo[1,2-a]pyrazine;
4-[4-(4,6-dimethylpyrimidin-5-yl)phenoxy]-1H-pyrrolo[3,2-c]pyridine;
2-(4,6-dimethylpyrimidin-5-yl)-5-(1H-pyrrolo[3,2-c]pyridin-4-yloxy)benzonitrile;
4-[3-chloro-4-(4,6-dimethylpyrimidin-5-yl)phenoxy]-1H-pyrrolo[3,2-c]pyridine;
(−)-1,5-dimethyl-6-[2-methyl-4-(1H-pyrrolo[3,2-c]pyridin-4-yloxy)phenyl]pyrazin-2(1H)-one;
4-[4-(4,6-dimethylpyrimidin-5-yl)-3-fluorophenoxy]-1H-pyrazolo[4,3-c]pyridine;
4-[4-(4,6-dimethylpyrimidin-5-yl)-3-methoxyphenoxy]-1H-pyrazolo[4,3-c]pyridine;
4-[3-chloro-4-(4,6-dimethylpyrimidin-5-yl)phenoxy]-1H-pyrazolo[4,3-c]pyridine;
(+)-1,5-dimethyl-6-[2-methyl-4-(1H-pyrazolo[4,3-c]pyridin-4-yloxy)phenyl]pyrazin-2(1H)-one;
4,6-dimethyl-5-[4-(1H-pyrazolo[4,3-c]pyridin-4-yloxy)phenyl]pyridazin-3(2H)-one; and
1,5-dimethyl-6-[4-(1H-pyrazolo[4,3-c]pyridin-4-yloxy)phenyl]pyrimidine-2,4(1H,3H)-dione,
or a pharmaceutically acceptable salt thereof.

The present invention also provides compositions (e.g., pharmaceutical compositions) comprising a compound of Formula I (including an N-oxide thereof or a pharmaceutically acceptable salt of the compound or the N-oxide). Accordingly, in one embodiment, the invention provides a pharmaceutical composition comprising (a therapeutically effective amount of) a compound of Formula I (an N-oxide thereof or a pharmaceutically acceptable salt of the compound or the N-oxide) and optionally comprising a pharmaceutically acceptable carrier. In one further embodiment, the invention provides a pharmaceutical composition comprising (a therapeutically effective amount of) a compound of Formula I (an N-oxide thereof or a pharmaceutically acceptable salt of the compound or the N-oxide), optionally comprising a pharmaceutically acceptable carrier and, optionally, at least one additional medicinal or pharmaceutical agent (such as an antipsychotic agent or anti-schizophrenia agent described below). In one embodiment, the additional medicinal or pharmaceutical agent is an anti-schizophrenia agent as described below.

The pharmaceutically acceptable carrier may comprise any conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid, may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration, the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulation, solution or suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages. One of ordinary skill in the art would appreciate that the composition may be formulated in sub-therapeutic dosage such that multiple doses are envisioned.

In one embodiment the composition comprises a therapeutically effective amount of a compound of Formula I (or an N-oxide thereof or a pharmaceutically acceptable salt of the compound or the N-oxide) and a pharmaceutically acceptable carrier.

Compounds of Formula I (including N-oxides thereof and pharmaceutically acceptable salts of the compounds or the N-oxides) are D1 modulators. In some embodiments, a compound of Formula I is a D1 agonist [i.e., binding (having affinity for) and activating D1 receptors]. In some embodiments, using dopamine as a reference full D1 agonist, a compound of Formula I is a superagonist (i.e., a compound that is capable of producing a greater maximal response than the endogenous D1 agonist, dopamine, for a D1 receptor, and thus exhibiting an efficacy of more than about 100%, for example 120%). In some embodiments, using dopamine as a reference full agonist, a compound of Formula I is a full D1 agonist (i.e., having an efficacy of about 100%, for example, 90%-100%, compared to that of dopamine). In some embodiments, using dopamine as a reference full D1 agonist, a compound of Formula I is a partial agonist [i.e., a compound having only partial efficacy (i.e., less than 100%, for example 10%-80% or 50%-70%) at a D1 receptor relative to the full agonist, dopamine, although it binds and activates a D1 receptor]. A D1 agonist (including superagonist, full agonist, and partial agonist) can agonize or partially agonize an activity of D1. In some embodiments, the $EC_{50}$ of a compound of Formula I with respect to D1 is less than about 10 µM, 5 µM, 2 µM, 1 µM, 500 nM, 200 nM, 100 nM, 50, 40, 30, 20, 10, 5, 2, or 1 nM.

The present invention further provides a method for modulating (such as agonizing or partially agonizing) an activity of D1 receptor (either in vitro or in vivo), comprising contacting (including incubating) the D1 receptor with a compound of Formula I (such as one selected from Examples 1-47), or an N-oxide thereof or a pharmaceutically acceptable salt of the compound or the N-oxide.

Another embodiment of the invention includes a method for treating a D1-mediated (or D1-associated) disorder, comprising administering to a mammal (e.g., a human) in need thereof an amount of a compound of Formula I (including a pharmaceutically acceptable salt thereof or an N-oxide of the compound or salt) effective in modulating (e.g., agonizing or partially agonizing) D1.

The compounds of Formula I used for treatment of a D1-mediated disorder also include N-oxides thereof or pharmaceutically acceptable salts of the compounds or the N-oxides.

D1-mediated (or D1-associated) disorders include neurological disorders [such as Tourette's syndrome; tardive dyskinesia; Parkinson's disease (including e.g., cognitive impairment associated with PD); cognitive disorders {including amnesia, age-related cognitive decline, dementia [e.g., senile dementia, Alzheimer's-associated dementia, HIV-associated dementia, Huntington's-associated dementia, Lewy body dementia, vascular dementia, frontotemporal dementia, drug-related dementia (for example, dementia associated with pharmacotherapy therapy such as D2 antagonist therapy)], delirium, and cognitive impairment (e.g., cognitive impairment associated with AD or cognitive impairment associated with PD), and mild cognitive impairment}; Huntington's chorea/disease; and restless leg syndrome (RLS)]; psychiatric disorders [such as cognitive impairment (e.g., cognitive impairment associated with schizophrenia or cognitive impairment associated with pharmacotherapy therapy (e.g., D2 antagonist therapy)); anxiety (including acute stress disorder, generalized anxiety disorder, social anxiety disorder, panic disorder, post-traumatic stress disorder, and obsessive-compulsive disorder); factitious disorder (including acute hallucinatory mania); impulse control disorders/impulsivity (including compulsive gambling and intermittent explosive disorder); mood disorders (including bipolar I disorder, bipolar II disorder, mania, mixed affective state, depression {e.g., age-related depression, major depression, chronic depression, seasonal depression, psychotic depression, postpartum depression, and treatment resistant depression (TRD)}; psychomotor disorders; psychotic disorders [including schizophrenia (including, for example, cognitive and negative symptoms in schizophrenia), schizoaffective disorder, schizophreniform, and delusional disorder]; substance abuse and drug dependence (including narcotic dependence, alcoholism, amphetamine dependence, cocaine addiction, nicotine dependence, and drug withdrawal syndrome); drug abuse relapse, eating disorders (including anorexia, bulimia, binge eating disorder, overeating, hyperphagia, and pagophagia); autism spectrum disorder (e.g., autism); chronic apathy, anhedonia, chronic fatigue, seasonal affective disorder, and pediatric psychiatric disorders (including attention deficit disorder, attention deficit hyperactive disorder (ADHD), conduct disorder, and autism)], endocrine disorders (such as hyperprolactinemia), or other disorders including drowsiness, excessive daytime sleepiness, cachexia, inattention, sexual dysfunction (e.g., erectile dysfunction, post-SSRI sexual dysfunction), pain, migraine, systemic lupus erythematosus (SLE), hyperglycemia, atherosclerosis, dislipidemia, obesity, diabetes, sepsis, post-ischemic tubular necrosis, renal failure, hyponatremia, resistant edema, narcolepsy, cardiovascular disease (e.g., hypertension), congestive heart failure, postoperative ocula hypotonia, sleep disorders, and serotonin syndrome.

Another embodiment of the invention provides a method for treating neurological disorders [such as Tourette's syndrome; tardive dyskinesia; Parkinson's disease; cognitive disorders {including amnesia, senile dementia, HIV-associated dementia, Alzheimer's-associated dementia, Huntington's-associated dementia, Lewy body dementia, vascular dementia, drug-related dementia (for example, cognitive impairment associated with D2 antagonist therapy), delirium, and mild cognitive impairment)}; RLS; and Huntington's chorea/disease], psychiatric disorders [such as anxiety (including acute stress disorder, generalized anxiety disorder, social anxiety disorder, panic disorder, post-traumatic stress disorder and obsessive-compulsive disorder); factitious disorder (including acute hallucinatory mania); impulse control disorders/impulsivity (including compulsive gambling and intermittent explosive disorder); mood disorders (including bipolar I disorder, bipolar II disorder, mania, mixed affective state, major depression, chronic depression, seasonal depression, psychotic depression, and postpartum depression); psychomotor disorders; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, and pagophagia); and pediatric psychiatric disorders (including attention deficit disorder, attention deficit/hyperactive disorder, conduct disorder, and autism)], or endocrine disorders (such as hyperprolactinemia) in a mammal, for example a human, comprising administering to said mammal a therapeutically effective amount of a compound of Formula I.

Another embodiment of the invention includes a method for treating a disorder in a mammal (e.g., a human), which method comprises administering to said mammal a therapeutically effective amount of a compound of Formula I, wherein the disorder is selected from schizophrenia (e.g., cognitive and negative symptoms in schizophrenia), cognitive impairment [e.g., cognitive impairment associated with schizophrenia, cognitive impairment associated with AD, cognitive impairment associated with PD, cognitive impairment associated with pharmacotherapy therapy (e.g., D2 antagonist therapy), and mild cognitive impairment], attention deficit hyperactivity disorder (ADHD), impulsivity, compulsive gambling, an eating disorder (e.g., anorexia, bulimia, binge eating disorder, overeating, hyperphagia, and pagophagia), autism spectrum disorder, mild cognitive impairment (MCI), age-related cognitive decline, dementia (e.g., senile dementia, HIV-associated dementia, Alzheimer's dementia, Lewy body dementia, vascular dementia, or frontotemporal dementia), restless leg syndrome (RLS), Parkinson's disease, Huntington's chorea, anxiety, depression (e.g., age-related depression), major depressive disorder (MDD), treatment resistant depression (TRD), bipolar disorder, chronic apathy, anhedonia, chronic fatigue, post-traumatic stress disorder, seasonal affective disorder, social anxiety disorder, post-partum depression, serotonin syndrome, substance abuse and drug dependence, drug abuse relapse, Tourette's syndrome, tardive dyskinesia, drowsiness, excessive daytime sleepiness, cachexia, inattention, sexual dysfunction (e.g., erectile dysfunction or post-SSRI sexual dysfunction), migraine, systemic lupus erythematosus (SLE), hyperglycemia, atherosclerosis, dislipidemia, obesity, diabetes, sepsis, post-ischemic tubular necrosis, renal failure, hyponatremia, resistant edema, narcolepsy, hypertension, congestive heart failure, postoperative ocular hypotonia, sleep disorders, and pain.

Another embodiment of the invention includes a method for treating schizophrenia (e.g., cognitive and negative symptoms in schizophrenia or cognitive impairment associated with schizophrenia) or psychosis in a mammal, for example a human, comprising administering to said mammal (e.g., a human) a therapeutically effective amount of a compound of Formula I.

Another embodiment of the invention includes a method for treating schizophrenia (e.g., cognitive and negative symptoms in schizophrenia or cognitive impairment associated with schizophrenia) in a mammal, for example a human, comprising administering to said mammal a therapeutically effective amount of a compound of Formula I.

Another embodiment of the invention includes a method for the treatment of cognitive impairment [e.g., cognitive impairment associated with schizophrenia, cognitive impairment associated with AD, or cognitive impairment associated with PD] in a mammal, for example a human, comprising administering to said mammal a therapeutically effective amount of a compound of Formula I.

Another embodiment of the invention includes a method for treating AD (e.g., treating cognitive impairment associated with AD), PD (e.g., treating cognitive impairment associated with PD), RLS, depression, or MDD in a mammal, for example a human, comprising administering to said mammal a therapeutically effective amount of a compound of Formula I.

The term "therapeutically effective amount" as used herein refers to that amount of the compound (including a pharmaceutically acceptable salt thereof or an N-oxide of the compound or salt) being administered which will relieve to some extent one or more of the symptoms of the disorder being treated. In reference to the treatment of a D1-mediated disorder (e.g., schizophrenia), a therapeutically effective amount refers to that amount which has the effect of relieving to some extent (or, for example, eliminating) one or more symptoms associated with a D1-mediated disorder (e.g., schizophrenia, or cognitive and negative symptoms in schizophrenia, or cognitive impairment associated with schizophrenia).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined herein. The term "treating" also includes adjuvant and neoadjuvant treatment of a subject.

Administration of the compounds of Formula I may be effected by any method that enables delivery of the compounds to the site of action. These methods include oral routes, intranasal routes, inhaled routes, intraduodenal routes, parenteral injection (including intravenous, subcutaneous, intramuscular, intravascular or infusion), topical, and rectal administration.

In one embodiment of the present invention, the compounds of Formula I may be administered/effected by oral routes.

Dosage regimens may be adjusted to provide the optimum desired response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specifications for the dosage unit forms of the invention are dictated by a variety of factors such as the unique characteristics of the therapeutic agent and the particular therapeutic or prophylactic effect to be achieved. In one embodiment of the present invention, the compounds of Formula I may be used to treat humans.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent is well-known in the relevant art and would be understood to be encompassed by the skilled artisan once provided the teachings disclosed herein.

The amount of the compound of Formula I administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases still larger doses may be employed without causing any harmful side effect, provided that such larger doses are first divided into several small doses for administration throughout the day.

As used herein, the term "combination therapy" refers to the administration of a compound of Formula I together with an at least one additional pharmaceutical or medicinal agent (e.g., an anti-schizophrenia agent), either sequentially or simultaneously.

The present invention includes the use of a combination of a compound of Formula I and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I (including an N-oxide thereof or a pharmaceutically acceptable salt of the compound or the N-oxide); (b) a second pharmaceutically active agent; and (c) a pharmaceutically acceptable carrier, vehicle or diluent.

Various pharmaceutically active agents may be selected for use in conjunction with the compounds of Formula I, depending on the disease, disorder, or condition to be treated. Pharmaceutically active agents that may be used in combination with the compositions of the present invention include, without limitation:

(i) acetylcholinesterase inhibitors such as donepezil hydrochloride (ARICEPT, MEMAC); or Adenosine $A_{2A}$ receptor antagonists such as Preladenant (SCH 420814) or SCH 412348;

(ii) amyloid-β (or fragments thereof), such as $Aβ_{1-15}$ conjugated to pan HLA DR-binding epitope (PADRE) and ACC-001 (Elan/Wyeth;

(iii) antibodies to amyloid-β (or fragments thereof), such as bapineuzumab (also known as AAB-001) and AAB-002 (Wyeth/Elan);

(iv) amyloid-lowering or -inhibiting agents (including those that reduce amyloid production, accumulation and fibrillization) such as colostrinin and bisnorcymserine (also known as BNC);

(v) alpha-adrenergic receptor agonists such as clonidine (CATAPRES);

(vi) beta-adrenergic receptor blocking agents (beta blockers) such as carteolol;

(vii) anticholinergics such as amitriptyline (ELAVIL, ENDEP);

(viii) anticonvulsants such as carbamazepine (TEGRETOL, CARBATROL);

(ix) antipsychotics, such as lurasidone (also known as SM-13496; Dainippon Sumitomo);

(x) calcium channel blockers such as nilvadipine (ESCOR, NIVADIL);

(xi) catechol O-methyltransferase (COMT) inhibitors such as tolcapone (TASMAR);

(xii) central nervous system stimulants such as caffeine;

(xiii) corticosteroids such as prednisone (STERAPRED, DELTASONE);

(xiv) dopamine receptor agonists such as apomorphine (APOKYN);

(xv) dopamine receptor antagonists such as tetrabenazine (NITOMAN, XENAZINE, dopamine D2 antagonist such as Quetiapine);

(xvi) dopamine reuptake inhibitors such as nomifensine maleate (MERITAL);

(xvii) gamma-aminobutyric acid (GABA) receptor agonists such as baclofen (LIORESAL, KEMSTRO);

(xviii) histamine 3 ($H_3$) antagonists such as ciproxifan;

(xix) immunomodulators such as glatiramer acetate (also known as copolymer-1; COPAXONE);

(xx) immunosuppressants such as methotrexate (TREXALL, RHEUMATREX);

(xxi) interferons, including interferon beta-1a (AVONEX, REBIF) and interferon beta-1b (BETASERON, BETAFERON);

(xxii) levodopa (or its methyl or ethyl ester), alone or in combination with a DOPA decarboxylase inhibitor (e.g., carbidopa (SINEMET, CARBILEV, PARCOPA));

(xxiii) N-methyl-D-aspartate (NMDA) receptor antagonists such as memantine (NAMENDA, AXURA, EBIXA);

(xxiv) monoamine oxidase (MAO) inhibitors such as selegiline (EMSAM);

(xxv) muscarinic receptor (particularly M1 subtype) agonists such as bethanechol chloride (DUVOID, URECHOLINE);

(xxvi) neuroprotective drugs such as 2,3,4,9-tetrahydro-1H-carbazol-3-one oxime;

(xxvii) nicotinic receptor agonists such as epibatidine;

(xxviii) norepinephrine (noradrenaline) reuptake inhibitors such as atomoxetine (STRATTERA);

(xxix) phosphodiesterase (PDE) inhibitors, for example, PDE9 inhibitors such as BAY 73-6691 (Bayer AG) and PDE 10 (e.g. PDE10A) inhibitors such as papaverine;

(xxx) other PDE inhibitors including (a) PDE1 inhibitors (e.g., vinpocetine), (b) PDE2 inhibitors (e.g., erythro-9-(2-hydroxy-3-nonyl)adenine (EHNA)), (c) PDE4 inhibitors (e.g., rolipram), and (d) PDE5 inhibitors (e.g., sildenafil (VIAGRA, REVATIO));

(xxxi) quinolines such as quinine (including its hydrochloride, dihydrochloride, sulfate, bisulfate and gluconate salts);

(xxxii) β-secretase inhibitors such as WY-25105;

(xxxiii) γ-secretase inhibitors such as LY-411575 (Lilly);

(xxxiv) serotonin (5-hydroxytryptamine) 1A ($5-HT_{1A}$) receptor antagonists such as spiperone;

(xxxv) serotonin (5-hydroxytryptamine) 4 ($5-HT_4$) receptor agonists such as PRX-03140 (Epix);

(xxxvi) serotonin (5-hydroxytryptamine) 6 ($5-HT_6$) receptor antagonists such as mianserin (TORVOL, BOLVIDON, NORVAL);

(xxxvii) serotonin (5-HT) reuptake inhibitors such as alaproclate, citalopram (CELEXA, CIPRAMIL);

(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline;

and the like.

The compound of Formula I is optionally used in combination with another active agent. Such an active agent may be, for example, an atypical antipsychotic or an anti-Parkinson's disease agent or an anti-Alzheimer's agent. Accordingly, another embodiment of the invention provides methods of treating a D1-mediated disorder (e.g., a neurological and psychiatric disorder associated with D1), comprising administering to a mammal an effective amount of a compound of Formula I (including an N-oxide thereof or a pharmaceutically acceptable salt of the compound or the N-oxide) and further comprising administering another active agent.

As used herein, the term "another active agent" refers to any therapeutic agent, other than the compound of Formula I (including an N-oxide thereof or a pharmaceutically acceptable salt of the compound or the N-oxide) that is useful for the treatment of a subject disorder. Examples of additional therapeutic agents include antidepressants, antipsychotics (such as anti-schizophrenia), anti-pain, anti-Parkinson's disease agents, anti-LID (levodopa-induced dyskinesia), anti-Alzheimer's and anti-anxiety agents. Examples of particular classes of antidepressants that can be used in combination with the compounds of the invention include norepinephrine reuptake inhibitors, selective serotonin reuptake inhibitors (SSRIs), NK-1 receptor antagonists, monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, and atypical antidepressants. Suitable norepinephrine reuptake inhibitors include tertiary amine tricyclics and secondary amine tricyclics. Examples of suitable tertiary amine tricyclics and secondary amine tricyclics include amitriptyline, clomipramine, doxepin, imipramine, trimipramine, dothiepin, butriptyline, iprindole, lofepramine, nortriptyline, protriptyline, amoxapine, desipramine and maprotiline. Examples of suitable selective serotonin reuptake inhibitors include fluoxetine, fluvoxamine, paroxetine, and sertraline. Examples of monoamine oxidase inhibitors include isocarboxazid, phenelzine, and tranylcyclopramine. Examples of suitable reversible inhibitors of monoamine oxidase include moclobemide. Examples of suitable serotonin and noradrenaline reuptake inhibitors of use in the present invention include venlafaxine. Examples of suitable atypical anti-depressants include bupropion, lithium, nefazodone, trazodone and viloxazine. Examples of anti-Alzheimer's agents include Dimebon, NMDA receptor antagonists such as memantine; and cholinesterase inhibitors such as donepezil and galantamine. Examples of suitable classes of anti-anxiety agents that can be used in combination with the compounds of the invention include benzodiazepines and serotonin 1A (5-HT1A) agonists or antagonists, especially 5-HT1A partial agonists, and corticotropin releasing factor (CRF) antagonists. Suitable benzodiazepines include alprazolam, chlordiazepoxide, clonazepam, chlorazepate, diazepam, halazepam, lorazepam, oxazepam, and prazepam. Suitable 5-HT1A receptor agonists or antagonists include buspirone, flesinoxan, gepirone, and ipsapirone. Suitable atypical antipsychotics include paliperidone, bifeprunox, ziprasidone, risperidone, aripiprazole, olanzapine, and quetiapine. Suitable nicotine acetylcholine agonists include ispronicline, varenicline and MEM 3454. Anti-pain agents include pregabalin, gabapentin, clonidine, neostigmine, baclofen, midazolam, ketamine and ziconotide. Examples of suitable anti-Parkinson's disease agents include L-DOPA (or its methyl or ethyl ester), a DOPA decarboxylase inhibitor (e.g., carbidopa (SINEMET, CARBILEV, PARCOPA), an Adenosine $A_{2A}$ receptor antagonist [e.g., Preladenant (SCH 420814) or SCH 412348], benserazide (MADOPAR), α-methyldopa, monofluoromethyldopa, difluoromethyldopa, brocresine, or m-hydroxybenzylhydrazine), a dopamine agonist [such as apomorphine (APOKYN), bromocriptine (PARLODEL), cabergoline (DOSTINEX), dihydrexidine, dihydroergocryptine, fenoldopam (CORLOPAM), lisuride (DOPERGIN), pergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), and sarizotan], a monoamine oxidase (MAO) inhibitor [such as selegiline (EMSAM), selegiline hydrochloride (L-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL)], a catechol O-methyltransferase (COMT) inhibitor [such as tolcapone (TASMAR), entacapone (COMTAN), and tropolone], an N-methyl-D-aspartate (NMDA) receptor antagonist [such as amantadine (SYMMETREL)], anticholinergics [such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE, tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL)], or a combination thereof. Examples of anti-schizophrenia agents include ziprasidone, risperidone, olanzapine, quetiapine, aripiprazole, asenapine, blonanserin, or iloperidone.

As noted above, the compounds of Formula I (including N-oxides thereof and pharmaceutically acceptable salts of the compounds or salts) may be used in combination with one or more additional anti-schizophrenia agents which are described herein. When a combination therapy is used, the one or more additional anti-schizophrenia agents may be administered sequentially or simultaneously with the compound of the invention. In one embodiment, the additional anti-schizophrenia agent is administered to a mammal (e.g., a human) prior to administration of the compound of the invention. In another embodiment, the additional anti-schizophrenia agent is administered to the mammal after administration of the compound of the invention. In another embodiment, the additional anti-schizophrenia agent is administered to the mammal (e.g., a human) simultaneously with the administration of the compound of the invention (or an N-oxide thereof or a pharmaceutically acceptable salt of the foregoing).

The invention also provides a pharmaceutical composition for the treatment of schizophrenia in a mammal, including a human, which comprises an amount of a compound of Formula I (or an N-oxide thereof or a pharmaceutically acceptable salt of the foregoing), as defined above (including hydrates, solvates and polymorphs of said compound or pharmaceutically acceptable salts thereof), in combination with one or more (for example one to three) anti-schizophrenia agents such as ziprasidone, risperidone, olanzapine, quetiapine, aripiprazole, asenapine, blonanserin, or iloperidone, wherein the amounts of the active agent and the combination when taken as a whole are therapeutically effective for treating schizophrenia.

The invention also provides a pharmaceutical composition for the treatment of Parkinson's disease in a mammal (including cognition impairment associated with PD), including a human, which comprises an amount of a compound of Formula I (or an N-oxide thereof or a pharmaceutically acceptable salt of the foregoing), as defined above (including hydrates, solvates and polymorphs of said compound or pharmaceutically acceptable salts thereof), in combination with one or more (for example one to three) anti-Parkinson's disease agents such as L-DOPA, wherein the amounts of the active agent and the combination when taken as a whole are therapeutically effective for treating Parkinson's disease.

It will be understood that the compounds of Formula I depicted above are not limited to the particular enantiomer shown, but also include all stereoisomers and mixtures thereof.

DETAILED DESCRIPTION OF THE INVENTION

Compounds of the invention, including N-oxides and salts of the compounds or N-oxides, can be prepared using known organic synthesis techniques and can be synthesized according to any of numerous possible synthetic routes.

The reactions for preparing compounds of the invention can be carried out in suitable solvents, which can be readily selected by one of skill in the art of organic synthesis. Suitable solvents can be substantially non-reactive with the starting materials (reactants), the intermediates, or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

Compounds of Formula I and intermediates thereof may be prepared according to the following reaction schemes and accompanying discussion. Unless otherwise indicated, $R^1$, $R^2$, $R^3$, $R^4$, $R^5$, $R^6$, $R^7$, $R^8$, $R^9$, $R^{10}$, $R^{11}$, $T^1$, $T^2$, $T^3$, $Q^1$, and $X^1$, and structural Formula I in the reaction schemes and discussion that follow are as defined above. In general the compounds of this invention may be made by processes which include processes analogous to those known in the chemical arts, particularly in light of the description contained herein. Certain processes for the manufacture of the compounds of this invention and intermediates thereof are provided as further features of the invention and are illustrated by the following reaction schemes. Other processes are described in the experimental section. The schemes and examples provided herein (including the corresponding description) are for illustration only, and not intended to limit the scope of the present invention.

Scheme 1 refers to preparation of compounds of Formula I. Referring to Scheme 1, compounds of Formula 1-1 [where Lg$^1$ is a suitable leaving group such as halo (e.g., Cl or Br) and Pg$^1$ is a suitable protecting group, such as tert-butoxycarbonyl (Boc), [2-(trimethylsilyl)ethoxy]methyl (SEM), or 2-tetrahydropyranyl (THP)] and 1-2 [wherein Z$^1$ is a halogen (Cl, Br, or I)] are commercially available or can be made by methods described herein or other methods well known to those skilled in the art. A compound of Formula 1-3 can be prepared by coupling a compound of Formula 1-1 with a compound of Formula 1-2 under suitable conditions. The coupling can be accomplished, for example, by heating a mixture of a compound of Formula 1-1 with a compound of Formula 1-2 in the presence of a base, such as Cs$_2$CO$_3$, in an appropriate solvent, such as DMSO. Alternatively, a metal-catalyzed (such as using a palladium or copper catalyst) coupling may be employed to accomplish the aforesaid coupling. In this variant of the coupling, a mixture of a compound of Formula 1-1 and a compound of Formula 1-2 can be heated in the presence of a base (such as Cs$_2$CO$_3$), a metal catalyst [such as a palladium catalyst, e.g., [Pd(OAc)$_2$], and a ligand (such as BINAP) in an appropriate solvent, such as 1,4-dioxane. A compound of Formula 1-3 can subsequently be reacted with a compound of Formula Q$^1$–Z$^2$ [wherein Z$^2$ can be Br; B(OH)$_2$; B(OR)$_2$ wherein each R is independently H or C$_{1-6}$ alkyl, or wherein the two (OR) groups, together with the B atom to which they are attached, form a 5- to 10-membered heterocycloalkyl or heteroaryl optionally substituted with one or more C$_{1-6}$ alkyl; a trialkyltin moiety; or the like] by a metal-catalyzed (such as using a palladium catalyst) coupling reaction to obtain a compound of Formula I. Compounds of Formula Q$^1$–Z$^2$ are commercially available or can be made by methods described herein or by methods analogous to those described in the chemical art. Alternatively, a compound of Formula 1-3 can be converted to a compound of Formula 1-4 (wherein Z$^2$ is defined as above). For example, a compound of Formula 1-3 (wherein Z$^1$ is halogen such as Br) can be converted to a compound of Formula 1-4 [wherein Z$^2$ is B(OH)$_2$; B(OR)$_2$ wherein each R is independently H or C$_{1-6}$ alkyl, or wherein the two (OR) groups, together with the B atom to which they are attached, form a 5- to 10-membered heterocycloalkyl or heteroaryl optionally substituted with one or more C$_{1-6}$ alkyl] by methods described herein or other methods well known to those skilled in the art. In this example, this reaction can be accomplished, for example, by reacting a compound of Formula 1-3 (wherein Z$^1$ is halogen such as Br) with 4,4,4',4',5,5,5',5'-octamethyl-2,2'-bi-1,3,2-dioxaborolane, a suitable base (such as potassium acetate), and a palladium catalyst {such as [1,1'-bis(diphenylphosphino)ferrocene]dichloropalladium(II)} in a suitable solvent such as 1,4-dioxane. In another example, a compound of Formula 1-3 (wherein Z$^1$ is halogen such as Br) can be converted to a compound of Formula 1-4 (wherein Z$^2$ is a trialkyltin moiety) by alternate methods described herein or other methods well known to those skilled in the art. In this example, this reaction can be accomplished, for example, by reacting a compound of Formula 1-3 (wherein Z$^1$ is halogen such as Br) with a hexaalkyldistannane (such as hexamethyldistannane) in the presence of a palladium catalyst [such as tetrakis(triphenylphosphine)palladium(0)] in a suitable solvent such as 1,4-dioxane. A compound of Formula 1-4 can then be reacted with a compound of Formula Q$^1$–Z$^1$ (wherein Z$^1$ is defined as above) by a metal-catalyzed (such as using a palladium catalyst) coupling reaction to obtain a compound of Formula I. Compounds of Formula Q$^1$–Z$^1$ are commercially available or can be made by methods described herein or by methods analogous to those described in the chemical art. The type of reaction employed depends on the selection of Z$^1$ and Z$^2$. For example, when Z$^1$ is halogen or triflate and the Q$^1$–Z$^2$ reagent is a boronic acid or boronic ester, a Suzuki reaction may be used [A. Suzuki, *J. Organomet. Chem.* 1999, 576, 147-168; N. Miyaura and A. Suzuki, *Chem. Rev.* 1995, 95, 2457-2483; A. F. Littke et al., *J. Am. Chem. Soc.* 2000, 122, 4020-4028]. In some specific embodiments, an aromatic iodide, bromide, or triflate of Formula 1-3 is combined with an aryl or heteroaryl boronic acid or boronic ester of Formula Q$^1$–Z$^2$ and a suitable base, such as potassium phosphate, in a suitable organic solvent such as tetrahydrofuran (THF). A palladium catalyst is added, such as S-Phos precatalyst {also known as chloro(2-dicyclohexylphosphino-2',6'-dimethoxy-1,1'-biphenyl)[2-(2-aminoethylphenyl)]palladium(II)-tert-butyl methyl ether adduct}, and the reaction mixture is heated. Alternatively, when Z$^1$ is halogen or triflate and Z$^2$ is trialkyltin, a Stille coupling may be employed [V. Farina et al., *Organic Reactions* 1997, 50, 1-652]. More specifically, a compound of Formula 1-3 (wherein Z$^1$ is bromide, iodide, or triflate) may be combined with a compound of Formula Q$^1$–Z$^2$ (wherein the Q$^1$–Z$^2$ compound is a Q$^1$ stannane compound) in the presence of a palladium catalyst, such as dichlorobis(triphenylphosphine)palladium(II), in a suitable organic solvent such as toluene, and the reaction may be heated.

Where $Z^1$ is Br, I, or triflate and $Z^2$ is Br or I, a Negishi coupling may be used [E. Erdik, *Tetrahedron* 1992, 48, 9577-9648]. More specifically, a compound of Formula 1-3 (wherein $Z^1$ is bromide, iodide, or triflate) may be transmetallated by treatment with 1 to 1.1 equivalents of an alkyllithium reagent followed by a solution of 1.2 to 1.4 equivalents of zinc chloride in an appropriate solvent such as THF at a temperature ranging from −80° C. to −65° C. After warming to a temperature between 10° C. and 30° C., the reaction mixture may be treated with a compound of Formula $Q^1$-$Z^2$ (wherein $Z^2$ is Br or I), and heated at 50° C. to 70° C. with addition of a catalyst such as tetrakis(triphenylphosphine)palladium(0). The reaction may be carried out for times ranging from 1 to 24 hours. The compound of Formula 1-5 may then be deprotected, using appropriate conditions depending on the selection of the $Pg^1$ group, to obtain a compound of Formula I. None of these reactions are limited to the employment of the solvent, base, catalyst, or ligand described above, as many other conditions may be used.

Scheme 2 also refers to preparation of compounds of Formula I. Referring to Scheme 2, compounds of Formula I may be prepared utilizing analogous chemical transformations to those described in Scheme 1, but with a different ordering of steps. Compounds of Formula 2-1 [wherein $Pg^2$ is a suitable protecting group such as methyl, benzyl, THP, or triisopropylsilyl (TIPS)] are commercially available or can be made by methods described herein or other methods well known to those skilled in the art. A compound of Formula 2-1 can be converted to a compound of Formula 2-2 either directly or after conversion to a compound of Formula 2-3 using methods analogous to those described in Scheme 1. A compound of Formula 2-2 may then be deprotected, using appropriate conditions depending on the selection of the $Pg^2$ group, to obtain a compound of Formula 2-4, which in turn can be coupled with a compound of Formula 1-1 in Scheme 1 to afford a compound of Formula 1-5. The coupling conditions employed may be analogous to those described for the preparation of a compound of Formula 1-3 in Scheme 1. A compound of Formula 1-5 may then be deprotected, using appro- Scheme 1

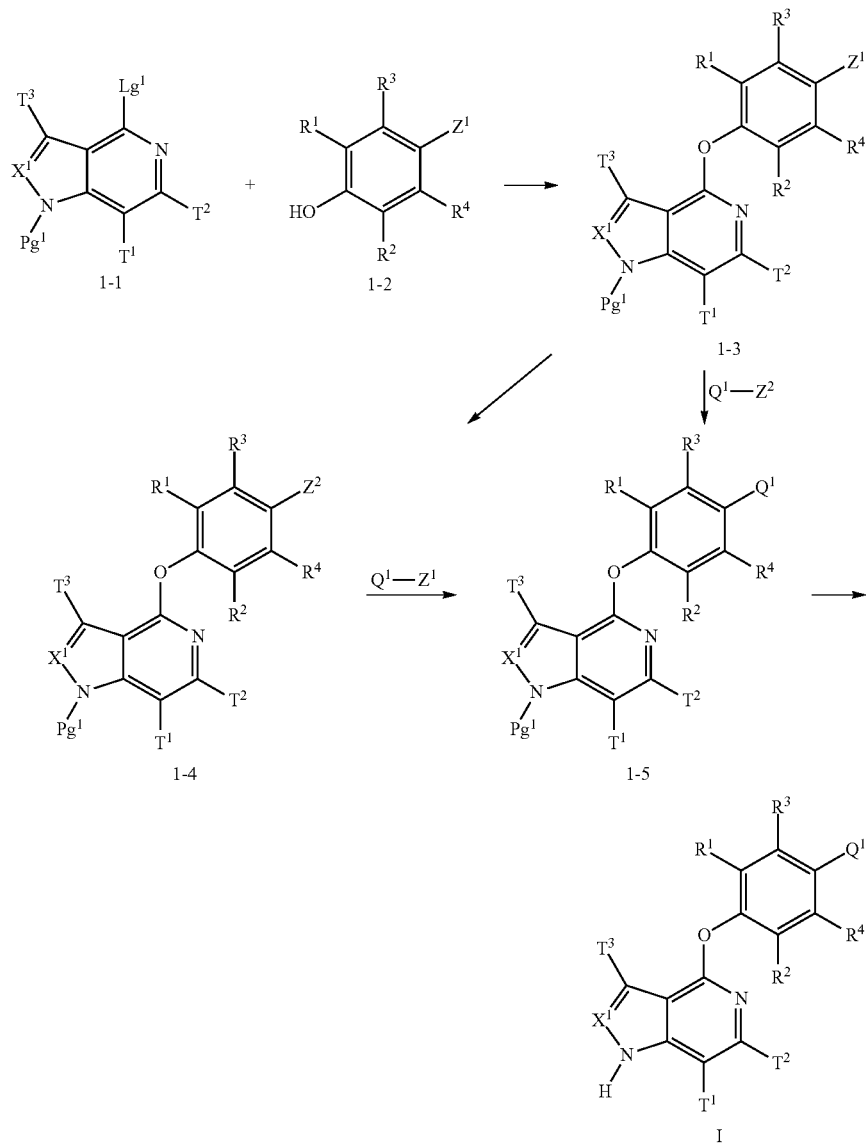

priate conditions depending on the selection of the Pg¹ group, to obtain a compound of Formula I.

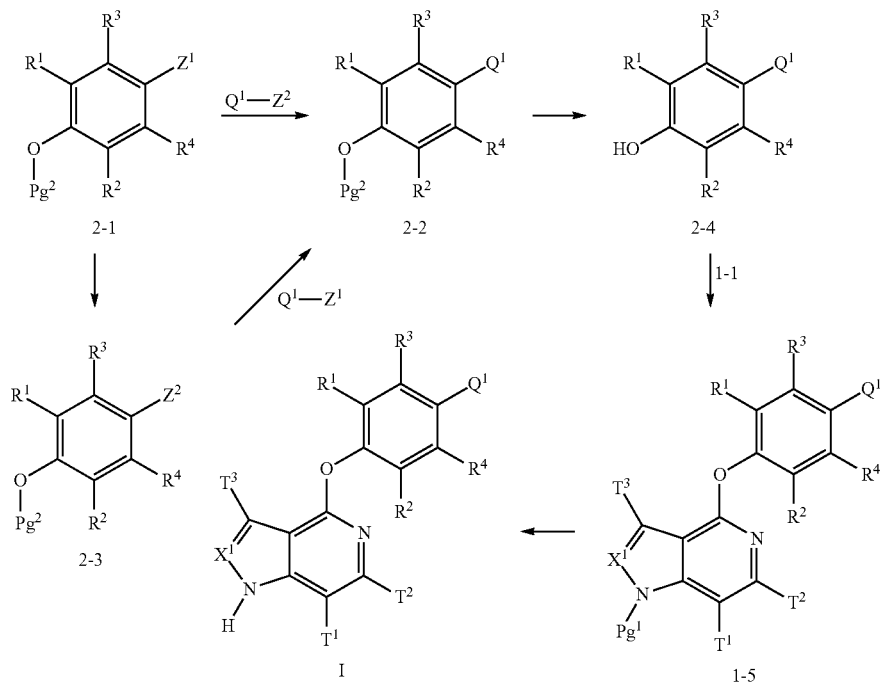

Scheme 3 refers to a preparation of a compound of Formula 3-3 (wherein A¹ is either Pg² as defined above or a moiety of Formula A¹ᵃ), which can be used in Scheme 2 as intermediate/starting material for the preparation of compounds of Formula I. Referring to Scheme 3, compounds of Formula 3-1 are commercially available or can be made by methods described herein or other methods well known to those skilled in the art. A compound of Formula 3-1 can be reacted with 4-chloro-3-nitropyridine and the initial product can be subsequently reduced to obtain a compound of Formula 3-2. Examples of suitable reaction conditions for the coupling of a compound of Formula 3-1 with 4-chloro-3-nitropyridine include mixing the two reactants with a suitable base, such as triethylamine, in a suitable reaction solvent such as ethanol. The subsequent reduction of the nitro group to afford a compound of Formula 3-2 can be achieved by, for example, hydrogenation in the presence of a catalyst such as palladium on carbon in a suitable solvent such as methanol. Suitable hydrogen pressures for the aforesaid reaction are typically between 1 atm and 4 atm. A compound of Formula 3-2 can then be heated with acetic anhydride and triethyl orthoformate to obtain a compound of Formula 3-3.

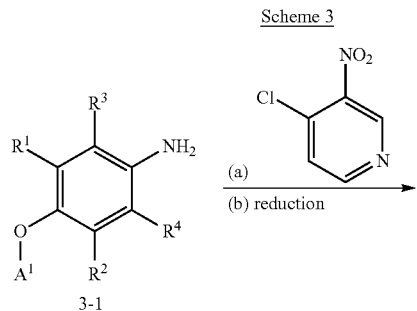

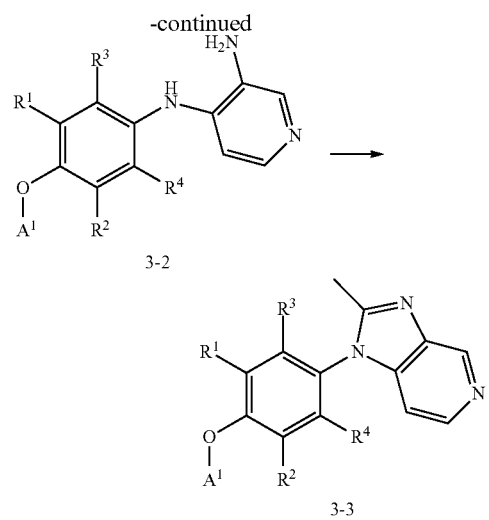

A¹ is Pg² or a moiety of A¹ᵃ:

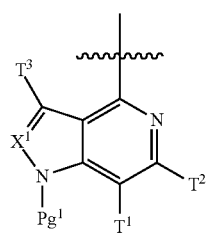

Scheme 4 refers to a preparation of a compound of Formula 4-4 or 4-5 (wherein R⁹ is such as $C_{1-3}$ alkyl, for example methyl), which can be used in Scheme 2 as intermediate/starting material for the preparation of compounds of Formula I. Referring to Scheme 4, compounds of Formula 4-1 are commercially available or can be made by methods described herein or other methods well known to those skilled in the art. A compound of Formula 4-2 can be prepared by reacting an arylketone of Formula 4-1 with an alkyl nitrite (e.g., isoamyl nitrite) in the presence of an acid (such as hydrochloric acid). The resulting oxime of Formula 4-2 can be converted to the diketone of Formula 4-3 upon treatment with formaldehyde (or its equivalent such as metaformaldehyde or polyformaldehyde) in the presence of an acid (such as an aqueous hydrochloric acid solution). Diketones of Formula 4-3 can be reacted with glycinamide or a salt thereof (such as an acetic acid salt) in the presence of a base such as sodium hydroxide to obtain pyrazinones of Formula 4-4. Alkylation of the pyrazinone nitrogen to obtain a compound of Formula 4-5 can be achieved by treatment of a compound of Formula 4-4 with a base [such as LDA, LHMDS, and the like] and a compound of the formula $R^{11}$—$Z^3$ [wherein $Z^3$ is an acceptable leaving group such as Cl, Br, I, methanesulfonate, and the like and wherein $R^{11}$ is for example $C_{1-3}$ alkyl (e.g., methyl)]. Suitable reaction solvents typically can be selected from polar aprotic solvents such as N,N-dimethylformamide (DMF), 1,4-dioxane, or THF.

ate/starting material for the preparation of compounds of Formula I. Referring to Scheme 5, compounds of Formula 5-1 and 5-2 are commercially available or can be made by methods described herein or other methods well known to those skilled in the art. A compound of Formula 5-3 can be prepared by coupling a compound of Formula 5-1 with a compound of Formula 5-2. The aforesaid coupling may be accomplished by reacting a compound of Formula 5-1 with a compound of Formula 5-2 in the presence of a suitable base (such as potassium carbonate), a suitable catalyst [such as tetrakis(triphenylphosphine)palladium(0)], and a suitable solvent (such as ethanol). A compound of Formula 5-3 can be reacted with maleic anhydride and hydrogen peroxide in a solvent (such as dichloromethane) to provide a compound of Formula 5-4, which may contain a mixture of N-oxide regioisomers. A compound of Formula 5-5 can be prepared from a compound of Formula 5-4 by heating with acetic anydride; the initial product can be saponified using a base (such as NaOH) in a suitable polar solvent (such as water or methanol). A compound of Formula 4-5 can be prepared from a compound of Formula 5-5 by reaction with a suitable base (such as LDA, LHMDS and the like), lithium bromide, and a compound of the formula $R^{11}$—$Z^3$ (wherein $Z^3$ is an acceptable leaving group such as Cl, Br, I, methanesulfonate, and the like). Suitable reaction solvents typically can be selected from polar aprotic solvents (such as DMF, 1,4-dioxane, or THF).

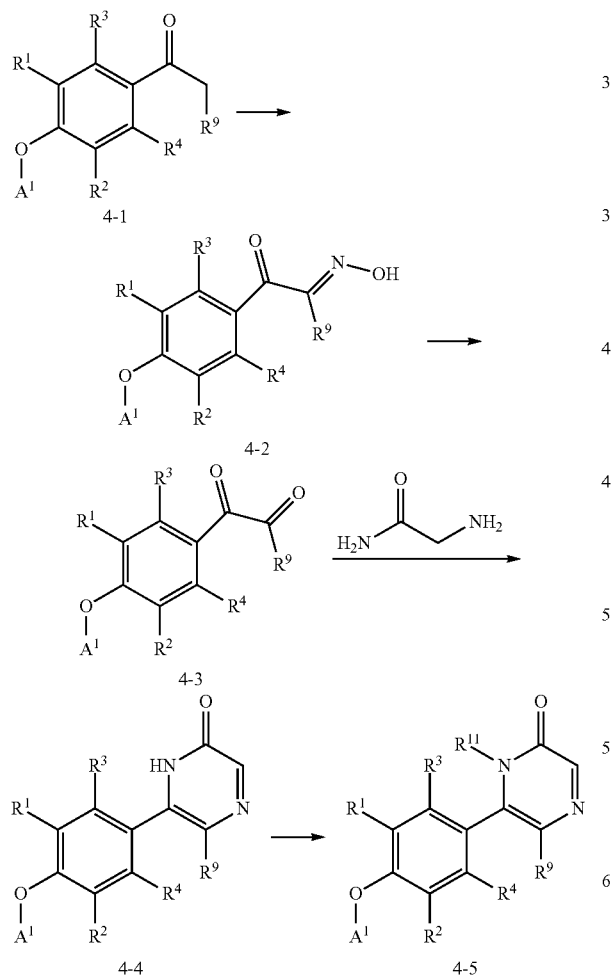

Scheme 4

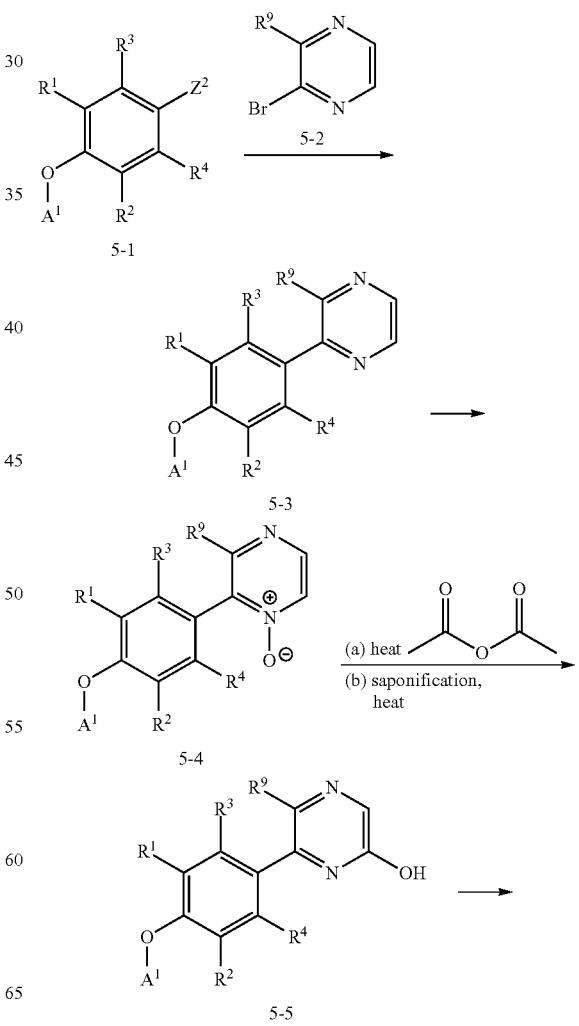

Scheme 5

Alternatively, a compound of Formula 4-5 may be prepared as in Scheme 5 [wherein $R^{11}$ is, for example, H or $C_{1-3}$ alkyl (e.g., methyl)], which can be used in Scheme 2 as intermedi-

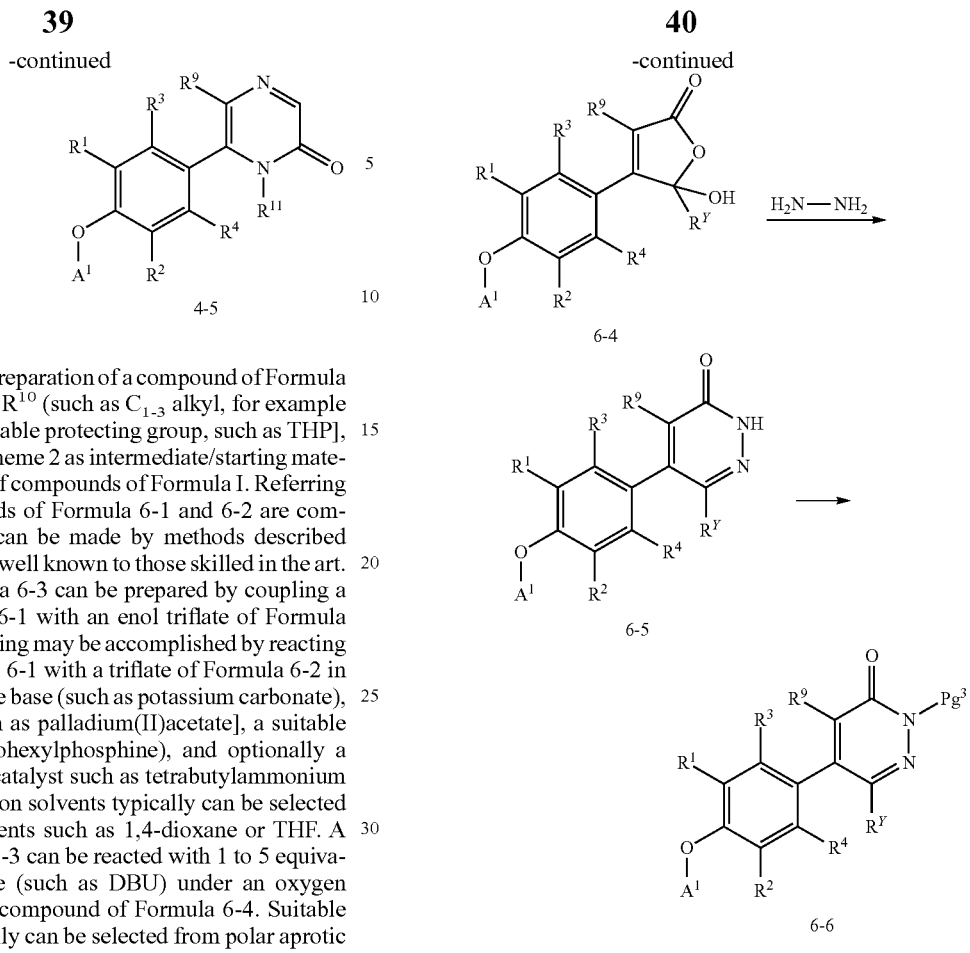

Scheme 6 refers to a preparation of a compound of Formula 6-6 [wherein $R^Y$ is H or $R^{10}$ (such as $C_{1-3}$ alkyl, for example methyl) and $Pg^3$ is a suitable protecting group, such as THP], which can be used in Scheme 2 as intermediate/starting material for the preparation of compounds of Formula I. Referring to Scheme 6, compounds of Formula 6-1 and 6-2 are commercially available or can be made by methods described herein or other methods well known to those skilled in the art. A compound of Formula 6-3 can be prepared by coupling a compound of Formula 6-1 with an enol triflate of Formula 6-2. The aforesaid coupling may be accomplished by reacting a compound of Formula 6-1 with a triflate of Formula 6-2 in the presence of a suitable base (such as potassium carbonate), a suitable catalyst [such as palladium(II)acetate], a suitable ligand (such as tricyclohexylphosphine), and optionally a suitable phase transfer catalyst such as tetrabutylammonium chloride. Suitable reaction solvents typically can be selected from polar aprotic solvents such as 1,4-dioxane or THF. A compound of Formula 6-3 can be reacted with 1 to 5 equivalents of a suitable base (such as DBU) under an oxygen atmosphere to obtain a compound of Formula 6-4. Suitable reaction solvents typically can be selected from polar aprotic solvents such as DMF, 1,4-dioxane, or THF. A compound of Formula 6-5 can be obtained by reacting a compound of Formula 6-4 with hydrazine in a suitable solvent such as 1-butanol. A compound of Formula 6-5 can be converted to a suitably protected compound of Formula 6-6 using methods described herein or other methods well known to those skilled in the art.

Scheme 6

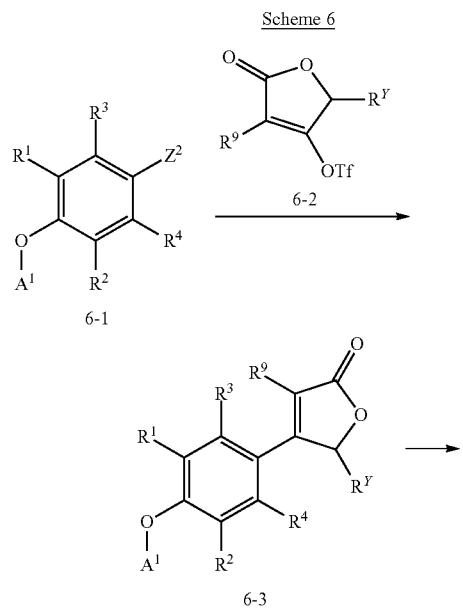

Scheme 7 refers to a preparation of a compound of Formula 7-6 [wherein $R^Y$ is H or $R^{10}$ (such as $C_{1-3}$ alkyl, for example methyl)], which can be used in Scheme 2 as intermediate/starting material for the preparation of compounds of Formula I. Referring to Scheme 7, compounds of Formula 7-1 and 7-2 are commercially available or can be made by methods described herein or other methods well known to those skilled in the art. A compound of Formula 7-3 can be prepared by coupling a compound of Formula 7-1 with a compound of Formula 7-2 [wherein $Pg^4$ is a suitable protecting group such as THP]. The aforesaid coupling may be accomplished by heating a compound of Formula 7-1 with a compound of Formula 7-2 in the presence of a suitable base (such as cesium carbonate) and a suitable catalyst {such as [1,1'-bis(diphenylphosphino)ferrocene]dichloropalladium(II)}. Suitable reaction solvents typically can be selected from polar aprotic solvents such as 1,4-dioxane or THF. A compound of Formula 7-4 can be obtained by removing the protecting group $Pg^4$, for example, by treating a compound of Formula 7-3 (wherein $Pg^4$ is, for example, THP) with HCl in an alcoholic solvent (such as 2-propanol). Treatment of a compound of Formula 7-4 with phosphorous oxychloride at elevated temperature can provide a compound of Formula 7-5. A compound of Formula 7-5 can be a reactive intermediate in numerous chemical transformations to obtain a compound of Formula 7-6. For example, a compound of Formula 7-5 can be reacted with trimethylaluminum and a suitable palladium catalyst [such as tetrakis(triphenylphosphine)palladium(0)] in 1,4-dioxane to afford a compound of Formula 7-6 (wherein the newly introduced $R^9$ is methyl).

Scheme 7

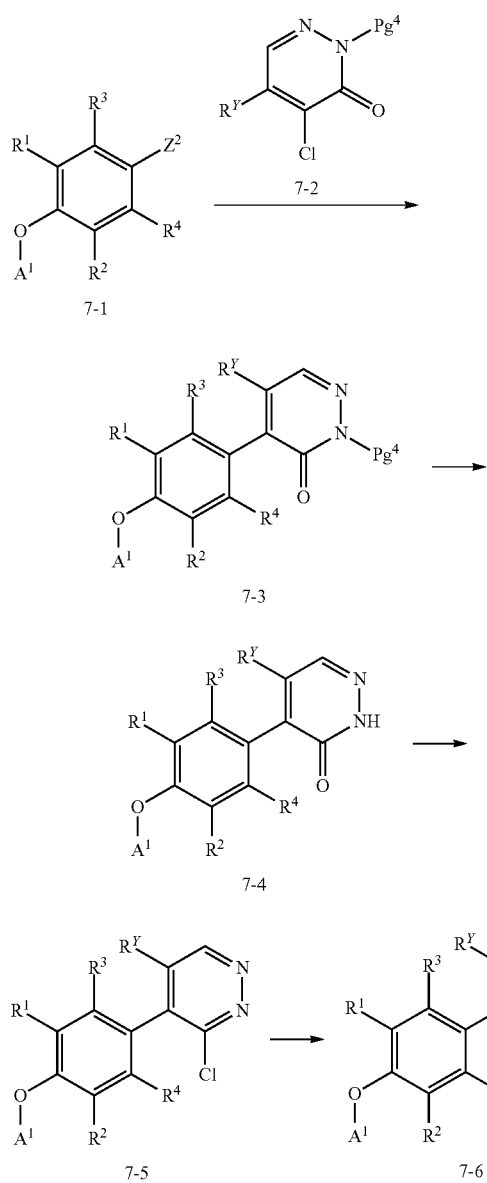

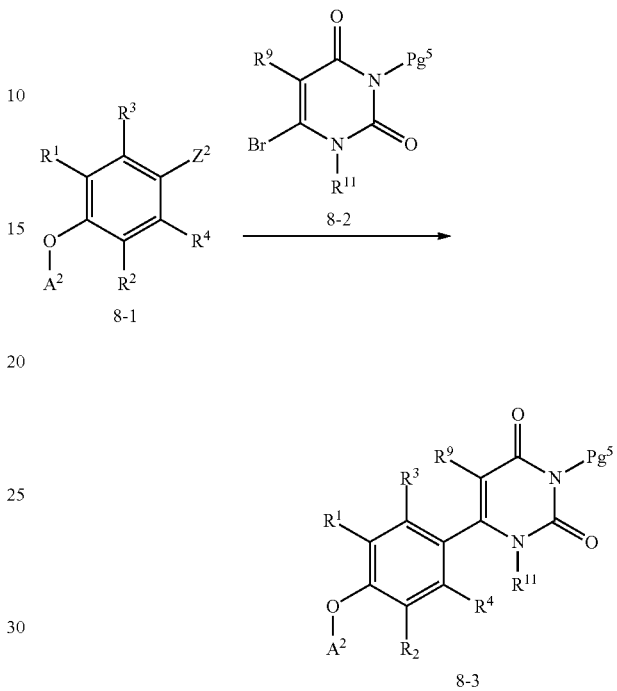

ate) and a suitable catalyst {such as [1,1'-bis(diphenylphosphino)ferrocene]dichloropalladium(II)}.

Scheme 8 refers to a preparation of a compound of Formula 8-3 [wherein $R^9$ is for example $C_{1-3}$ alkyl (e.g., methyl); $R^{11}$ is for example H or $C_{1-3}$ alkyl (e.g., methyl); and $Pg^5$ is a suitable protecting group [e.g., SEM, Boc, or benzyloxymethyl acetal (BOM)]; $A^2$ is H or $Pg^2$; and $Pg^2$ is a suitable protecting group (e.g., methoxymethyl (MOM) or benzyl)], which can be used in Scheme 2 as intermediate/starting material for the preparation of compounds of Formula I. Referring to Scheme 8, compounds of Formula 8-1 and 8-2 are commercially available or can be prepared by methods described herein or other methods well known to those skilled in the art. A compound of Formula 8-3 can be prepared by coupling a compound of Formula 8-1 with a compound of Formula 8-2. The aforesaid coupling may be accomplished by heating a compound of Formula 8-1 with a compound of Formula 8-2 in the presence of a suitable base (such as potassium carbon- Alternatively, a compound of Formula I may also be prepared by enzymatic modification (such as a microbial oxidation) of a related compound of Formula I. For example, as shown in Scheme 9, incubation of a compound of Formula I {for example, wherein $Q^1$ is a moiety that can be oxidized, such as an optionally substituted pyridazinyl in a compound of Formula 9-1 [wherein $R^Y$ is H or $R^{10}$ (such as $C_{1-3}$ alkyl, for example methyl)]} with *Pseudomonas putida* for a reaction time between 24 and 96 hours in a suitable buffer can provide an alternate compound of Formula I (for example, wherein $Q^1$ is an optionally substituted pyridazinonyl in a compound of Formula 9-2).

Scheme 9

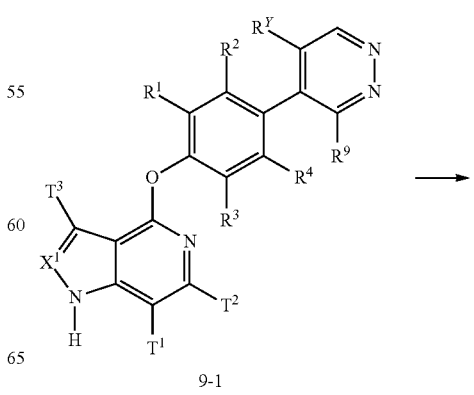

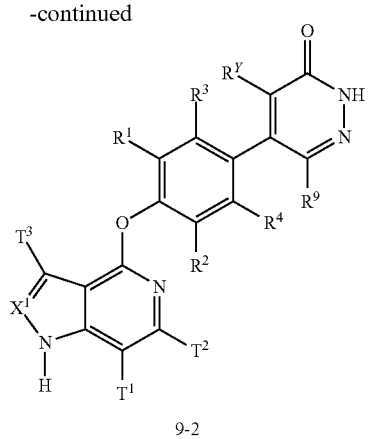

9-2

Additional starting materials and intermediates useful for making the compounds of the present invention can be obtained from chemical vendors such as Sigma-Aldrich or can be made according to methods described in the chemical art.

Those skilled in the art can recognize that in all of the Schemes described herein, if there are functional (reactive) groups present on a part of the compound structure such as a substituent group, for example $R^1$, $R^2$, $R^3$, $R^4$, $R^5$, $R^6$, $R^7$, $R^8$, $R^9$, $R^{10}$, $Q^1$, etc., further modification can be made if appropriate and/or desired, using methods well known to those skilled in the art. For example, a —CN group can be hydrolyzed to afford an amide group; a carboxylic acid can be converted to an amide; a carboxylic acid can be converted to an ester, which in turn can be reduced to an alcohol, which in turn can be further modified. For another example, an OH group can be converted into a better leaving group such as a mesylate, which in turn is suitable for nucleophilic substitution, such as by a cyanide ion (CN⁻). For another example, an —S— can be oxidized to —S(=O)— and/or —S(=O)$_2$—. For yet another example, an unsaturated bond such as C=C or C≡C can be reduced to a saturated bond by hydrogenation. In some embodiments, a primary amine or a secondary amine moiety (present on a substituent group such as $R^3$, $R^4$, $R^9$, $R^{10}$, etc.) can be converted to an amide, sulfonamide, urea, or thiourea moiety by reacting it with an appropriate reagent such as an acid chloride, a sulfonyl chloride, an isocyanate, or a thioisocyanate compound. One skilled in the art will recognize further such modifications. Thus, a compound of Formula I having a substituent that contains a functional group can be converted to another compound of Formula I having a different substituent group.

Similarly, those skilled in the art can also recognize that in all of the schemes described herein, if there are functional (reactive) groups present on a substituent group such as $R^3$, $R^4$, $R^9$, $R^{10}$, etc., these functional groups can be protected/deprotected in the course of the synthetic scheme described here, if appropriate and/or desired. For example, an OH group can be protected by a benzyl, methyl, or acetyl group, which can be deprotected and converted back to the OH group in a later stage of the synthetic process. For another example, an NH$_2$ group can be protected by a benzyloxycarbonyl (Cbz) or Boc group; conversion back to the NH$_2$ group can be carried out at a later stage of the synthetic process via deprotection.

As used herein, the term "reacting" (or "reaction" or "reacted") refers to the bringing together of designated chemical reactants such that a chemical transformation takes place generating a compound different from any initially introduced into the system. Reactions can take place in the presence or absence of solvent.

Compounds of Formula I may exist as stereoisomers, such as atropisomers, racemates, enantiomers, or diastereomers. Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of Formula I (and chiral precursors thereof) may be obtained in enantiomerically enriched form using chromatography, typically HPLC, on an asymmetric resin with a mobile phase consisting of a hydrocarbon, typically heptane or hexane, containing from 0% to 50% 2-propanol, typically from 2% to 20%, and from 0% to 5% of an alkylamine, typically 0.1% diethylamine. Concentration of the eluate affords the enriched mixture. Stereoisomeric conglomerates may be separated by conventional techniques known to those skilled in the art. See, e.g., *Stereochemistry of Organic Compounds* by E. L. Eliel and S. H. Wilen (Wiley, New York, 1994), the disclosure of which is incorporated herein by reference in its entirety. Suitable stereoselective techniques are well-known to those of ordinary skill in the art.

Where a compound of Formula I contains an alkenyl or alkenylene (alkylidene) group, geometric cis/trans (or Z/E) isomers are possible. Cis/trans isomers may be separated by conventional techniques well known to those skilled in the art, for example, chromatography and fractional crystallization. Salts of the present invention can be prepared according to methods known to those of skill in the art.

The compounds of Formula I that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the basic compounds of this invention can be prepared by treating the basic compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, isonicotinic acid, lactic acid, pantothenic acid, bitartric acid, ascorbic acid, 2,5-dihydroxybenzoic acid, gluconic acid, saccharic acid, formic acid, methanesulfonic acid, ethanesulfonic acid, benzenesulfonic acid, p-toluenesulfonic acid, and pamoic [i.e., 4,4'-methanediylbis(3-hydroxynaphthalene-2-carboxylic acid)] acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as ethanesulfonic acid, or the like.

Those compounds of Formula I that are acidic in nature are capable of forming base salts with various pharmacologically acceptable cations. Examples of such salts include the alkali metal or alkaline earth metal salts, and particularly the sodium and potassium salts. These salts are all prepared by conventional techniques. The chemical bases which are used as reagents to prepare the pharmaceutically acceptable base salts of this invention are those which form non-toxic base salts with the acidic compounds of Formula I. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, for example under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are, for example, employed in order to ensure completeness of reaction and maximum yields of the desired final product.

Pharmaceutically acceptable salts of compounds of Formula I (including compounds of Formula Ia or Ib) may be prepared by one or more of three methods:

(i) by reacting the compound of Formula I with the desired acid or base;

(ii) by removing an acid- or base-labile protecting group from a suitable precursor of the compound of Formula I or by ring-opening a suitable cyclic precursor, for example, a lactone or lactam, using the desired acid or base; or (iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

Polymorphs can be prepared according to techniques well-known to those skilled in the art, for example, by crystallization.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture may have almost identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, New York, 1994).

The invention also includes isotopically labeled compounds of Formula I wherein one or more atoms is replaced by an atom having the same atomic number, but an atomic mass or mass number different from the atomic mass or mass number usually found in nature. Isotopically labeled compounds of Formula I (or pharmaceutically acceptable salts thereof or N-oxides thereof) can generally be prepared by conventional techniques known to those skilled in the art or by processes analogous to those described herein, using an appropriate isotopically labeled reagent in place of the non-labeled reagent otherwise employed.

Prodrugs in accordance with the invention can, for example, be produced by replacing appropriate functionalities present in the compounds of Formula I with certain moieties known to those skilled in the art as 'pro-moieties' as described, for example, in *Design of Prodrugs* by H. Bundgaard (Elsevier, 1985).

The compounds of Formula I should be assessed for their biopharmaceutical properties, such as solubility and solution stability (across pH), permeability, etc., in order to select the most appropriate dosage form and route of administration for treatment of the proposed indication.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention (or pharmaceutically acceptable salts thereof) and methods for their preparation will be readily apparent to those skilled in the art. Such compositions and methods for their preparation may be found, for example, in *Remington's Pharmaceutical Sciences*, 19th Edition (Mack Publishing Company, 1995).

The compounds of the invention (including pharmaceutically acceptable salts thereof and N-oxides thereof) may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropyl methyl cellulose) and typically comprise a carrier, for example, water, ethanol, polyethylene glycol, propylene glycol, methyl cellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described by Liang and Chen, *Expert Opinion in Therapeutic Patents* 2001, 11, 981-986.

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 weight % to 25 weight %, for example, from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulfate. Lubricants generally comprise from 0.25 weight % to 10 weight %, for example, from 0.5 weight % to 3 weight % of the tablet.

Other possible ingredients include anti-oxidants, colorants, flavoring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt-congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of Formula I, a film-forming polymer, a binder, a solvent, a humectant, a plasticizer, a stabilizer or emulsifier, a viscosity-modifying agent and a solvent. Some components of the formulation may perform more than one function.

The compound of Formula I (or pharmaceutically acceptable salts thereof or N-oxides thereof) may be water-soluble or insoluble. A water-soluble compound typically comprises from 1 weight % to 80 weight %, more typically from 20 weight % to 50 weight %, of the solutes. Less soluble compounds may comprise a smaller proportion of the composition, typically up to 30 weight % of the solutes. Alternatively, the compound of Formula I may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavorings and flavor enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming. Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al., *Pharmaceutical Technology On-line*, 25(2), 1-14 (2001). The use of chewing gum to achieve controlled release is described in WO 00/35298.

The compounds of the invention (including pharmaceutically acceptable salts thereof and N-oxides thereof) may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (for example to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of Formula I used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(DL-lactic-coglycolic acid) (PLGA) microspheres.

The compounds of the invention (including pharmaceutically acceptable salts thereof and N-oxides thereof) may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated. See e.g., Finnin and Morgan, *J. Pharm. Sci.* 1999, 88, 955-958.

Other means of topical administration include delivery by electroporation, iontophoresis, phonophoresis, sonophoresis and microneedle or needle-free (e.g., Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention (including pharmaceutically acceptable salts thereof and N-oxides thereof) can also be administered intranasally or by inhalation, typically in the form of a dry powder (either alone; as a mixture, for example, in a dry blend with lactose; or as a mixed component particle, for example, mixed with phospholipids, such as phosphatidylcholine) from a dry powder inhaler, as an aerosol spray from a pressurized container, pump, spray, atomizer (for example an atomizer using electrohydrodynamics to produce a fine mist), or nebulizer, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or hydroxypropyl methyl cellulose), blisters and cartridges for use in an inhaler or insufflator may be formulated to contain a powder mix of the compound of the invention, a suitable powder base such as lactose or starch and a performance modifier such as L-leucine, mannitol, or magnesium stearate. The lactose may be anhydrous or in the form of the monohydrate. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation may comprise a compound of Formula I or a pharmaceutically acceptable salt thereof, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.01 to 100 mg of the compound of Formula I. The overall daily dose will typically be in the range 1 µg to 200 mg, which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronized suspension or solution in isotonic, pH-adjusted, sterile saline. Other formulations suitable for ocular and aural administration include ointments, gels, biodegradable (e.g., absorbable gel sponges, collagen) and non-biodegradable (e.g., silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropyl methyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e., as a carrier, diluent, or solubilizer. Most commonly used for these purposes are alpha-, beta- and gamma-cyclodextrins, examples of which may be found in International Patent Applications Nos. WO 91/11172, WO 94/02518 and WO 98/55148.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I a prodrug thereof or a salt of such compound or prodrug and a second compound as described above. The kit comprises means for containing the separate compositions such as a container, a divided bottle or a divided foil packet. Typically the kit comprises directions for the administration of the separate components. The kit form is particularly advantageous when the separate components are for example administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. In some embodiments, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. For example, the dispenser is equipped with a memory aid, so as to further facilitate compliance with the regimen. An example of such a memory aid is a mechanical counter which indicates the number of daily doses that has been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results. In the following Examples and Preparations, "DMSO" means dimethyl sulfoxide, "N" where referring to concentration means Normal, "M" means molar, "mL" means milliliter, "mmol" means millimoles, "µmol" means micromoles, "eq." means equivalent, "° C." means degrees Celsius, "MHz" means megahertz, "HPLC" means high-performance liquid chromatography.

EXAMPLES

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate atropisomers (or atropenantiomers) of certain compounds of the invention (in some examples, the separated atropisomers are designated as ENT-1 and ENT-2, according to their order of elution). In some examples, the optical rotation of an atropisomer was measured using a polarimeter. According to its observed rotation data (or its specific rotation data), an atropisomer (or atropenantiomer) with a clockwise rotation was designated as the (+)-atropisomer [or the (+) atropenantiomer] and an atropisomer (or atropenantiomer) with a counter-clockwise rotation was designated as the (−)-atropisomer [or the (−) atropenantiomer].

For syntheses referencing procedures in other Examples or Methods, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluents/gradients were chosen to provide appropriate $R_f$s or retention times.

PREPARATIONS

Preparations P1-P8 describe preparations of some starting materials or intermediates used for preparation of certain compounds of the invention.

Preparation P1

4-Chloro-1-{[2-(trimethylsilyl)ethoxy]methyl}-1H-pyrrolo[3,2-c]pyridine (P1)

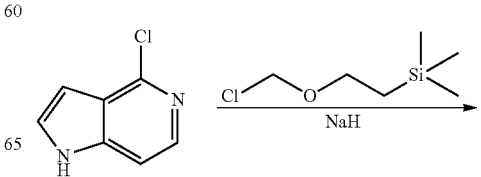

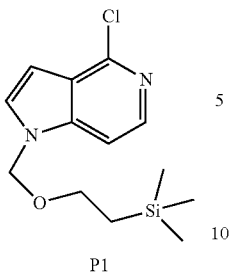

P1

A mixture of 4-chloro-1H-pyrrolo[3,2-c]pyridine (98%, 2.0 g, 13 mmol) and tetrahydrofuran (20 mL) was cooled to 0° C. Sodium hydride (60% in oil, 1.03 g, 25.8 mmol) was added portion-wise over 5 minutes, and the reaction mixture was allowed to stir at 0° C. for 10 minutes. 2-(Trimethylsilyl)ethoxymethyl chloride (3.40 mL, 19.3 mmol) was then added drop-wise over 5 minutes, and stirring was continued at 0° C. for 15 minutes. The reaction mixture was quenched with saturated aqueous ammonium chloride solution; the aqueous layer was extracted twice with ethyl acetate, and the combined organic layers were dried over sodium sulfate, filtered, and concentrated in vacuo. Silica gel chromatography (Gradient: 10% to 20% ethyl acetate in heptane) afforded the product as a colorless oil. Yield: 2.64 g, 9.33 mmol, 72%. LCMS m/z 283.0 [M+H$^+$]. $^1$H NMR (400 MHz, CDCl$_3$) δ 8.13 (d, J=5.8 Hz, 1H), 7.34 (dd, J=5.8, 0.7 Hz, 1H), 7.25 (d, J=3.3 Hz, 1H), 6.69 (dd, J=3.3, 0.7 Hz, 1H), 5.48 (s, 2H), 3.46 (dd, J=8.2, 8.1 Hz, 2H), 0.89 (dd, J=8.2, 8.1 Hz, 2H), −0.05 (s, 9H).

Preparation P2 tert-Butyl 4-chloro-1H-pyrrolo[3,2-c]pyridine-1-carboxylate (P2)

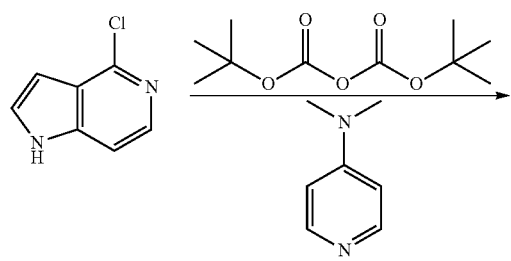

P2

Di-tert-butyl dicarbonate (99%, 650 mg, 2.95 mmol) was added to a solution of 4-chloro-1H-pyrrolo[3,2-c]pyridine (300 mg, 1.97 mmol) and 4-(dimethylamino)pyridine (97%, 124 mg, 0.984 mmol) in acetonitrile (3 mL), and the reaction mixture was stirred at room temperature for 18 hours. Volatiles were removed in vacuo, and the residue was purified via chromatography on silica gel (Gradient: 0% to 50% ethyl acetate in heptane) to afford the product as a white solid. Yield: 410 mg, 1.62 mmol, 82%. LCMS m/z 253.0 [M+H$^+$]. $^1$H NMR (400 MHz, CDCl$_3$) δ 8.24 (d, J=5.7 Hz, 1H), 7.95 (br d, J=5.7 Hz, 1H), 7.65 (d, J=3.7 Hz, 1H), 6.72 (dd, J=3.7, 0.8 Hz, 1H), 1.70 (s, 9H).

Preparation P3

4-Chloro-1-(tetrahydro-2H-pyran-2-yl)-1H-pyrazolo[4,3-c]pyridine (P3)

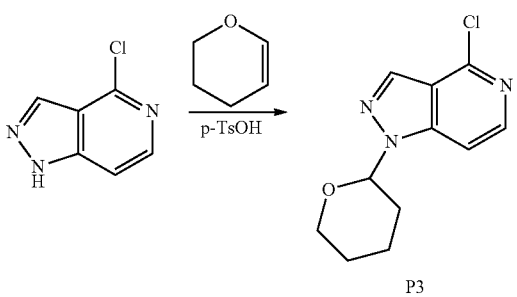

P3 p-Toluenesulfonic acid monohydrate (2.4 g, 13 mmol) and 3,4-dihydro-2H-pyran (99%, 45 mL, 520 mmol) were sequentially added to a suspension of 4-chloro-1H-pyrazolo[4,3-c]pyridine (20.0 g, 130 mmol) in dichloromethane (400 mL). The reaction mixture was allowed to stir at room temperature for 24 hours, at which time it was washed with saturated aqueous sodium bicarbonate solution. The organic layer was dried over sodium sulfate, filtered, and concentrated in vacuo. Purification via silica gel chromatography (Eluents: 10%, then 30%, then 50% ethyl acetate in heptane) afforded the product as a white solid. Yield: 27.51 g, 115.7 mmol, 89%. LCMS m/z 238.1 [M+H$^+$]. $^1$H NMR (400 MHz, CDCl$_3$) δ 8.19 (d, J=6.0 Hz, 1H), 8.16 (d, J=0.9 Hz, 1H), 7.47 (dd, J=6.0, 0.9 Hz, 1H), 5.73 (br dd, J=9.0, 2.7 Hz, 1H), 3.97-4.04 (m, 1H), 3.72-3.80 (m, 1H), 2.43-2.53 (m, 1H), 2.07-2.20 (m, 2H), 1.65-1.85 (m, 3H).

Preparation P4

4-Chloro-6-methyl-1-(tetrahydro-2H-pyran-2-yl)-1H-pyrazolo[4,3-c]pyridine (P4)

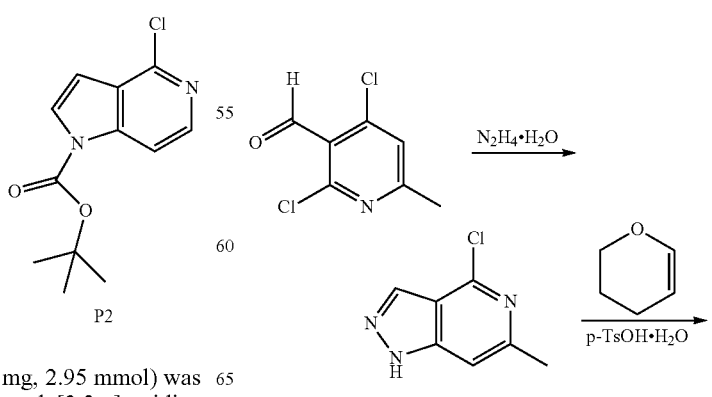

C1

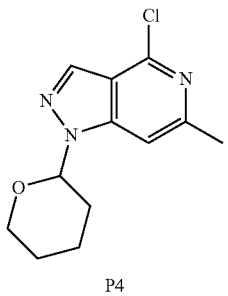

P4

Step 1. Synthesis of 4-chloro-6-methyl-1H-pyrazolo[4,3-c]pyridine (C1)

To a solution of 2,4-dichloro-6-methylpyridine-3-carbaldehyde (12 g, 63 mmol) in 1,2-dichloroethane (200 mL) was added hydrazine monohydrate (9.52 g, 0.190 mol), and the reaction mixture was heated at 80° C. for 18 hours. After removal of solvents in vacuo, the residue was suspended in water (150 mL) and stirred for 30 minutes. The resulting precipitate was collected by filtration and washed with petroleum ether (2×250 mL), then was suspended in chloroform (150 mL), stirred for 30 minutes and filtered. The chloroform suspension was repeated twice to afford the product as a white solid. Yield: 6.7 g, 40 mmol, 63%. LCMS m/z 168.1 [M+H+].
$^1$H NMR (400 MHz, DMSO-$d_6$) δ 13.70 (br s, 1H), 8.21 (s, 1H), 7.38 (s, 1H), 2.52 (s, 3H).

Step 2. Synthesis of P4 p-Toluenesulfonic acid monohydrate (29 mg, 0.15 mmol) and 3,4-dihydro-2H-pyran (99%, 205 μL, 2.39 mmol) were sequentially added to a suspension of C1 (250 mg, 1.49 mmol) and 4 Å molecular sieves in dichloromethane (10 mL). The reaction mixture was allowed to stir at room temperature for 4 hours, at which time it was filtered, concentrated in vacuo, and washed three times with heptane. Purification via silica gel chromatography (Gradient: 20% to 50% ethyl acetate in heptane) afforded the product as a colorless oil. Yield: 65 mg, 0.26 mmol, 17%. LCMS m/z 252.1 [M+H+]. $^1$H NMR (400 MHz, CDCl$_3$), characteristic peaks: δ 8.08 (d, J=0.9 Hz, 1H), 7.26-7.27 (m, 1H), 5.67 (dd, J=9.1, 2.8 Hz, 1H), 3.99-4.05 (m, 1H), 3.71-3.79 (m, 1H), 2.65 (d, J=0.8 Hz, 3H), 2.06-2.2 (m, 2H).

Preparation P5

4-Chloro-7-methoxy-1-(tetrahydro-2H-pyran-2-yl)-1H-pyrazolo[4,3-c]pyridine (P5)

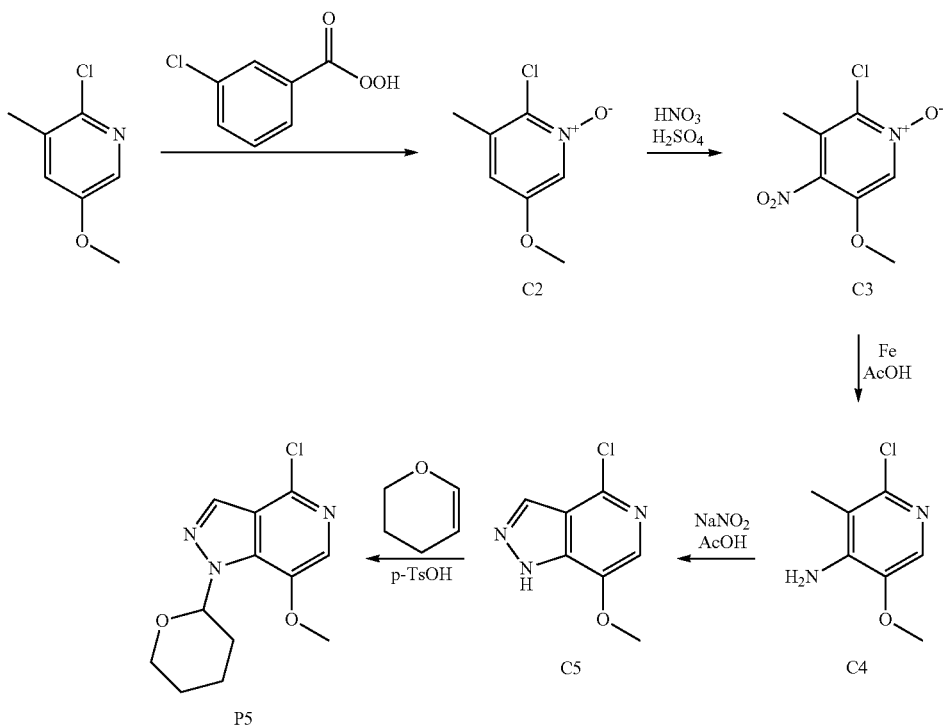

Step 1. Synthesis of 2-chloro-5-methoxy-3-methylpyridine 1-oxide (C2)

3-Chloroperoxybenzoic acid (70%, 695 mg, 2.82 mmol) was added to a solution of 2-chloro-5-methoxy-3-methylpyridine (370 mg, 2.35 mmol) in dichloromethane (10 mL). After stirring for 18 hours at room temperature, the reaction mixture was concentrated in vacuo and purified via silica gel chromatography (Gradient: 0% to 10% methanol in ethyl acetate) to afford the product as a white solid. Yield: 370 mg, 2.13 mmol, 91%. $^1$H NMR (400 MHz, CD$_3$OD) δ 8.14 (d, J=2.5 Hz, 1H), 7.23 (d, J=2.3 Hz, 1H), 3.88 (s, 3H), 2.44 (s, 3H).

Step 2. Synthesis of 2-chloro-5-methoxy-3-methyl-4-nitropyridine 1-oxide (C3)

Concentrated nitric acid (2.5 mL) was added drop-wise to a 0° C. solution of C2 (350 mg, 2.02 mmol) in concentrated sulfuric acid (2.5 mL). The reaction mixture was heated at 90° C. for 1 hour, then cooled to room temperature and poured onto crushed ice. The resulting mixture was neutralized to pH 6-7 with saturated aqueous sodium carbonate solution, and extracted with ethyl acetate. The combined organic layers were washed with water, washed with saturated aqueous sodium chloride solution, dried over magnesium sulfate, filtered, and concentrated in vacuo to provide the product as a light yellow solid. Yield: 370 mg, 1.69 mmol, 84%. LCMS m/z 219.0, 221.1 [M+H+]. $^1$H NMR (400 MHz, DMSO-$d_6$) δ 8.65 (s, 1H), 3.94 (s, 3H), 2.31 (s, 3H).

Step 3. Synthesis of 2-chloro-5-methoxy-3-methylpyridin-4-amine (C4)

Iron powder (700 mg, 12 mmol) was added to a solution of C3 (350 mg, 1.60 mmol) in acetic acid (8 mL), and the reaction mixture was heated at 100° C. for 1 hour, then cooled to room temperature. After filtration through Celite and thorough washing of the filter pad with ethyl acetate and methanol, the combined filtrates were concentrated in vacuo. The residue was diluted with saturated aqueous sodium bicarbonate solution and extracted with ethyl acetate. The combined organic layers were washed with water, washed with saturated aqueous sodium chloride solution, dried over magnesium sulfate, filtered, and concentrated under reduced pressure. Silica gel chromatography (Gradient: 50% to 75% ethyl acetate in heptane) afforded the product as a white solid. Yield: 240 mg, 1.39 mmol, 87%. LCMS m/z 173.0 [M+H+]. $^1$H NMR (400 MHz, CDCl$_3$) δ 7.65 (s, 1H), 4.38 (br s, 2H), 3.91 (s, 3H), 2.20 (s, 3H).

Step 4. Synthesis of 4-chloro-7-methoxy-1H-pyrazolo[4,3-c]pyridine (C5)

A solution of sodium nitrite (98%, 326 mg, 4.63 mmol) in water (0.6 mL) was added to a solution of C4 (200 mg, 1.16 mmol) in acetic acid (8 mL), and the reaction mixture was heated at 75° C. for 1 hour. After the reaction mixture had cooled to room temperature, it was concentrated in vacuo, diluted with saturated aqueous sodium bicarbonate solution, and extracted with ethyl acetate. The combined organic layers were washed with saturated aqueous sodium chloride solution, dried over magnesium sulfate, filtered, and concentrated under reduced pressure. Silica gel chromatography (Gradient: 25% to 50% ethyl acetate in heptane) provided the product as a yellow solid. Yield: 140 mg, 0.763 mmol, 66%. LCMS m/z 184.0 [M+H+]. $^1$H NMR (400 MHz, CDCl$_3$) δ 8.17 (s, 1H), 7.74 (s, 1H), 4.06 (s, 3H).

Step 5. Synthesis of P5

C5 was converted to the product using the method described for synthesis of 4-chloro-1-(tetrahydro-2H-pyran-2-yl)-1H-pyrazolo[4,3-c]pyridine P3 in Preparation P3. The product was obtained as a light yellow oil, which solidified upon standing. Yield: 120 mg, 0.448 mmol, 41%. LCMS m/z 268.1 [M+H+]. $^1$H NMR (400 MHz, CDCl$_3$) δ 8.11-8.12 (m, 1H), 7.72 (s, 1H), 6.12 (dd, J=10.0, 2.6 Hz, 1H), 4.06 (s, 3H), 4.04-4.10 (m, 1H), 3.69-3.77 (m, 1H), 2.51-2.62 (m, 1H), 2.12-2.21 (m, 1H), 2.00-2.08 (m, 1H), 1.5-1.8 (m, 3H).

Preparation P6

4-Chloro-1-{[2-(trimethylsilyl)ethoxy]methyl}-1H-pyrazolo[4,3-c]pyridine (P6)

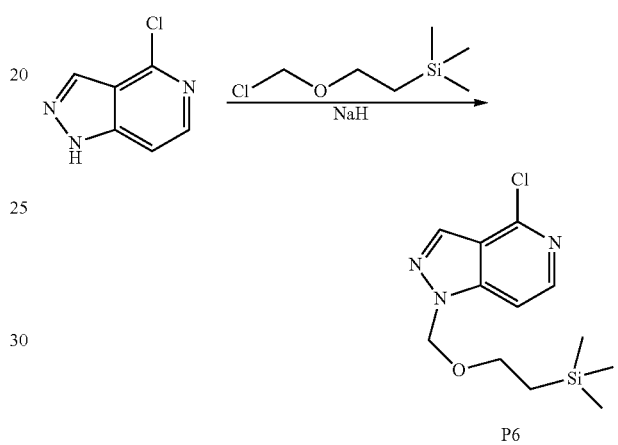

P6

4-Chloro-1H-pyrazolo[4,3-c]pyridine was converted to the product using the method described for synthesis of P1 in Preparation P1. The product was isolated as a white solid. Yield: 686 mg, 2.42 mmol, 50%. $^1$H NMR (400 MHz, CDCl$_3$) δ 8.24 (d, J=5.8 Hz, 1H), 8.17 (s, 1H), 7.43 (d, J=5.8 Hz, 1H), 5.74 (s, 2H), 3.54-3.60 (m, 2H), 0.86-0.92 (m, 2H), −0.05 (s, 9H).

Preparation P7

4-Chloro-1-{[2-(trimethylsilyl)ethoxy]methyl}-1H-pyrrolo[3,2-c]pyridine-3-carbonitrile (P7)

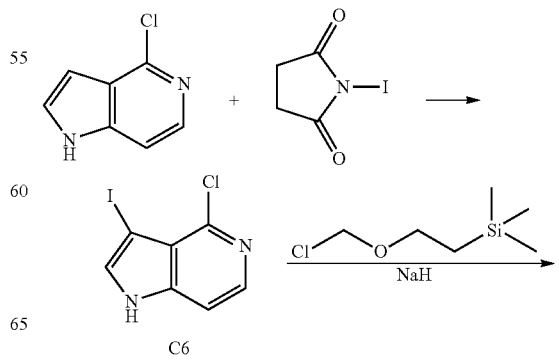

C6

-continued

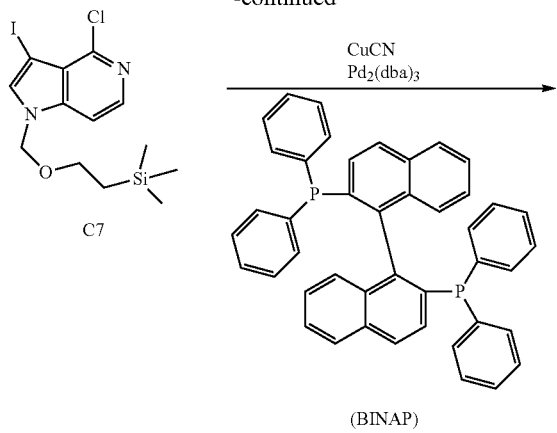

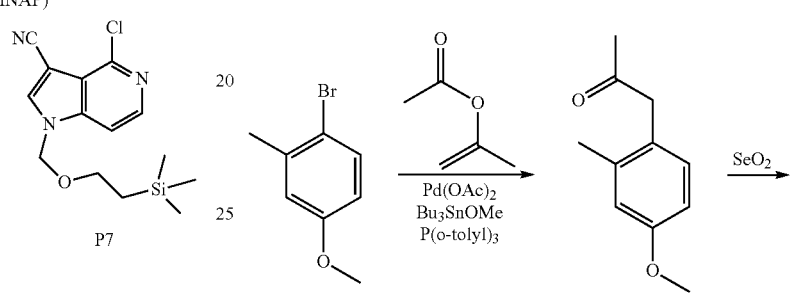

tris(dibenzylideneacetone)dipalladium(0) (275 mg, 0.300 mmol) and 1,1'-binaphthalene-2,2'-diylbis(diphenylphosphane) (BINAP, 540 mg, 0.87 mmol). After the reaction mixture had been stirred at 110° C. for 18 hours, it was filtered and concentrated under reduced pressure. Purification via silica gel chromatography (Gradient: 5% to 20% ethyl acetate in petroleum ether) afforded the product as a yellow solid. Yield: 380 mg, 1.2 mmol, 41%. $^1$H NMR (400 MHz, CDCl$_3$) δ 8.27 (d, J=5.8 Hz, 1H), 7.80 (s, 1H), 7.43 (d, J=5.8 Hz, 1H), 5.52 (s, 2H), 3.47-3.54 (m, 2H), 0.88-0.95 (m, 2H), −0.02 (s, 9H).

Preparation P8

6-(4-Hydroxy-2-methylphenyl)-1,5-dimethylpyrazin-2(1H)-one (P8)

Step 1. Synthesis of 4-chloro-3-iodo-1H-pyrrolo[3,2-c]pyridine (C6)

N-Iodosuccinimide (1.3 g, 5.8 mmol) was added to a 0° C. solution of 4-chloro-1H-pyrrolo[3,2-c]pyridine (0.60 g, 3.9 mmol) in N,N-dimethylformamide (10 mL). The reaction mixture was stirred at room temperature for 18 hours, whereupon it was concentrated in vacuo. Purification via silica gel chromatography (0% to 50% ethyl acetate in petroleum ether) afforded the product as a yellow solid. Yield: 900 mg, 3.2 mmol, 82%. $^1$H NMR (400 MHz, CDCl$_3$) δ 8.10 (d, J=5.5 Hz, 1H), 7.42 (d, J=2.5 Hz, 1H), 7.34 (d, J=5.8 Hz, 1H).

Step 2. Synthesis of 4-chloro-3-iodo-1-{[2-(trimethylsilyl)ethoxy]methyl}-1H-pyrrolo[3,2-c]pyridine (C7)

To a 0° C. solution of C6 (900 mg, 3.2 mmol) in N,N-dimethylformamide (3 mL) and tetrahydrofuran (70 mL) was added sodium hydride (60% in mineral oil, 168 mg, 4.2 mmol). After 5 minutes, 2-(trimethylsilyl)ethoxymethyl chloride (592 mg, 3.55 mmol) was added to the cold mixture. The reaction mixture was stirred at room temperature for 3 hours, then cooled to 0° C. and treated with additional sodium hydride (56 mg, 1.4 mmol) and 2-(trimethylsilyl)ethoxymethyl chloride (197 mg, 1.18 mmol). After stirring at room temperature for 18 hours, the reaction mixture was diluted with saturated aqueous sodium chloride solution (100 mL) and extracted with ethyl acetate (2×100 mL). The combined organic layers were dried, filtered, and concentrated in vacuo. Silica gel chromatography (Gradient: 0% to 30% ethyl acetate in petroleum ether) provided the product as a yellow oil. Yield: 650 mg, 1.59 mmol, 50%. $^1$H NMR (400 MHz, CDCl$_3$) δ 8.14 (d, J=6.0 Hz, 1H), 7.39 (d, J=6.0 Hz, 1H), 7.38 (s, 1H), 5.44 (s, 2H), 3.44-3.50 (m, 2H), 0.86-0.92 (m, 2H), −0.03 (s, 9H).

Step 3. Synthesis of P7

To a mixture of C7 (1.2 g, 2.9 mmol) and copper(I) cyanide (540 mg, 6.0 mmol) in 1,4-dioxane (40 mL) were added

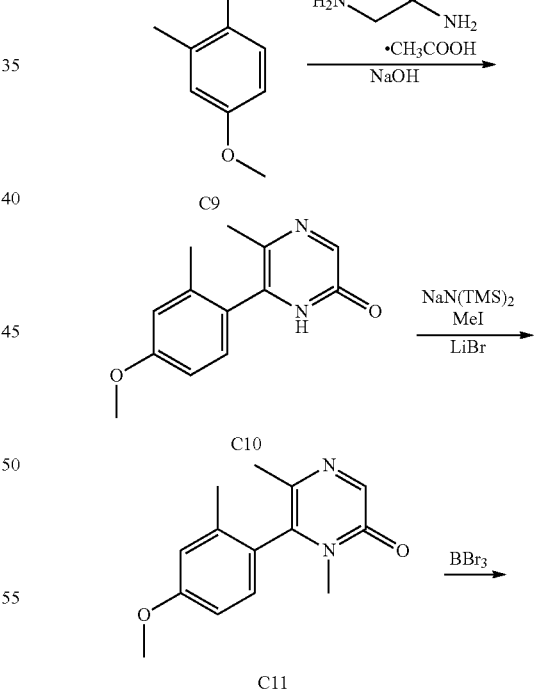

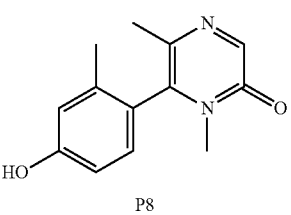

Step 1. Synthesis of 1-(4-methoxy-2-methylphenyl)propan-2-one (C8)

Four batches of this experiment were carried out (4×250 g substrate). Tributyl(methoxy)stannane (400 g, 1.24 mol), 1-bromo-4-methoxy-2-methylbenzene (250 g, 1.24 mol), prop-1-en-2-yl acetate (187 g, 1.87 mol), palladium(II) acetate (7.5 g, 33 mmol) and tris(2-methylphenyl)phosphane (10 g, 33 mmol) were stirred together in toluene (2 L) at 100° C. for 18 hours. After cooling to room temperature, the reaction mixture was treated with aqueous potassium fluoride solution (4 M, 400 mL) and stirred for 2 hours at 40° C. The resulting mixture was diluted with toluene (500 mL) and filtered through Celite; the filter pad was thoroughly washed with ethyl acetate (2×1.5 L). The organic phase from the combined filtrates was dried over sodium sulfate, filtered, and concentrated in vacuo. Purification via silica gel chromatography (Gradient: 0% to 5% ethyl acetate in petroleum ether) provided the product as a yellow oil. Combined yield: 602 g, 3.38 mol, 68%. LCMS m/z 179.0 [M+H$^+$]. $^1$H NMR (400 MHz, CDCl$_3$) δ 7.05 (d, J=8.3 Hz, 1H), 6.70-6.77 (m, 2H), 3.79 (s, 3H), 3.65 (s, 2H), 2.22 (s, 3H), 2.14 (s, 3H).

Step 2. Synthesis of 1-(4-methoxy-2-methylphenyl)propane-1,2-dione (C9)

C8 (6.00 g, 33.7 mmol) and selenium dioxide (7.47 g, 67.3 mmol) were suspended in 1,4-dioxane (50 mL) and heated at 100° C. for 18 hours. The reaction mixture was cooled to room temperature and filtered through Celite; the filtrate was concentrated in vacuo. Silica gel chromatography (Eluent: 10% ethyl acetate in heptane) afforded the product as a bright yellow oil. Yield: 2.55 g, 13.3 mmol, 39%. LCMS m/z 193.1 [M+H$^+$]. $^1$H NMR (400 MHz, CDCl$_3$) δ 7.66 (d, J=8.6 Hz, 1H), 6.81 (br d, half of AB quartet, J=2.5 Hz, 1H), 6.78 (br dd, half of ABX pattern, J=8.7, 2.6 Hz, 1H), 3.87 (s, 3H), 2.60 (br s, 3H), 2.51 (s, 3H).

Step 3. Synthesis of 6-(4-methoxy-2-methylphenyl)-5-methylpyrazin-2(1H)-one (C10)

C9 (4.0 g, 21 mmol) and glycinamide acetate (2.79 g, 20.8 mmol) were dissolved in methanol (40 mL) and cooled to −10° C. Aqueous sodium hydroxide solution (12 N, 3.5 mL, 42 mmol) was added, and the resulting mixture was slowly warmed to room temperature. After stirring for 3 days, the reaction mixture was concentrated in vacuo. The residue was diluted with water, and 1 N aqueous hydrochloric acid was added until the pH was approximately 7. The aqueous phase was extracted with ethyl acetate, and the combined organic extracts were washed with saturated aqueous sodium chloride solution, dried over magnesium sulfate, filtered, and concentrated under reduced pressure. The resulting residue was slurried with 3:1 ethyl acetate/heptane, stirred for 5 minutes, filtered, and concentrated in vacuo. Silica gel chromatography (Eluent: ethyl acetate) provided the product as a tan solid that contained 15% of an undesired regioisomer; this material was used without further purification. Yield: 2.0 g. LCMS m/z 231.1 [M+H$^+$]. $^1$H NMR (400 MHz, CDCl$_3$) δ 8.09 (s, 1H), 7.14 (d, J=8.2 Hz, 1H), 6.82-6.87 (m, 2H), 3.86 (s, 3H), 2.20 (s, 3H), 2.11 (s, 3H).

Step 4. Synthesis of 6-(4-methoxy-2-methylphenyl)-1,5-dimethylpyrazin-2(1H)-one (C11)

C10 (from the previous step, 1.9 g) was dissolved in N,N-dimethylformamide (40 mL). Lithium bromide (0.86 g, 9.9 mmol) and sodium bis(trimethylsilyl)amide (95%, 1.91 g, 9.89 mmol) were added, and the resulting solution was stirred for 30 minutes. Methyl iodide (0.635 mL, 10.2 mmol) was added and stirring was continued at room temperature for 18 hours. The reaction mixture was then diluted with water and brought to a pH of approximately 7 by slow portion-wise addition of 1 N aqueous hydrochloric acid. The aqueous layer was extracted with ethyl acetate and the combined organic layers were washed several times with water, dried over magnesium sulfate, filtered, and concentrated. Silica gel chromatography (Gradient: 75% to 100% ethyl acetate in heptane) afforded the product as a viscous orange oil. Yield: 1.67 g, 6.84 mmol, 33% over two steps. LCMS m/z 245.1 [M+H$^+$]. $^1$H NMR (400 MHz, CDCl$_3$) δ 8.17 (s, 1H), 7.03 (br d, J=8 Hz, 1H), 6.85-6.90 (m, 2H), 3.86 (s, 3H), 3.18 (s, 3H), 2.08 (br s, 3H), 2.00 (s, 3H).

Step 5. Synthesis of P8

To a −78° C. solution of C11 (1.8 g, 7.37 mmol) in dichloromethane (40 mL) was added a solution of boron tribromide in dichloromethane (1 M, 22 mL, 22 mmol). The cooling bath was removed after 30 minutes, and the reaction mixture was allowed to warm to room temperature and stir for 18 hours. The reaction was cooled to −78° C., and methanol (10 mL) was slowly added; the resulting mixture was slowly warmed to room temperature. The reaction mixture was concentrated in vacuo, methanol (20 mL) was added, and the mixture was again concentrated under reduced pressure. The residue was diluted with ethyl acetate (300 mL) and water (200 mL) and the aqueous layer was brought to pH 7 via portion-wise addition of saturated aqueous sodium carbonate solution. The mixture was extracted with ethyl acetate (3×200 mL). The combined organic extracts were washed with water and with saturated aqueous sodium chloride solution, dried over magnesium sulfate, filtered, and concentrated in vacuo to afford the product as a light tan solid. Yield: 1.4 g, 6.0 mmol, 81%. LCMS m/z 231.1 [M+H$^+$]. $^1$H NMR (400 MHz, CDCl$_3$) δ 8.21 (s, 1H), 6.98 (d, J=8.2 Hz, 1H), 6.87-6.89 (m, 1H), 6.85 (br dd, J=8.2, 2.5 Hz, 1H), 3.22 (s, 3H), 2.06 (br s, 3H), 2.03 (s, 3H).

Example 1

4-[4-(4,6-Dimethylpyrimidin-5-yl)-3-fluorophenoxy]-1H-pyrrolo[3,2-c]pyridine (1)

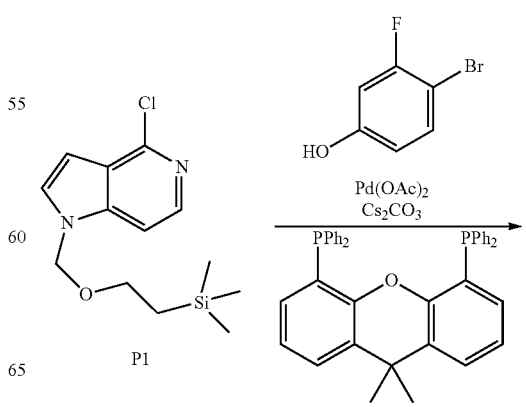

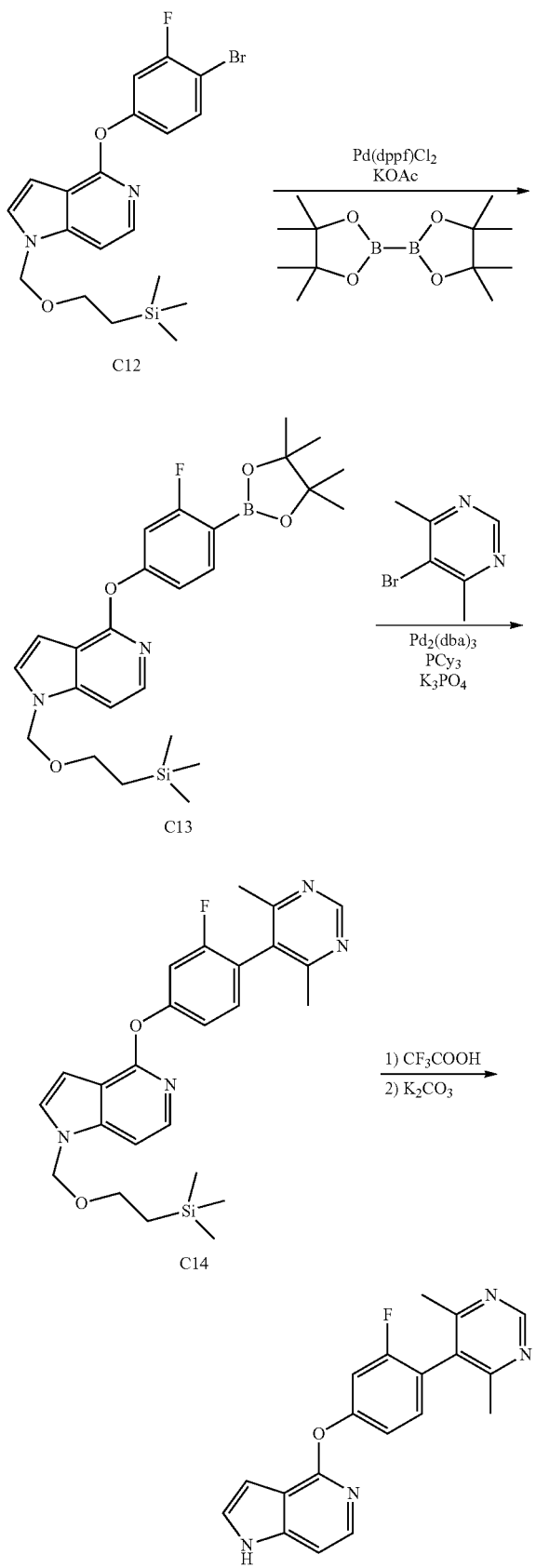

Step 1. Synthesis of 4-(4-bromo-3-fluorophenoxy)-1-{[2-(trimethylsilyl)ethoxy]methyl}-1H-pyrrolo[3,2-c]pyridine (C12)

A mixture of P1 (2.9 g, 10 mmol), 4-bromo-3-fluorophenol (3.4 g, 18 mmol), palladium(II) acetate (168 mg, 0.748 mmol), 4,5-bis(diphenylphosphino)-9,9-dimethylxanthene (Xantphos, 0.87 g, 1.5 mmol) and cesium carbonate (9.8 g, 30 mmol) in 1,4-dioxane (60 mL) was stirred at 120° C. for 4 hours. The mixture was filtered, the filtrate was concentrated in vacuo, and the residue was purified by silica gel chromatography (Eluent: 10:1 petroleum ether/ethyl acetate) to provide the product as a colorless oil. Yield: 1.6 g, 3.7 mmol, 37%. $^1$H NMR (400 MHz, CDCl$_3$) δ 7.90 (d, J=5.8 Hz, 1H), 7.55 (dd, J=8.5, 8.0 Hz, 1H), 7.17-7.21 (m, 2H), 7.08 (dd, J=9.4, 2.6 Hz, 1H), 6.94-6.99 (m, 1H), 6.68 (d, J=3.3 Hz, 1H), 5.49 (s, 2H), 3.50 (t, J=8.0 Hz, 2H), 0.91 (t, J=8.1 Hz, 2H), −0.04 (s, 9H).

Step 2. Synthesis of 4-[3-fluoro-4-(4,4,5,5-tetramethyl-1,3,2-dioxaborolan-2-yl)phenoxy]-1-{[2-(trimethylsilyl)ethoxy]methyl}-1H-pyrrolo[3,2-c]pyridine (C13)

A mixture of C12 (1.2 g, 2.7 mmol), 4,4,4',4',5,5,5',5'-octamethyl-2,2'-bi-1,3,2-dioxaborolane (1.38 g, 5.43 mmol), potassium acetate (0.8 g, 8 mmol) and [1,1'-bis(diphenylphosphino)ferrocene]dichloropalladium(II) (150 mg, 0.20 mmol) in 1,4-dioxane (20 mL) was stirred at 120° C. for 5 hours. After completion of the reaction, the mixture was filtered and the filtrate was concentrated under reduced pressure. Purification using silica gel chromatography (Eluent: 15:1 petroleum ether/ethyl acetate) afforded the product as an orange oil. Yield: 0.94 g, 1.9 mmol, 70%. $^1$H NMR (400 MHz, CDCl$_3$) δ 7.92 (d, J=5.8 Hz, 1H), 7.77 (dd, J=7.9, 7.2 Hz, 1H), 7.19 (d, J=5.9 Hz, 1H), 7.17 (d, J=3.3 Hz, 1H), 6.99-7.03 (m, 1H), 6.90-6.94 (m, 1H), 6.62 (d, J=3.3 Hz, 1H), 5.49 (s, 2H), 3.49 (t, J=8.1 Hz, 2H), 1.36 (s, 12H), 0.90 (t, J=8.2 Hz, 2H), −0.04 (s, 9H).

Step 3. Synthesis of 4-[4-(4,6-dimethylpyrimidin-5-yl)-3-fluorophenoxy]-1-{[2-(trimethylsilyl)ethoxy]methyl}-1H-pyrrolo[3,2-c]pyridine (C14)

A mixture of C13 (427 mg, 0.881 mmol), 5-bromo-4,6-dimethylpyrimidine (150 mg, 0.802 mmol), tris(dibenzylideneacetone)dipalladium(0) (147 mg, 0.160 mmol), tricyclohexylphosphine (90 mg, 0.32 mmol) and potassium phosphate (341 mg, 1.61 mmol) in 1,4-dioxane (4 mL) containing 5 drops of water was heated at 120° C. for 2 hours under microwave irradiation. The mixture was filtered, the filtrate was concentrated under reduced pressure, and the residue was purified by preparative thin layer chromatography on silica gel (Eluent: ethyl acetate) to give the product, which was used without further purification. Yield: 180 mg, 0.387 mmol, 48%. LCMS m/z 465.3 [M+H$^+$].

Step 4. Synthesis of 4-[4-(4,6-dimethylpyrimidin-5-yl)-3-fluorophenoxy]-1H-pyrrolo[3,2-c]pyridine (1)

A solution of C14 (180 mg, 0.387 mmol) in trifluoroacetic acid (6 mL) was heated to 90° C. for 2 hours. The mixture was concentrated under reduced pressure and the residue was dissolved in acetonitrile (5 mL) and water (1 mL). Solid potassium carbonate (1 g) was added, and the mixture was refluxed for 2 hours. The suspension was filtered and the filtrate was concentrated in vacuo. Purification via preparative reversed phase high-performance liquid chromatography (Column: Phenomenex Synergi C18, 4 μm; Mobile phase A: 0.1% formic acid in water; Mobile phase B: 0.1% formic acid in acetonitrile; Gradient: 18% to 28% B) afforded the product as a white solid. Yield: 114 mg, 0.341 mmol, 88%. LCMS m/z 334.9 [M+H⁺]. ¹H NMR (400 MHz, CD₃OD) δ 8.96 (s, 1H), 8.01 (d, J=6.5 Hz, 1H), 7.67 (d, J=6.5 Hz, 1H), 7.61 (d, J=3.0 Hz, 1H), 7.47-7.58 (m, 2H), 7.41 (br d, J=8.5 Hz, 1H), 6.17 (d, J=3.0 Hz, 1H), 2.39 (s, 6H).

Example 2

4-[4-(1,4-Dimethyl-1H-pyrazol-5-yl)-3-methylphenoxy]-1H-pyrrolo[3,2-c]pyridine (2)

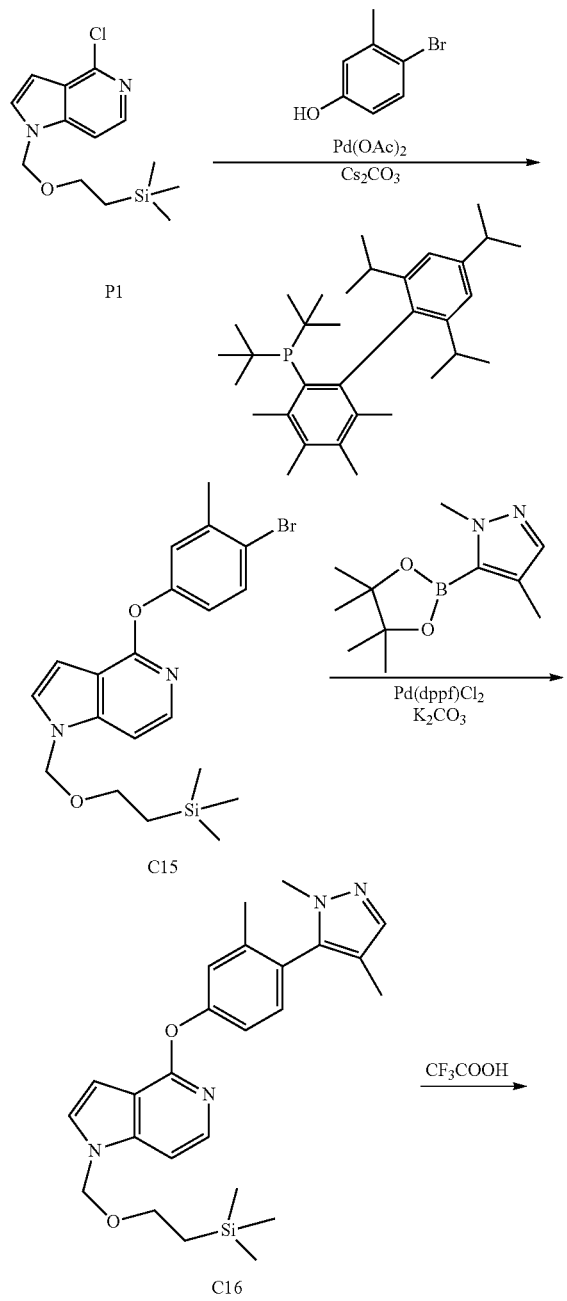

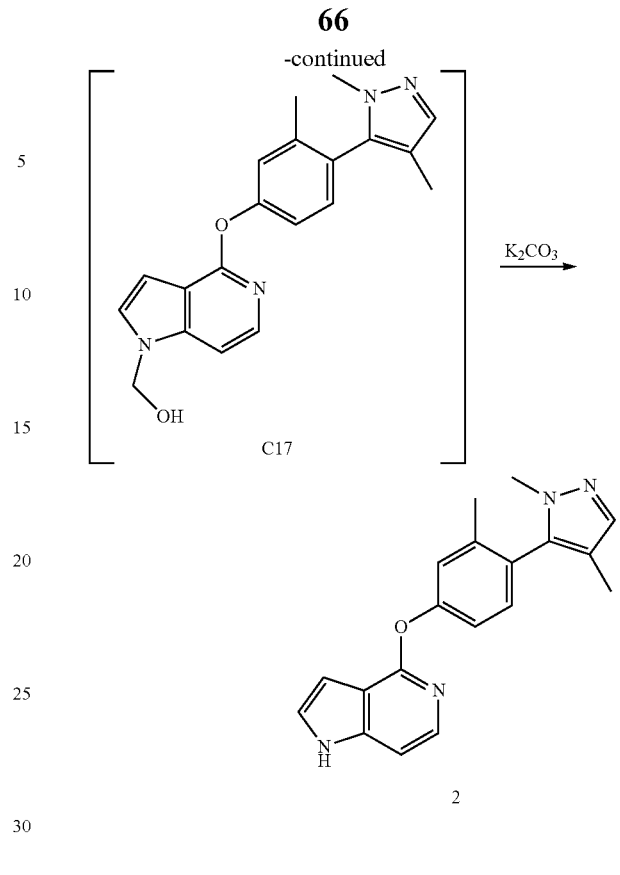

Step 1. Synthesis of 4-(4-bromo-3-methylphenoxy)-1-{[2-(trimethylsilyl)ethoxy]methyl}-1H-pyrrolo[3,2-c]pyridine (C15)

P1 (326 mg, 1.15 mmol), 4-bromo-3-methylphenol (216 mg, 1.15 mmol), di-tert-butyl[3,4,5,6-tetramethyl-2',4',6'-tri(propan-2-yl)biphenyl-2-yl]phosphane (97%, 114 mg, 0.230 mmol), palladium(II) acetate (95%, 19.1 mg, 80.8 μmol) and cesium carbonate (1.13 g, 3.47 mmol) were combined in 1,4-dioxane (7 mL) in a sealable tube, and the reaction mixture was heated at 130° C. for 18 hours. Ethyl acetate was added, and the mixture was filtered through Celite, concentrated in vacuo and purified twice via silica gel chromatography (Gradient: 0% to 50% ethyl acetate in heptane). The product was obtained as an oil that still contained some of the phenol starting material. Yield: 395 mg, <0.91 mmol, <79%. LCMS m/z 434.9 [M+H⁺]. ¹H NMR (500 MHz, CDCl₃), product peaks only: δ 7.91 (d, J=5.9 Hz, 1H), 7.52 (d, J=8.5 Hz, 1H), 7.19-7.22 (m, 2H), 7.12 (br d, J=2.7 Hz, 1H), 6.94 (br dd, J=8.7, 2.8 Hz, 1H), 6.69 (br d, J=3.2 Hz, 1H), 5.51 (s, 2H), 3.51-3.56 (m, 2H), 2.36 (s, 3H), 0.92-0.97 (m, 2H), 0.01 (s, 9H).

Step 2. Synthesis of 4-[4-(1,4-dimethyl-1H-pyrazol-5-yl)-3-methylphenoxy]-1-{[2-(trimethylsilyl)ethoxy]methyl}-1H-pyrrolo[3,2-c]pyridine (C16)

To a mixture of C15 (100 mg, 0.231 mmol), 1,4-dioxane (2 mL) and water (0.5 mL) was added 1,4-dimethyl-5-(4,4,5,5-tetramethyl-1,3,2-dioxaborolan-2-yl)-1H-pyrazole (56 mg, 0.25 mmol), [1,1'-bis(diphenylphosphino)ferrocene]dichloropalladium(II) (25.6 mg, 0.0350 mmol) and potassium carbonate (97 mg, 0.70 mmol) at room temperature. The reaction mixture was stirred at 120° C. for 1 hour; after cooling to room temperature, the mixture was filtered and the filtrate was concentrated in vacuo. Purification via preparative thin layer chromatography on silica gel (Eluent: 1:1 petroleum ether/ethyl acetate) provided the product as a red oil. Yield: 51 mg, 0.11 mmol, 48%. $^1$H NMR (400 MHz, CD$_3$OD) δ 7.80 (d, J=6.0 Hz, 1H), 7.43 (d, J=3.3 Hz, 1H), 7.37-7.40 (m, 2H), 7.21 (d, J=8.3 Hz, 1H), 7.16 (br d, J=2.0 Hz, 1H), 7.08 (br dd, J=8.3, 2.5 Hz, 1H), 6.61 (d, J=3.3 Hz, 1H), 5.60 (s, 2H), 3.61 (s, 3H), 3.51-3.57 (m, 2H), 2.09 (s, 3H), 1.91 (s, 3H), 0.85-0.91 (m, 2H), −0.06 (s, 9H).

Step 3. Synthesis of 4-[4-(1,4-dimethyl-1H-pyrazol-5-yl)-3-methylphenoxy]-1H-pyrrolo[3,2-c]pyridine (2)

A solution of C16 (51 mg, 0.11 mmol) in trifluoroacetic acid (2 mL) was stirred at 80° C. for 1 hour. After cooling to room temperature, the mixture was concentrated in vacuo to afford {4-[4-(1,4-dimethyl-1H-pyrazol-5-yl)-3-methylphenoxy]-1H-pyrrolo[3,2-c]pyridin-1-yl}methanol (C17) (38 mg, 100%), which was combined with potassium carbonate (100 mg), acetonitrile (2 mL) and water (0.3 mL). This reaction mixture was stirred at 80-85° C. for 24 hours. The reaction mixture was cooled to room temperature and concentrated under reduced pressure; purification by preparative thin layer chromatography on silica gel (Eluent: 1:3 petroleum ether/ethyl acetate) provided the product as a white solid. Yield: 16 mg, 50 μmol, 45%. LCMS m/z 318.9 [M+H$^+$]. $^1$H NMR (400 MHz, CD$_3$OD) δ 7.71 (d, J=5.5 Hz, 1H), 7.38 (s, 1H), 7.32 (d, J=3.5 Hz, 1H), 7.23 (d, J=6.0 Hz, 1H), 7.20 (d, J=8.5 Hz, 1H), 7.14 (d, J=2.5 Hz, 1H), 7.06 (dd, J=8.3, 2.3 Hz, 1H), 6.53 (d, J=3.0 Hz, 1H), 3.60 (s, 3H), 2.09 (s, 3H), 1.91 (s, 3H).

Examples 3 and 4

(+)-4,6-Dimethyl-5-[2-methyl-4-(1H-pyrazolo[4,3-c]pyridin-4-yloxy)phenyl]pyridazin-3(2H)-one (3) and
(−)-4,6-Dimethyl-5-[2-methyl-4-(1H-pyrazolo[4,3-c]pyridin-4-yloxy)phenyl]pyridazin-3(2H)-one (4)

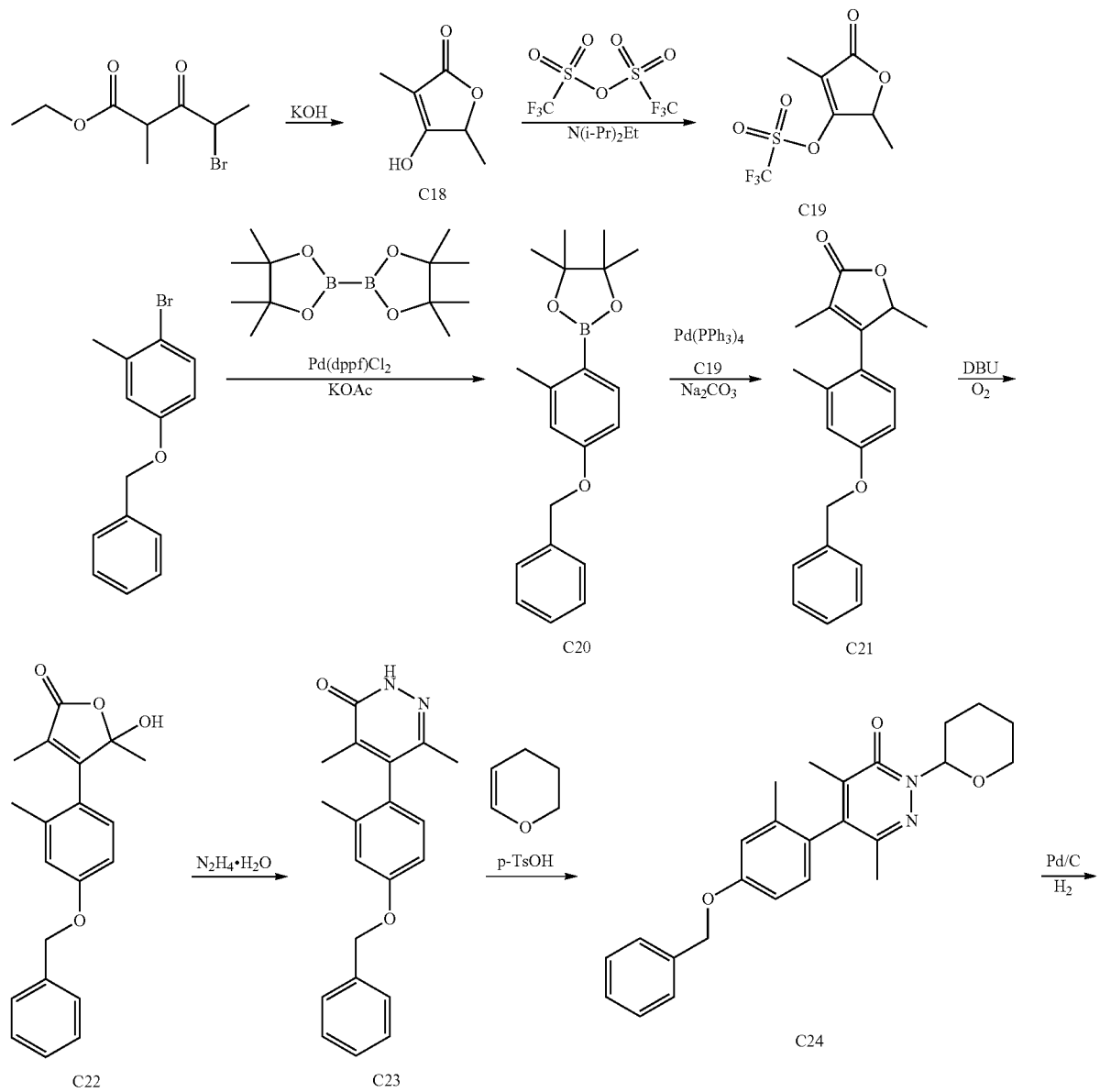

-continued
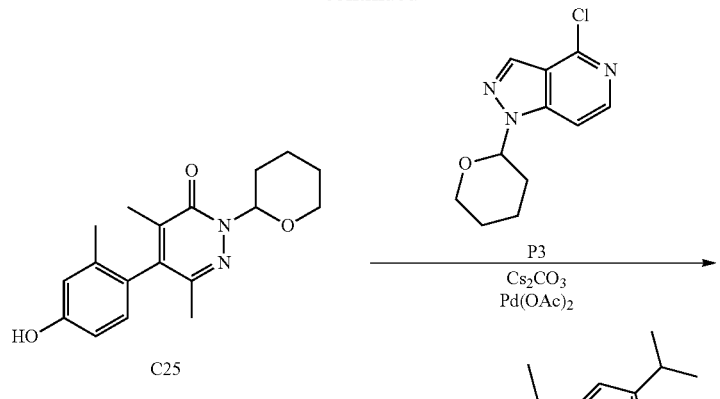
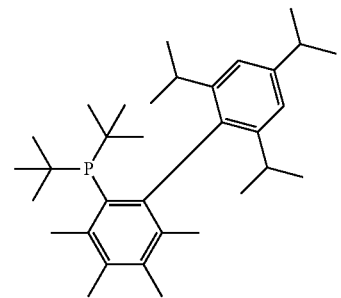
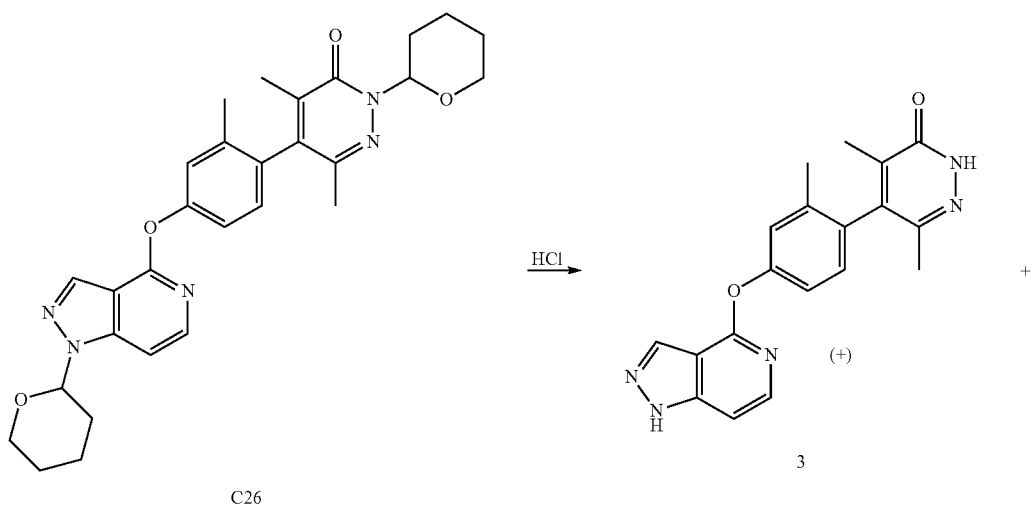
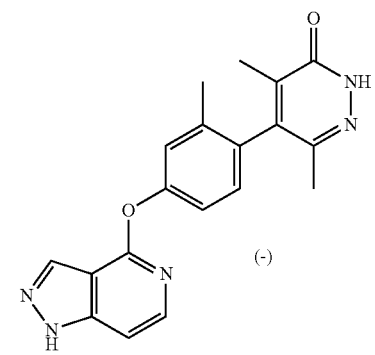

Step 1. Synthesis of 4-hydroxy-3,5-dimethylfuran-2(5H)-one (C18)

Methylation of ethyl 3-oxopentanoate according to the method of D. Kalaitzakis et al., *Tetrahedron: Asymmetry* 2007, 18, 2418-2426, afforded ethyl 2-methyl-3-oxopentanoate; subsequent treatment with 1 equivalent of bromine in chloroform provided ethyl 4-bromo-2-methyl-3-oxopentanoate. This crude material (139 g, 586 mmol) was slowly added to a 0° C. solution of potassium hydroxide (98.7 g, 1.76 mol) in water (700 mL). The internal reaction temperature rose to 30° C. during the addition. The reaction mixture was subjected to vigorous stirring for 4 hours in an ice bath, at which point it was acidified via slow addition of concentrated hydrochloric acid. After extraction with ethyl acetate, the aqueous layer was saturated with solid sodium chloride and extracted three additional times with ethyl acetate. The combined organic layers were washed with saturated aqueous sodium chloride solution, dried over magnesium sulfate, filtered, and concentrated under reduced pressure to afford a mixture of oil and solid (81.3 g). This material was suspended in chloroform (200 mL); the solids were removed via filtration and washed with chloroform (2×50 mL). The combined filtrates were concentrated in vacuo and treated with a 3:1 mixture of heptane and diethyl ether (300 mL). The mixture was vigorously swirled until some of the oil began to solidify. It was then concentrated under reduced pressure to afford an oily solid (60.2 g). After addition of a 3:1 mixture of heptane and diethyl ether (300 mL) and vigorous stirring for 10 minutes, the solid was collected by filtration to afford the product as an off-white solid. Yield: 28.0 g, 219 mmol, 37%. $^1$H NMR (400 MHz, CDCl$_3$) δ 4.84 (br q, J=6.8 Hz, 1H), 1.74 (br s, 3H), 1.50 (d, J=6.8 Hz, 3H).

Step 2. Synthesis of 2,4-dimethyl-5-oxo-2,5-dihydrofuran-3-yl trifluoromethanesulfonate (C19)

Trifluoromethanesulfonic anhydride (23.7 mL, 140 mmol) was added portion-wise to a solution of C18 (15.0 g, 117 mmol) and N,N-diisopropylethylamine (99%, 24.8 mL, 140 mmol) in dichloromethane (500 mL) at −20° C., at a rate sufficient to maintain the internal reaction temperature below −10° C. The reaction mixture was stirred at −20° C., and allowed to warm gradually to 0° C. over 5 hours. The reaction mixture was then passed through a plug of silica gel, dried over magnesium sulfate, and concentrated in vacuo. The residue was suspended in diethyl ether and filtered; the filtrate was concentrated under reduced pressure. Purification using silica gel chromatography (Gradient: 0% to 17% ethyl acetate in heptane) afforded the product as a pale yellow oil. Yield: 21.06 g, 80.94 mmol, 69%. $^1$H NMR (400 MHz, CDCl$_3$) δ 5.09-5.16 (m, 1H), 1.94-1.96 (m, 3H), 1.56 (d, J=6.6 Hz, 3H).

Step 3. Synthesis of 2-[4-(benzyloxy)-2-methylphenyl]-4,4,5,5-tetramethyl-1,3,2-dioxaborolane (C20)

Benzyl 4-bromo-3-methylphenyl ether (19 g, 69 mmol), [1,1'-bis(diphenylphosphino)ferrocene]dichloropalladium (II) (7.5 g, 10.2 mmol), potassium acetate (26.9 g, 274 mmol) and 4,4,4',4',5,5,5',5'-octamethyl-2,2'-bi-1,3,2-dioxaborolane (20 g, 79 mmol) were combined in 1,4-dioxane (500 mL) and heated at reflux for 2 hours. The reaction mixture was filtered through Celite; the filtrate was concentrated in vacuo and purified by silica gel chromatography (Gradient: 0% to 1% ethyl acetate in petroleum ether) to afford the product as a yellow gel. Yield: 15 g, 46 mmol, 67%. $^1$H NMR (400 MHz, CDCl$_3$) δ 7.73 (d, J=8.0 Hz, 1H), 7.30-7.46 (m, 5H), 6.76-6.82 (m, 2H), 5.08 (s, 2H), 2.53 (s, 3H), 1.34 (s, 12H).

Step 4. Synthesis of 4-[4-(benzyloxy)-2-methylphenyl]-3,5-dimethylfuran-2(5H)-one (C21)

C19 (5.0 g, 19 mmol), C20 (7.48 g, 23.1 mmol), tetrakis(triphenylphosphine)palladium(0) (2.22 g, 1.92 mmol) and sodium carbonate (4.07 g, 38.4 mmol) were combined in 1,4-dioxane (100 mL) and water (5 mL), and heated at reflux for 2 hours. The reaction mixture was filtered and the filtrate was concentrated in vacuo. Purification using silica gel chromatography (Eluents: 10:1, then 5:1 petroleum ether/ethyl acetate) provided the product as a white solid. Yield: 5.8 g, 19 mmol, 100%. NMR (400 MHz, CDCl$_3$) δ 7.33-7.49 (m, 5H), 6.98 (d, J=8.5 Hz, 1H), 6.94 (br d, J=2.5 Hz, 1H), 6.88 (br dd, J=8.3, 2.5 Hz, 1H), 5.20 (qq, J=6.7, 1.8 Hz, 1H), 5.09 (s, 2H), 2.21 (s, 3H), 1.78 (d, J=1.8 Hz, 3H), 1.31 (d, J=6.8 Hz, 3H).

Step 5. Synthesis of 4-[4-(benzyloxy)-2-methylphenyl]-5-hydroxy-3,5-dimethylfuran-2(5H)-one (C22)

A solution of C21 (5.4 g, 18 mmol) and 1,8-diazabicyclo[5.4.0]undec-7-ene (DBU, 13.3 g, 87.4 mmol) in acetonitrile (100 mL) was cooled to −60° C. Oxygen was bubbled into the reaction mixture for 20 minutes at −60° C.; the solution was then stirred at 50° C. for 18 hours. The reaction mixture was concentrated in vacuo and purified via silica gel chromatography (Eluent: 5:1 petroleum ether/ethyl acetate) to provide the product as a colorless oil. Yield: 3.5 g, 11 mmol, 61%. $^1$H NMR (400 MHz, CDCl$_3$), characteristic peaks: δ 7.33-7.49 (m, 5H), 6.92-6.96 (m, 1H), 6.88 (dd, J=8.5, 2.5 Hz, 1H), 5.09 (s, 2H), 2.20 (s, 3H), 1.73 (s, 3H).

Step 6. Synthesis of 5-[4-(benzyloxy)-2-methylphenyl]-4,6-dimethylpyridazin-3(2H)-one (C23)

A mixture of C22 (3.5 g, 11 mmol) and hydrazine hydrate (85% in water, 1.9 g, 32 mmol) in n-butanol (60 mL) was heated at reflux for 18 hours. After removal of volatiles under reduced pressure, the residue was stirred with ethyl acetate (20 mL) for 30 minutes, whereupon filtration provided the product as a white solid. Yield: 2.0 g, 6.2 mmol, 56%. $^1$H NMR (400 MHz, CDCl$_3$) δ 10.93 (br s, 1H), 7.33-7.51 (m, 5H), 6.96 (s, 1H), 6.88-6.94 (m, 2H), 5.10 (s, 2H), 2.04 (s, 3H), 1.95 (s, 3H), 1.91 (s, 3H).

Step 7. Synthesis of 5-[4-(benzyloxy)-2-methylphenyl]-4,6-dimethyl-2-(tetrahydro-2H-pyran-2-yl)pyridazin-3(2H)-one (C24)

A mixture of C23 (1.04 g, 3.25 mmol), 3,4-dihydro-2H-pyran (12.3 g, 1.46 mmol) and p-toluenesulfonic acid (59.4 mg, 0.652 mmol) in tetrahydrofuran (100 mL) was heated at reflux for 24 hours. The reaction mixture was then concentrated in vacuo and partitioned between ethyl acetate and water. The organic layer was dried over sodium sulfate, filtered, and concentrated under reduced pressure. Silica gel chromatography (Gradient: 0% to 40% ethyl acetate in heptane) afforded the product as a gum, presumed to be a mixture of diastereomeric atropisomers from the $^1$H NMR spectrum. Yield: 560 mg, 1.38 mmol, 42%. LCMS m/z 405.3 [M+H$^+$]. $^1$H NMR (400 MHz, CDCl$_3$), characteristic peaks: δ 7.33-7.49 (m, 5H), 6.83-6.95 (m, 3H), 6.12-6.17 (m, 1H), 5.09 (s, 2H), 4.15-4.24 (m, 1H), 3.76-3.85 (m, 1H), 2.29-2.41 (m, 1H), 2.02 and 2.04 (2 s, total 3H), 1.98 and 1.98 (2 s, total 3H), 1.89 and 1.89 (2 s, total 3H).

Step 8. Synthesis of 5-(4-hydroxy-2-methylphenyl)-4,6-dimethyl-2-(tetrahydro-2H-pyran-2-yl)pyridazin-3(2H)-one (C25)

Palladium (10% on carbon, 1.16 g, 1.09 mmol) was added to a solution of C24 (1.47 g, 3.63 mmol) in methanol (30 mL) and ethyl acetate (10 mL), and the mixture was hydrogenated (50 psi) on a Parr shaker for 18 hours at room temperature. The reaction mixture was filtered through Celite, and the filter pad was rinsed with ethyl acetate; the combined filtrates were concentrated in vacuo and triturated with heptane, affording the product as a white solid, judged to be a mixture of diastereomeric atropisomers from the $^1$H NMR spectrum. Yield: 1.01 g, 3.21 mmol, 88%. $^1$H NMR (400 MHz, CDCl$_3$), characteristic peaks: δ 6.74-6.85 (m, 3H), 6.12-6.17 (m, 1H), 4.15-4.23 (m, 1H), 3.76-3.84 (m, 1H), 2.28-2.41 (m, 1H), 1.99 and 2.01 (2 s, total 3H), 1.97 and 1.98 (2 s, total 3H), 1.89 and 1.89 (2 s, total 3H).

Step 9. Synthesis of 4,6-dimethyl-5-(2-methyl-4-{[1-(tetrahydro-2H-pyran-2-yl)-1H-pyrazolo[4,3-c]pyridin-4-yl]oxy}phenyl)-2-(tetrahydro-2H-pyran-2-yl)pyridazin-3(2H)-one (C26)

Cesium carbonate (2.06 g, 6.32 mmol) was added to a solution of P3 (550 mg, 2.31 mmol) and C25 (662 mg, 2.10 mmol) in 1,4-dioxane (40 mL). After addition of palladium (II) acetate (48 mg, 0.21 mmol), the reaction mixture was purged with nitrogen for 10 minutes. Di-tert-butyl[3,4,5,6-tetramethyl-2',4',6'-tri(propan-2-yl)biphenyl-2-yl]phosphane (97%, 210 mg, 0.42 mmol) was introduced, and the reaction mixture was briefly purged with nitrogen, then heated at 100° C. for 3.5 hours. After the reaction mixture had been cooled and filtered through Celite, the filter pad was thoroughly rinsed with ethyl acetate, and the combined filtrates were concentrated in vacuo. Silica gel chromatography (Eluents: 10%, then 30%, then 50%, then 90% ethyl acetate in heptane) afforded the product as a tan solid, judged to be a mixture of diastereomeric atropisomers from its $^1$H NMR spectrum. Yield: 690 mg, 1.34 mmol, 58%. LCMS m/z 516.3 [M+H$^+$]. $^1$H NMR (400 MHz, CDCl$_3$), characteristic peaks: δ 8.09 (s, 1H), 7.97 (d, J=6.0 Hz, 1H), 7.25 (d, J=6.0 Hz, 1H), 7.17-7.24 (m, 2H), [7.04 (d, J=8.2 Hz) and 7.00 (d, J=8.2 Hz), total 1H], 6.16 (br d, J=10.7 Hz, 1H), 5.72 (dd, J=9.4, 2.5 Hz, 1H), 4.16-4.24 (m, 1H), 4.03-4.10 (m, 2H), 3.73-3.85 (m, 2H), 2.48-2.59 (m, 1H), 2.29-2.43 (m, 1H), 2.04 (br s, 3H), 1.95 (2 s, total 3H).

Step 10. Synthesis of (+)-4,6-dimethyl-5-[2-methyl-4-(1H-pyrazolo[4,3-c]pyridin-4-yloxy)phenyl]pyridazin-3(2H)-one (3) and (−)-4,6-dimethyl-5-[2-methyl-4-(1H-pyrazolo[4,3-c]pyridin-4-yloxy)phenyl]pyridazin-3(2H)-one (4)

C26 (807 mg, 1.56 mmol) was dissolved in 1,4-dioxane (80 mL) and dichloromethane (80 mL). A solution of hydrogen chloride in 1,4-dioxane (4 M, 39.0 mL, 156 mmol) was added, and the reaction mixture was allowed to stir at room temperature for 18 hours. After removal of solvent in vacuo, the residue was partitioned between saturated aqueous sodium bicarbonate solution and ethyl acetate. The aqueous layer was extracted twice with ethyl acetate, and the combined organic layers were dried over sodium sulfate, filtered, and concentrated under reduced pressure. Trituration with diethyl ether afforded racemic 4,6-dimethyl-5-[2-methyl-4-(1H-pyrazolo[4,3-c]pyridin-4-yloxy)phenyl]pyridazin-3(2H)-one as a white solid. Yield: 396 mg, 1.14 mmol, 73%.

LCMS m/z 348.1 [M+H$^+$]. Separation into atropenantiomers was carried out using supercritical fluid chromatography (Column: Chiral Technologies, Chiralcel OJ-H, 5 μm; Eluent: 1:3 methanol/carbon dioxide). The first-eluting product, obtained as an off-white solid, which exhibited a positive (+) rotation, was designated as compound Example 3. Yield: 155 mg, 0.446 mmol, 28%. LCMS m/z 348.2 [M+H$^+$]. $^1$H NMR (400 MHz, CD$_3$OD) δ 8.08 (s, 1H), 7.86 (d, J=6.2 Hz, 1H), 7.26-7.30 (m, 2H), 7.22 (br dd, half of ABX pattern, J=8.2, 2.3 Hz, 1H), 7.17 (d, half of AB quartet, J=8.2 Hz, 1H), 2.11 (s, 3H), 2.03 (s, 3H), 1.93 (s, 3H). Retention time: 5.47 minutes (Column: Chiral Technologies, Chiralcel OJ-H, 250×4.6 mm, 5 μm; Eluent: 1:3 methanol/carbon dioxide; Flow rate: 2.5 mL/minute). The second-eluting product, also an off-white solid, which exhibited a negative (−) rotation, was designated as compound Example 4. Yield: 159 mg, 0.458 mmol, 29%. LCMS m/z 348.2 [M+H$^+$]. $^1$H NMR (400 MHz, CD$_3$OD) δ 8.08 (s, 1H), 7.86 (d, J=6.0 Hz, 1H), 7.26-7.30 (m, 2H), 7.22 (br dd, half of ABX pattern, J=8.2, 2.3 Hz, 1H), 7.17 (d, half of AB quartet, J=8.2 Hz, 1H), 2.11 (s, 3H), 2.03 (s, 3H), 1.93 (s, 3H). Retention time: 5.86 minutes (HPLC conditions identical to those used for Example 3 above).

Example 5

4-[4-(4,6-Dimethylpyrimidin-5-yl)-3-methylphenoxy]-1H-pyrrolo[3,2-c]pyridine (5)

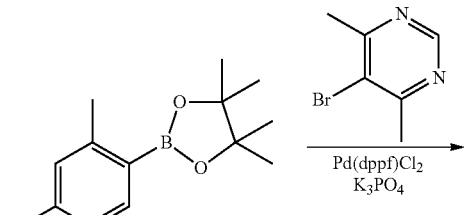

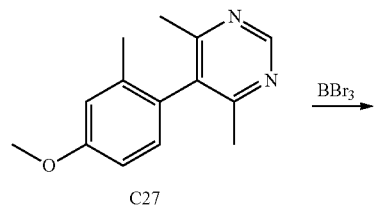

C27

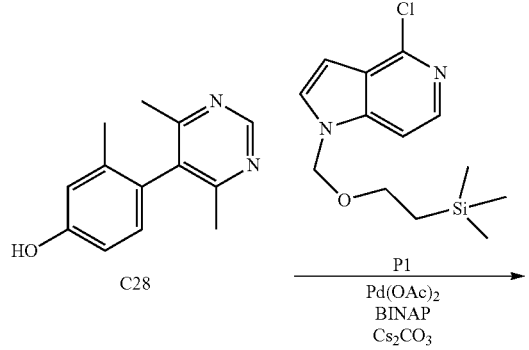

C28

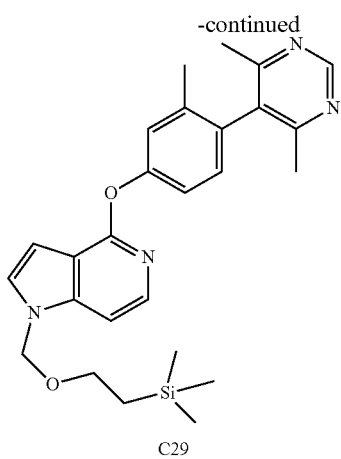

C29

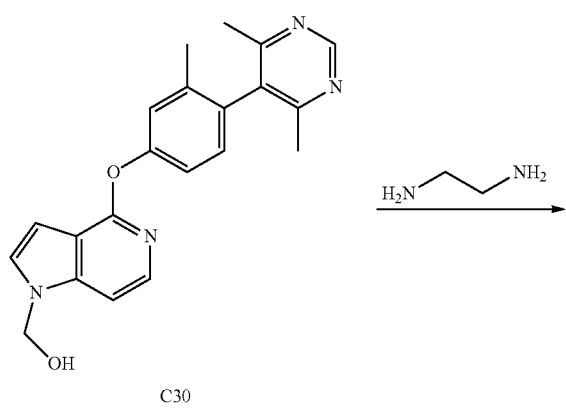

C30

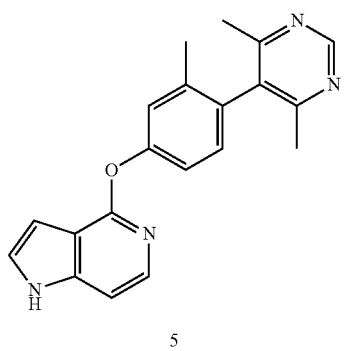 [SMILES: Cc1cc(Oc2nccc3[nH]ccc23)ccc1-c1c(C)ncnc1C]

5

Step 1. Synthesis of 5-(4-methoxy-2-methylphenyl)-4,6-dimethylpyrimidine (C27)

1,1'-Bis(diphenylphosphino)ferrocene]dichloropalladium (II)-dichloromethane complex (5 g, 6 mmol) was added to a degassed mixture of 2-(4-methoxy-2-methylphenyl)-4,4,5,5-tetramethyl-1,3,2-dioxaborolane (30 g, 120 mmol), 5-bromo-4,6-dimethylpyrimidine (22.5 g, 120 mmol), and potassium phosphate (76.3 g, 359 mmol) in 1,4-dioxane (300 mL) and water (150 mL). The reaction mixture was heated at reflux for 4 hours, whereupon it was filtered and concentrated in vacuo. Purification via silica gel chromatography (Gradient: ethyl acetate in petroleum ether) provided the product as a brown solid. Yield: 25 g, 110 mmol, 92%. LCMS m/z 229.3 [M+H$^+$]. $^1$H NMR (300 MHz, CDCl$_3$) δ 8.95 (s, 1H), 6.94 (d, J=8.2 Hz, 1H), 6.87-6.89 (m, 1H), 6.84 (dd, J=8.3, 2.5 Hz, 1H), 3.86 (s, 3H), 2.21 (s, 6H), 1.99 (s, 3H).

Step 2. Synthesis of 4-(4,6-dimethylpyrimidin-5-yl)-3-methylphenol (C28)

Boron tribromide (3.8 mL, 40 mmol) was added drop-wise to a solution of C27 (3.0 g, 13 mmol) in dichloromethane (150 mL) at −70° C. The reaction mixture was stirred at room temperature for 16 hours, then adjusted to pH 8 with saturated aqueous sodium bicarbonate solution. The aqueous layer was extracted with dichloromethane (3×200 mL), and the combined organic layers were dried over sodium sulfate, filtered, and concentrated in vacuo. Silica gel chromatography (Gradient: 60% to 90% ethyl acetate in petroleum ether) afforded the product as a yellow solid. Yield: 1.2 g, 5.6 mmol, 43%. LCMS m/z 215.0 [M+H$^+$]. $^1$H NMR (400 MHz, CDCl$_3$) δ 8.98 (s, 1H), 6.89 (d, J=8.0 Hz, 1H), 6.86 (d, J=2.3 Hz, 1H), 6.80 (dd, J=8.3, 2.5 Hz, 1H), 2.24 (s, 6H), 1.96 (s, 3H).

Step 3. Synthesis of 4-[4-(4,6-dimethylpyrimidin-5-yl)-3-methylphenoxy]-1-{[2-(trimethylsilyl)ethoxy]methyl}-1H-pyrrolo[3,2-c]pyridine (C29)

To a mixture of C28 (390 mg, 1.82 mmol) and 1,4-dioxane (10 mL) was added P1 (566 mg, 2.0 mmol), palladium(II) acetate (40 mg, 0.18 mmol), 1,1'-binaphthalene-2,2'-diylbis(diphenylphosphane) (224 mg, 0.360 mmol) and cesium carbonate (1.76 g, 5.40 mmol). The reaction mixture was stirred at 120° C. for 2 hours, whereupon it was cooled to room temperature, filtered, and concentrated in vacuo. Silica gel chromatography (Eluent: 70:1 dichloromethane/methanol) provided the product as a red oil. Yield: 620 mg, 1.35 mmol, 74%. $^1$H NMR (400 MHz, CD$_3$OD) δ 8.89 (s, 1H), 7.81 (d, J=6.0 Hz, 1H), 7.43 (d, J=3.3 Hz, 1H), 7.39 (br d, J=6 Hz, 1H), 7.18-7.20 (m, 1H), 7.15 (d, half of AB quartet, J=8.3 Hz, 1H), 7.11 (dd, half of ABX pattern, J=8.3, 2.3 Hz, 1H), 6.60 (d, J=3.3 Hz, 1H), 5.60 (s, 2H), 3.52-3.58 (m, 2H), 2.28 (s, 6H), 2.02 (s, 3H), 0.85-0.91 (m, 2H), −0.06 (s, 9H).

Step 4. Synthesis of {4-[4-(4,6-dimethylpyrimidin-5-yl)-3-methylphenoxy]-1H-pyrrolo[3,2-c]pyridin-1-yl}methanol (C30)

A solution of C29 (430 mg, 0.93 mmol) in trifluoroacetic acid (3 mL) was stirred at 80° C. for 1 hour. After cooling to room temperature, the mixture was filtered and the filtrate was concentrated in vacuo. Chromatography on silica gel (Gradient: 3% to 9% methanol in dichloromethane) provided the product as a yellow solid. Yield: 330 mg, 0.92 mmol, 99%.

Step 5. Synthesis of 4-[4-(4,6-dimethylpyrimidin-5-yl)-3-methylphenoxy]-1H-pyrrolo[3,2-c]pyridine (5)

To a solution of C30 (330 mg, 0.92 mmol) in methanol (8 mL) was added ethane-1,2-diamine (300 mg, 5.0 mmol), and the reaction mixture was stirred at 45° C. for 1 hour. After cooling to room temperature, the mixture was concentrated in vacuo and purified using silica gel chromatography (Eluent: 20:1 dichloromethane/methanol) to afford the product as a white solid. Yield: 256 mg, 0.775 mmol, 84%. LCMS m/z 331.1 [M+H$^+$]. $^1$H NMR (400 MHz, CD$_3$OD) δ 8.89 (s, 1H), 7.73 (d, J=5.8 Hz, 1H), 7.32 (d, J=3.0 Hz, 1H), 7.23 (dd, J=5.9, 0.9 Hz, 1H), 7.17 (br d, J=2 Hz, 1H), 7.13 (d, half of AB quartet, J=8.3 Hz, 1H), 7.09 (br dd, half of ABX pattern, J=8.2, 2.4 Hz, 1H), 6.52 (dd, J=3.3, 0.8 Hz, 1H), 2.28 (s, 6H), 2.02 (br s, 3H).

Example 6

4-[4-(4,6-Dimethylpyrimidin-5-yl)-3-methylphenoxy]-1H-pyrazolo[4,3-c]pyridine (6)

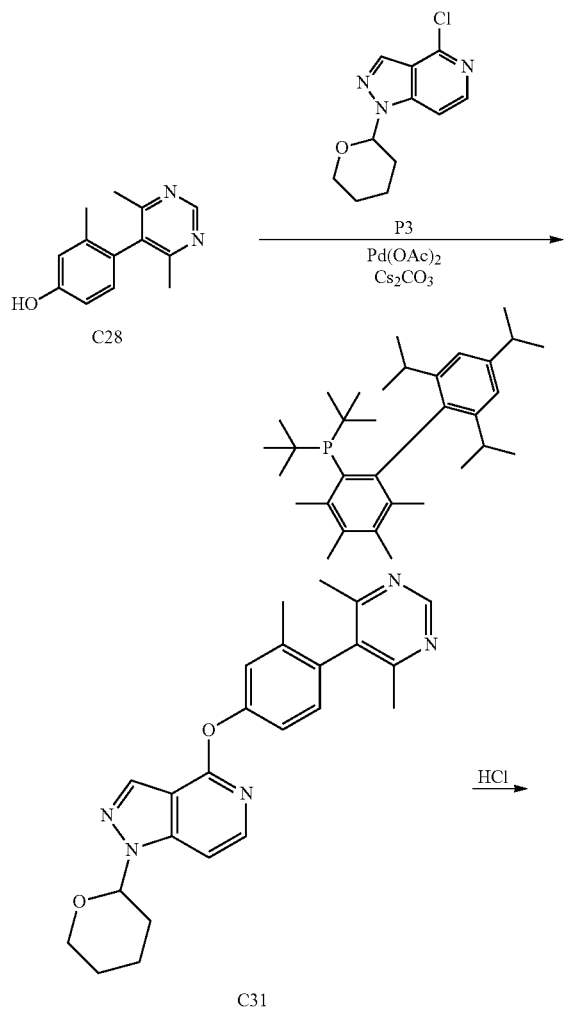

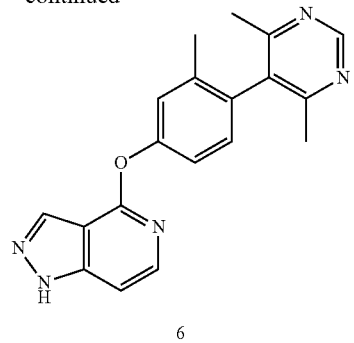

Step 1. Synthesis of 4-[4-(4,6-dimethylpyrimidin-5-yl)-3-methylphenoxy]-1-(tetrahydro-2H-pyran-2-yl)-1H-pyrazolo[4,3-c]pyridine (C31)

Cesium carbonate (1.03 g, 3.16 mmol) and palladium(II) acetate (24 mg, 0.11 mmol) were added to a solution of C28 (225 mg, 1.05 mmol) and P3 (250 mg, 1.05 mmol) in 1,4-dioxane (10 mL) in a sealable reaction vessel, and the solution was purged with nitrogen for 10 minutes. Di-tert-butyl[3,4,5,6-tetramethyl-2',4',6-tri(propan-2-yl)biphenyl-2-yl]phosphane (97%, 104 mg, 0.210 mmol) was added, and the reaction mixture was briefly purged with nitrogen. The vessel was sealed and the reaction mixture was stirred at 100° C. for 3 hours. After cooling to room temperature, the mixture was filtered through Celite and the filter pad was washed with ethyl acetate; the combined filtrates were concentrated in vacuo and purified via silica gel chromatography (Eluents: 20%, then 50%, then 100% ethyl acetate in heptane). The product was obtained as an off-white solid. Yield: 272 mg, 0.655 mmol, 62%. LCMS m/z 416.5 [M+H$^+$]. $^1$H NMR (400 MHz, CDCl$_3$) δ 8.99 (s, 1H), 8.11 (d, J=0.6 Hz, 1H), 7.99 (d, J=6.0 Hz, 1H), 7.25-7.27 (m, 2H, assumed; partially obscured by solvent peak), 7.20-7.24 (m, 1H), 7.10 (d, J=8.4 Hz, 1H), 5.73 (dd, J=9.4, 2.5 Hz, 1H), 4.04-4.10 (m, 1H), 3.74-3.82 (m, 1H), 2.49-2.59 (m, 1H), 2.28 (s, 6H), 2.08-2.21 (m, 2H), 2.04 (s, 3H), 1.66-1.84 (s, 3H).

Step 2. Synthesis of 4-[4-(4,6-dimethylpyrimidin-5-yl)-3-methylphenoxy]-1H-pyrazolo[4,3-c]pyridine (6)

C31 (172 mg, 0.414 mmol) was dissolved in 1,4-dioxane (5 mL) and dichloromethane (5 mL), and cooled to 0° C. A solution of hydrogen chloride in 1,4-dioxane (4 M, 1.04 mL, 4.16 mmol) was added, and the reaction mixture was allowed to stir at room temperature for 45 hours. After removal of solvent in vacuo, the residue was partitioned between saturated aqueous sodium bicarbonate solution and dichloromethane. The aqueous layer was extracted twice with dichloromethane, and the combined organic layers were dried over sodium sulfate, filtered, and concentrated under reduced pressure, affording the product as an off-white solid. Yield: 130 mg, 0.392 mmol, 95%. LCMS m/z 332.3 [M+H$^+$]. $^1$H NMR (400 MHz, CDCl$_3$) δ 9.00 (s, 1H), 8.20 (br s, 1H), 7.99 (d, J=6.0 Hz, 1H), 7.28-7.30 (m, 1H), 7.23-7.27 (m, 1H), 7.16 (dd, J=6.0, 1.0 Hz, 1H), 7.11 (d, J=8.2 Hz, 1H), 2.28 (s, 6H), 2.05 (s, 3H).

Example 7

4,6-Dimethyl-5-[4-(1H-pyrrolo[3,2-c]pyridin-4-yloxy)phenyl]pyridazin-3(2H)-one (7)

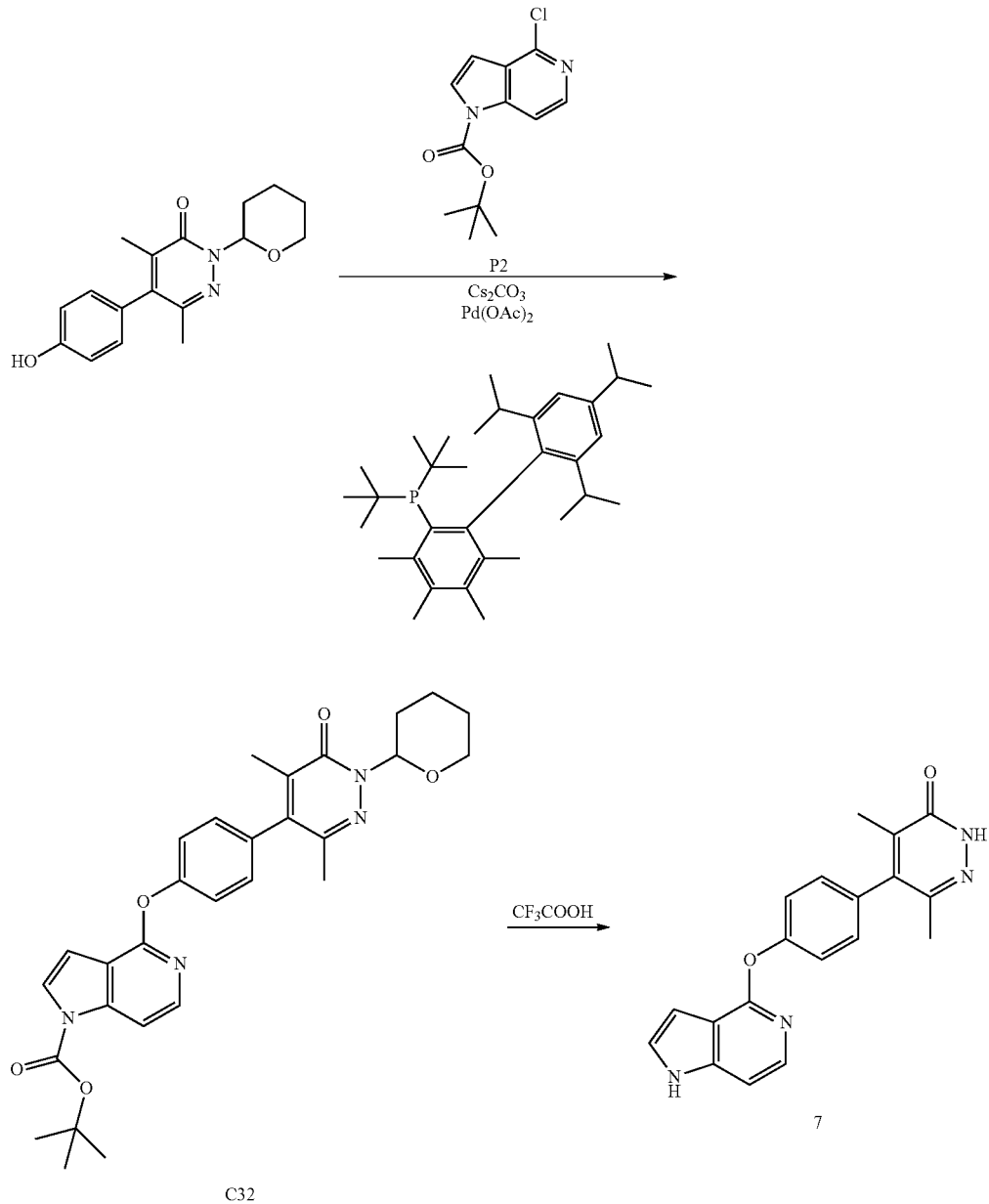

Step 1. Synthesis of tert-butyl 4-{4-[3,5-dimethyl-6-oxo-1-(tetrahydro-2H-pyran-2-yl)-1,6-dihydropyridazin-4-yl]phenoxy}-1H-pyrrolo[3,2-c]pyridine-1-carboxylate (C32)

A mixture of 5-(4-hydroxyphenyl)-4,6-dimethyl-2-(tetrahydro-2H-pyran-2-yl)pyridazin-3(2H)-one (prepared in a manner analogous to C25 in Examples 3 and 4) (600 mg, 2.00 mmol), P2 (757 mg, 3.00 mmol), cesium carbonate (1.95 g, 5.99 mmol), palladium(II) acetate (44 mg, 0.20 mmol) and di-tert-butyl[3,4,5,6-tetramethyl-2',4',6'-tri(propan-2-yl)biphenyl-2-yl]phosphane (97%, 200 mg, 0.40 mmol) in 1,4-dioxane (15 mL) was purged with nitrogen for 10 minutes, and then heated at 80° C. for 18 hours. After filtration, the filtrate was diluted with water and extracted several times with ethyl acetate. The combined organic layers were washed with water, washed with saturated aqueous sodium chloride solution, dried over magnesium sulfate, filtered, and concentrated in vacuo. Purification via silica gel chromatography (Gradient: 25% to 50% ethyl acetate in heptane) provided the product as a white solid. Yield: 860 mg, 1.66 mmol, 83%.

LCMS m/z 517.1 [M+H⁺]. ¹H NMR (400 MHz, CDCl₃), characteristic peaks: δ 8.04 (d, J=5.8 Hz, 1H), 7.80 (br d, J=5.8 Hz, 1H), 7.62 (d, J=3.7 Hz, 1H), 7.31-7.36 (m, 2H), 7.11-7.19 (m, 2H), 6.75 (dd, J=3.7, 0.6 Hz, 1H), 6.15 (dd, J=10.7, 2.0 Hz, 1H), 4.15-4.21 (m, 1H), 3.76-3.84 (m, 1H), 2.29-2.41 (m, 1H), 2.12 (s, 3H), 2.01 (s, 3H), 1.71 (s, 9H).

Step 2. Synthesis of 4,6-dimethyl-5-[4-(1H-pyrrolo[3,2-c]pyridin-4-yloxy)phenyl]pyridazin-3(2H)-one (7)

Trifluoroacetic acid (5 mL) was added to a solution of C32 (850 mg, 1.64 mmol) in dichloromethane (15 mL), and the reaction mixture was allowed to stir at room temperature for 18 hours. After removal of volatiles under reduced pressure, the residue was dissolved in saturated aqueous sodium bicarbonate solution and extracted several times with ethyl acetate. The combined organic layers were washed with water, washed with saturated aqueous sodium chloride solution, dried over magnesium sulfate, filtered, and concentrated in vacuo. The resulting material was suspended in ethyl acetate, stirred for 10 minutes and filtered, affording the product as a white solid. Yield: 280 mg, 0.842 mmol, 51%. LCMS m/z 333.1 [M+H⁺]. ¹H NMR (400 MHz, DMSO-d₆) δ 12.77 (br s, 1H), 11.69 (br s, 1H), 7.72 (d, J=5.8 Hz, 1H), 7.43 (dd, J=3.2, 2.3 Hz, 1H), 7.29 (s, 4H), 7.20 (dd, J=5.8, 0.9 Hz, 1H), 6.55 (ddd, J=3.2, 2.0, 0.9 Hz, 1H), 1.97 (s, 3H), 1.83 (s, 3H).

Example 8

(−)-1,5-Dimethyl-6-[2-methyl-4-(1H-pyrazolo[4,3-c]pyridin-4-yloxy)phenyl]pyrimidine-2,4(1H,3H)-dione (8)

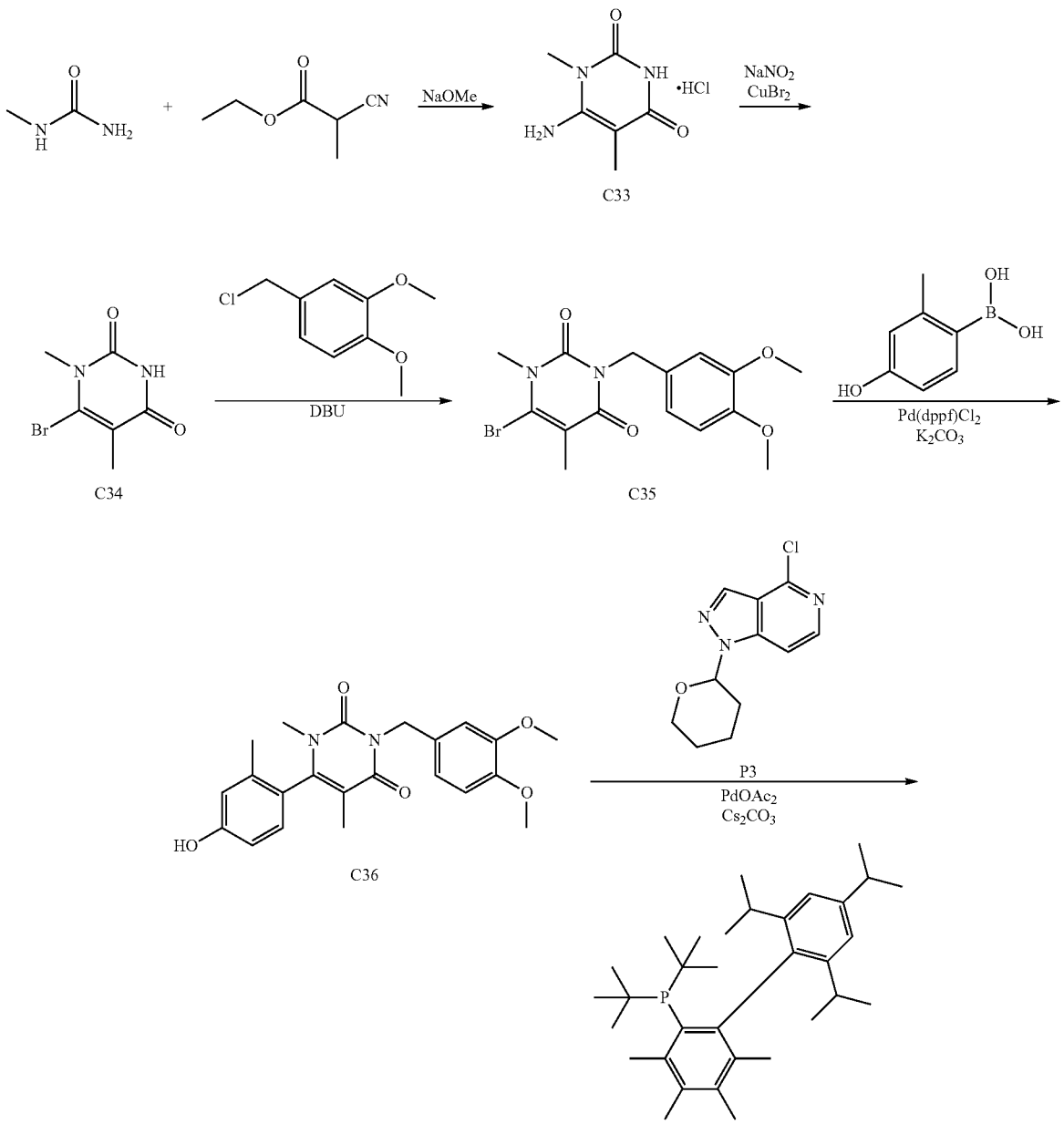

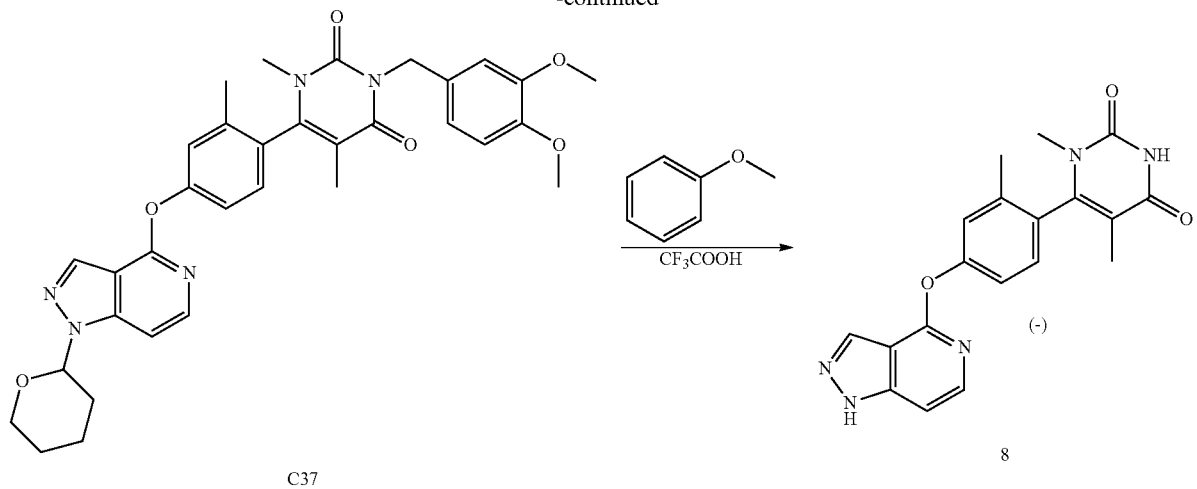

Step 1. Synthesis of 6-amino-1,5-dimethylpyrimidine-2,4(1H,3H)-dione, hydrochloride salt (C33)

A solution of sodium methoxide in methanol (4.4 M, 27 mL, 119 mmol) was added to a solution of ethyl 2-cyanopropanoate (95%, 13.2 mL, 99.6 mmol) and 1-methylurea (98%, 8.26 g, 109 mmol) in methanol (75 mL), and the reaction mixture was heated at reflux for 18 hours, then cooled to room temperature. After removal of solvent in vacuo, the residue was repeatedly evaporated under reduced pressure with acetonitrile (3×50 mL), then partitioned between acetonitrile (100 mL) and water (100 mL). Aqueous 6 M hydrochloric acid was slowly added until the pH had reached approximately 2; the resulting mixture was stirred for one hour. The precipitate was collected via filtration and washed with tert-butyl methyl ether, affording the product as a white solid. Yield: 15.2 g, 79.3 mmol, 80%. LCMS m/z 156.1 [M+H$^+$]. $^1$H NMR (400 MHz, DMSO-d$_6$) δ 10.38 (br s, 1H), 6.39 (s, 2H), 3.22 (s, 3H), 1.67 (s, 3H).

Step 2. Synthesis of 6-bromo-1,5-dimethylpyrimidine-2,4(1H,3H)-dione (C34)

A 1:1 mixture of acetonitrile and water (120 mL) was added to a mixture of C33 (9.50 g, 49.6 mmol), sodium nitrite (5.24 g, 76 mmol), and copper(II) bromide (22.4 g, 100 mmol), and the reaction mixture was allowed to stir at room temperature for 66 hours. Addition of aqueous sulfuric acid (1 N, 200 mL) and ethyl acetate (100 mL) provided a precipitate, which was collected via filtration and washed with water and ethyl acetate to afford the product as a light yellow solid (7.70 g). The organic layer of the filtrate was concentrated to a smaller volume, during which additional precipitate formed; this was isolated via filtration and washed with 1:1 ethyl acetate/heptane to provide additional product (0.4 g). Total yield: 8.1 g, 37 mmol, 75%. LCMS m/z 217.9 [M+H$^+$]. $^1$H NMR (400 MHz, DMSO-d$_6$) δ 11.58 (br s, 1H), 3.45 (s, 3H), 1.93 (s, 3H).

Step 3. Synthesis of 6-bromo-3-(3,4-dimethoxybenzyl)-1,5-dimethylpyrimidine-2,4(1H,3H)-dione (C35)

1,8-Diazabicyclo[5.4.0]undec-7-ene (98%, 5.57 mL, 36.5 mmol) was added to a suspension of C34 (4.00 g, 18.3 mmol) and 4-(chloromethyl)-1,2-dimethoxybenzene (5.16 g, 27.6 mmol) in acetonitrile (80 mL), and the reaction mixture was heated at 60° C. for 18 hours. After removal of solvent in vacuo, the residue was purified via silica gel chromatography (Gradient: 25% to 50% ethyl acetate in heptane) to afford the product as a white solid. Yield: 5.70 g, 15.4 mmol, 84%. $^1$H NMR (400 MHz, CDCl$_3$) δ 7.08-7.12 (m, 2H), 6.80 (d, J=8.0 Hz, 1H), 5.07 (s, 2H), 3.88 (s, 3H), 3.85 (s, 3H), 3.65 (s, 3H), 2.14 (s, 3H).

Other suitable protecting groups can also be used to protect the "NH" group of C34. For example, SEM, BOM, or Boc can be used instead of the dimethoxybenzyl in C35.

Step 4. Synthesis of 3-(3,4-dimethoxybenzyl)-6-(4-hydroxy-2-methylphenyl)-1,5-dimethylpyrimidine-2,4(1H,3H)-dione (C36)

An aqueous solution of potassium carbonate (3.0 M, 3.3 mL, 9.9 mmol) was added to a mixture of C35 (1.20 g, 3.25 mmol), (4-hydroxy-2-methylphenyl)boronic acid (988 mg, 6.50 mmol), [1,1'-bis(diphenylphosphino)ferrocene]dichloropalladium(II), dichloromethane complex (98%, 271 mg, 0.325 mmol) and 1,4-dioxane (30 mL). After the reaction mixture had been heated at 100° C. for 66 hours, it was cooled to room temperature, diluted with ethyl acetate and water, and filtered through Celite. The organic layer from the filtrate was washed with saturated aqueous sodium bicarbonate solution, washed with saturated aqueous sodium chloride solution, dried over magnesium sulfate, filtered, and concentrated in vacuo. Purification using silica gel chromatography (Gradient: 25% to 50% ethyl acetate in heptane) afforded the product as a white foam. Yield: 650 mg, 1.64 mmol, 50%. LCMS m/z 397.2 [M+H$^+$]. $^1$H NMR (400 MHz, CDCl$_3$) δ 7.22 (d, J=2.0 Hz, 1H), 7.19 (dd, J=8.2, 2.0 Hz, 1H), 6.92 (d, J=8.1 Hz, 1H), 6.81-6.84 (m, 2H), 6.79 (br dd, J=8.2, 2.5 Hz, 1H), 5.53 (br s, 1H), 5.17 (AB quartet, J$_{AB}$=13.4 Hz, Δv$_{AB}$=18.8 Hz, 2H), 3.90 (s, 3H), 3.87 (s, 3H), 3.03 (s, 3H), 2.10 (br s, 3H), 1.66 (s, 3H).

Alternatively, the free OH group of (4-hydroxy-2-methylphenyl)boronic acid can be protected by a suitable protecting group (e.g., MOM or benzyl) before (4-hydroxy-2-methylphenyl)boronic acid is coupled to C35. In such a case, the product of the coupling reaction can be deprotected to afford C36.

Step 5. Synthesis of 3-(3,4-dimethoxybenzyl)-1,5-dimethyl-6-(2-methyl-4-{[1-(tetrahydro-2H-pyran-2-yl)-1H-pyrazolo[4,3-c]pyridin-4-yl]oxy}phenyl)pyrimidine-2,4(1H,3H)-dione (C37)

C36 was converted to the product using the method employed for synthesis of C26 in Examples 3 and 4. In this case, after filtration through Celite and rinsing of the filter pad with ethyl acetate, the organic layer of the combined filtrates was washed with water, washed with saturated aqueous sodium chloride solution, dried over sodium sulfate, filtered, and concentrated in vacuo. Purification via silica gel chromatography (Gradient: 50% to 100% ethyl acetate in heptanes) provided the product as a tan solid. Yield: 490 mg, 0.820 mmol, 63%. LCMS m/z 598.3 [M+H$^+$]. $^1$H NMR (400 MHz, CDCl$_3$), characteristic peaks: δ 8.06-8.08 (m, 1H), 7.99 (d, J=6.2 Hz, 1H), 7.32 (dd, J=6.2, 0.9 Hz, 1H), 7.24 (br d, J=2.0 Hz, 1H), 7.21 (br dd, J=8.1, 2.0 Hz, 1H), 7.15 (d, J=8.2 Hz, 1H), 6.84 (d, J=8.2 Hz, 1H), 5.74 (dd, J=9.2, 2.5 Hz, 1H), 5.18 (AB quartet, J$_{AB}$=13.4 Hz, Δv$_{AB}$=19.1 Hz, 2H), 4.03-4.09 (m, 1H), 3.92 (s, 3H), 3.88 (s, 3H), 3.74-3.82 (m, 1H), 3.11 (s, 3H), 2.21 (br s, 3H), 1.71 (s, 3H).

Step 6. Synthesis of (−)-1,5-dimethyl-6-[2-methyl-4-(1H-pyrazolo[4,3-c]pyridin-4-yloxy)phenyl]pyrimidine-2,4(1H,3H)-dione (8)

C37 (490 mg, 0.820 mmol), trifluoroacetic acid (8 mL) and methoxybenzene (0.446 mL, 4.10 mmol) were combined in a pressure tube; the tube was sealed and the reaction mixture was heated at 120° C. for 42 hours. After cooling to room temperature, the reaction mixture was concentrated in vacuo and partitioned between ethyl acetate (100 mL) and saturated aqueous sodium bicarbonate solution (20 mL). The organic layer was washed sequentially with water (10 mL) and with saturated aqueous sodium chloride solution (10 mL), dried over magnesium sulfate, filtered, and concentrated under reduced pressure. After chromatography on silica gel (Gradient: 65% to 100% ethyl acetate in heptane), the product was subjected to supercritical fluid chromatography on a chiral column. One atropenantiomer was collected, providing the product as a solid; this material exhibited a negative (−) rotation. Yield: 95 mg, 0.26 mmol, 32%. LCMS m/z 364.2 [M+H$^+$]. $^1$H NMR (400 MHz, CDCl$_3$) δ 8.33 (br s, 1H), 8.24 (br s, 1H), 7.98 (d, J=6.1 Hz, 1H), 7.27-7.32 (m, 2H, assumed; partially obscured by solvent peak), 7.19 (dd, J=6.1, 1.0 Hz, 1H), 7.18 (br d, J=8 Hz, 1H), 3.08 (s, 3H), 2.23 (br s, 3H), 1.70 (s, 3H)

Examples 9 and 10

4,6-Dimethyl-5-[2-methyl-4-(1H-pyrrolo[3,2-c]pyridin-4-yloxy)phenyl]pyridazin-3(2H)-one, ENT-1 (9) and 4,6-Dimethyl-5-[2-methyl-4-(1H-pyrrolo[3,2-c]pyridin-4-yloxy)phenyl]pyridazin-3(2H)-one, ENT-2 (10)

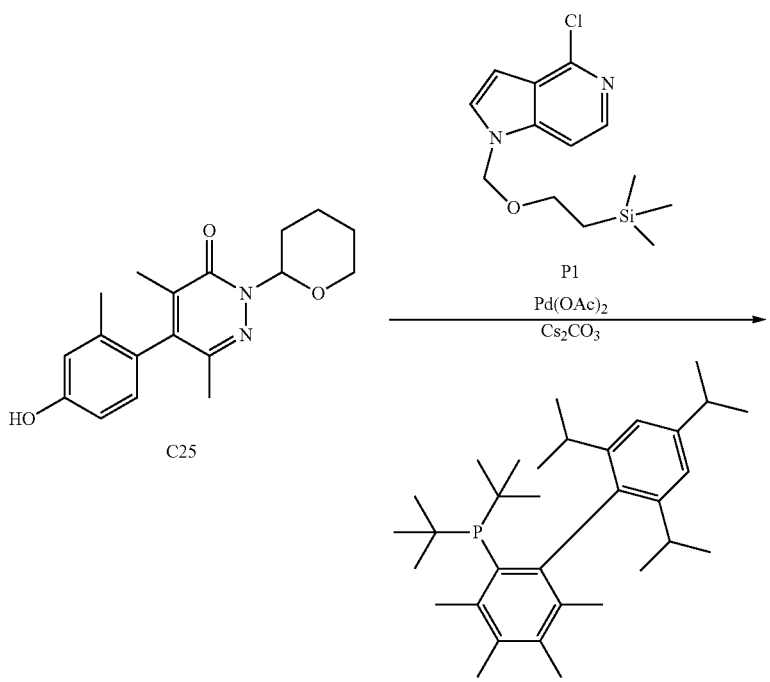

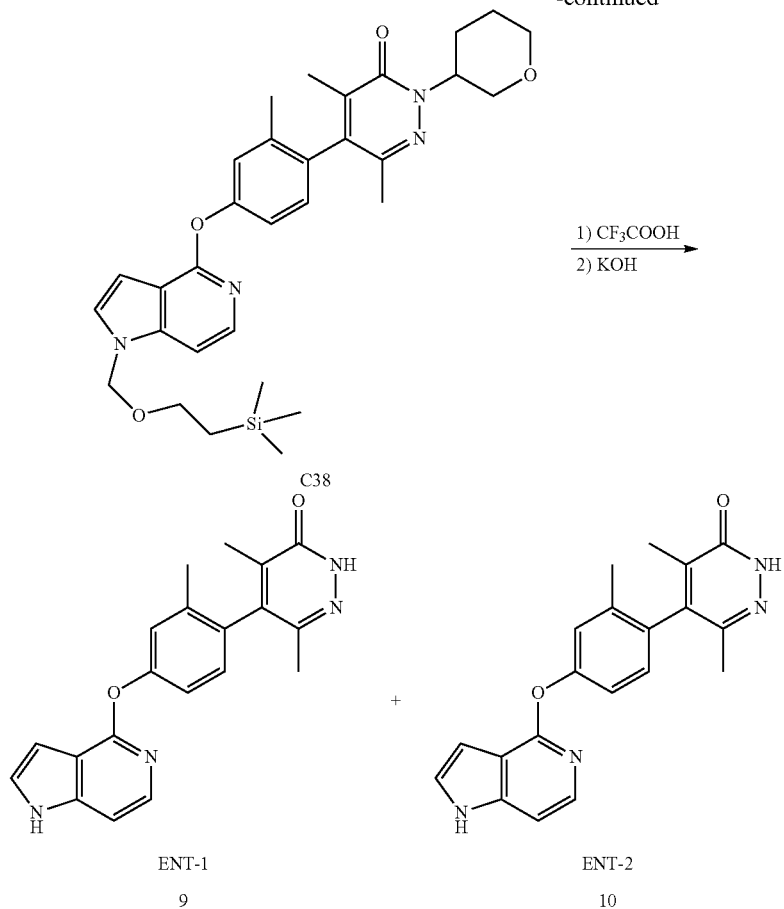

Step 1. Synthesis of 4,6-dimethyl-5-{2-methyl-4-[(1-{[2-(trimethylsilyl)ethoxy]methyl}-1H-pyrrolo[3,2-c]pyridin-4-yl)oxy]phenyl}-2-(tetrahydro-2H-pyran-2-yl)pyridazin-3(2H)-one (C38)

C25 was reacted with P1 using the method described for synthesis of C31 in Example 6. The product, assigned as a mixture of diastereomeric atropisomers on the basis of its $^1$H NMR spectrum, was obtained as a solid. Yield: 53 mg, 94 μmol, 27%. LCMS m/z 561.4 [M+H$^+$]. $^1$H NMR (400 MHz, CDCl$_3$), characteristic peaks: δ 7.98 (br d, J=6 Hz, 1H), 6.96-7.04 (m, 1H), 6.13-6.18 (m, 1H), 5.51 (s, 2H), 4.16-4.24 (m, 1H), 3.77-3.85 (m, 1H), 3.48-3.54 (m, 2H), 2.04 (2 s, total 3H), 1.95 (2 s, total 3H), 0.89-0.94 (m, 2H), −0.03 (s, 9H).

Step 2. Synthesis of 4,6-dimethyl-5-[2-methyl-4-(1H-pyrrolo[3,2-c]pyridin-4-yloxy)phenyl]pyridazin-3(2H)-one, ENT-1 (9) and 4,6-dimethyl-5-[2-methyl-4-(1H-pyrrolo[3,2-c]pyridin-4-yloxy)phenyl]pyridazin-3(2H)-one, ENT-2 (10)

Trifluoroacetic acid (1 mL) was added to a solution of C38 (53 mg, 94 μmol) in dichloromethane (3 mL) and the reaction mixture was stirred at room temperature for 18 hours. The solution was partitioned between ethyl acetate and saturated aqueous sodium bicarbonate solution; the aqueous layer was extracted three times with ethyl acetate, and the combined organic layers were combined, dried, filtered, and concentrated in vacuo. The residue was taken up in tetrahydrofuran (5 mL) and water (1 mL), treated with potassium hydroxide (300 mg, 5.3 mmol), and stirred at room temperature for 18 hours. The reaction mixture was then partitioned between ethyl acetate and saturated aqueous ammonium chloride solution; the aqueous layer was extracted three times with ethyl acetate, and the combined organic layers were dried, filtered, and concentrated under reduced pressure. The resulting solid (40 mg) was subjected to supercritical fluid chromatography (Column: Chiral Technologies, Chiralpak AS-H, 5 μm, Eluent: 7:3 carbon dioxide/methanol). The first-eluting atropenantiomer, isolated as a solid, was designated as compound 9. Yield: 8 mg, 20 μmol, 20%. LCMS m/z 347.1 [M+H$^+$]. $^1$H NMR (400 MHz, CD$_3$OD) δ 7.78 (br d, J=5.8 Hz, 1H), 7.36 (d, J=3.1 Hz, 1H), 7.31 (d, J=6.0 Hz, 1H), 7.20-7.22 (m, 1H), 7.10-7.16 (m, 2H), 6.39 (d, J=3.1 Hz, 1H), 2.08 (s, 3H), 2.02 (s, 3H), 1.92 (s, 3H). Retention time: 4.07 minutes (Column: Chiral Technologies, Chiralpak AS-H, 4.6×250 mm, 5 μm; Eluent: 5% methanol in carbon dioxide for 1.0 minute, followed by a gradient of 5% to 50% methanol in carbon dioxide over 6.0 minutes; Flow rate: 4.0 mL/minute). The second-eluting atropenantiomer, designated as compound 10, was also obtained as a solid. Yield: 8 mg, 20 μmol, 20%. LCMS m/z 347.2 [M+H$^+$]. $^1$H NMR (400 MHz, CD$_3$OD) δ 7.88 (br d, J=6.4 Hz, 1H), 7.47 (br d, J=6 Hz, 1H), 7.45 (d, J=3.3 Hz, 1H), 7.34 (br d, J=2 Hz, 1H), 7.27 (br dd, half of ABX pattern, J=8.3, 2.2 Hz, 1H), 7.21 (d, half of AB quartet, J=8.4 Hz, 1H), 6.16 (dd, J=3.3, 0.6 Hz, 1H), 2.11 (s, 3H), 2.02 (s, 3H), 1.92 (s, 3H). Retention time: 5.47 minutes (HPLC conditions identical to those described for compound 9).

Examples 11 and 12
4-[4-(3,5-Dimethylpyridazin-4-yl)-3-methylphenoxy]-1H-pyrrolo[3,2-c]pyridine, ENT-1 (11) and 4-[4-(3,5-Dimethylpyridazin-4-yl)-3-methylphenoxy]-1H-pyrrolo[3,2-c]pyridine, ENT-2 (12)
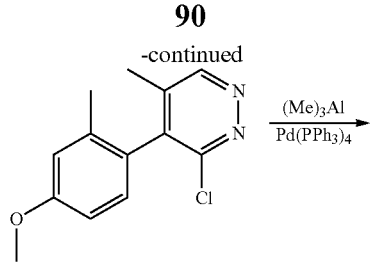
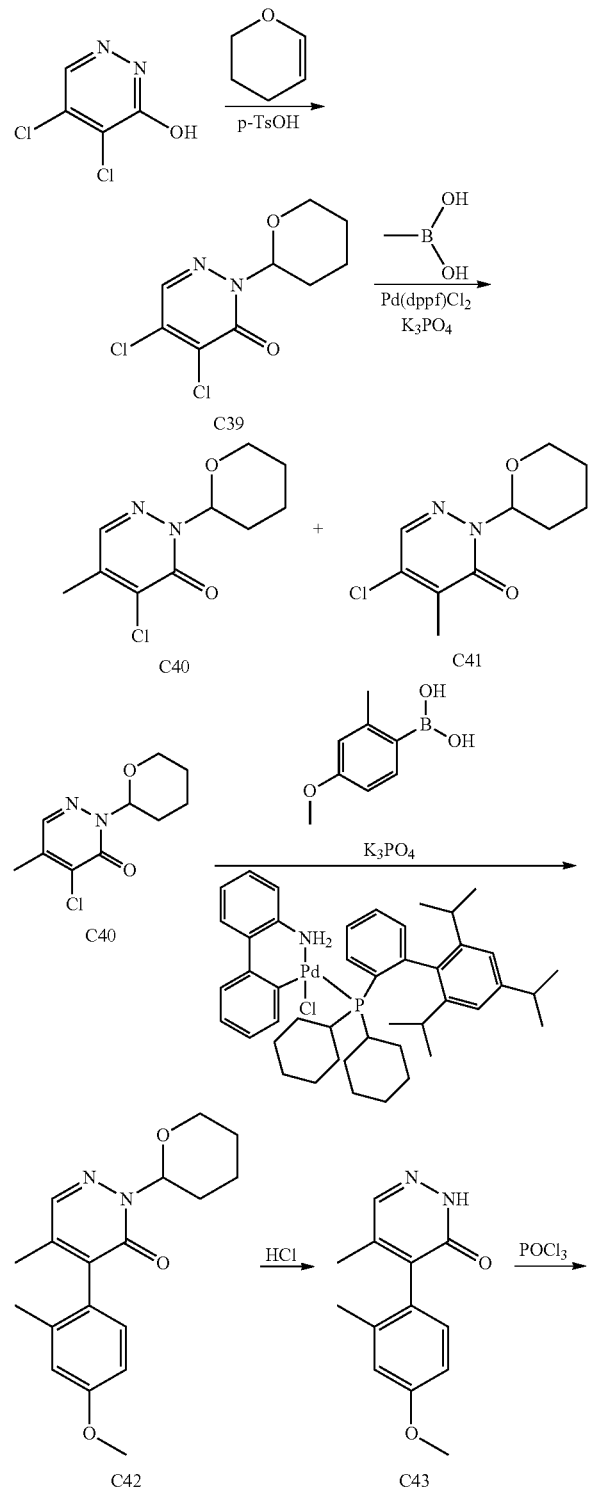
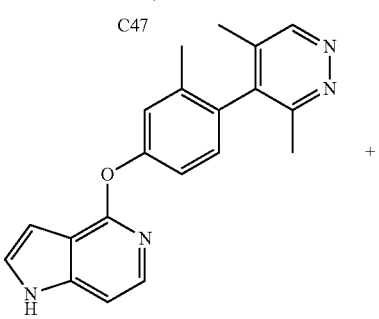

-continued

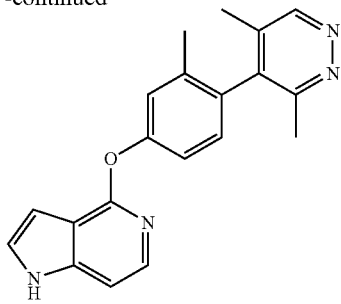

ENT-2
12

Step 1. Synthesis of 4,5-dichloro-2-(tetrahydro-2H-pyran-2-yl)pyridazin-3(2H)-one (C39)

A mixture of 4,5-dichloropyridazin-3-ol (42 g, 250 mmol), 3,4-dihydro-2H-pyran (168 g, 2.00 mol) and p-toluenesulfonic acid (8.8 g, 51 mmol) in tetrahydrofuran (2 L) was heated at reflux for 2 days. After cooling to room temperature, the reaction mixture was concentrated in vacuo and purified by silica gel chromatography (Gradient: 3% to 5% ethyl acetate in petroleum ether). The product was obtained as a white solid. Yield: 42 g, 170 mmol, 68%. $^1$H NMR (400 MHz, CDCl$_3$) δ 7.84 (s, 1H), 6.01 (br d, J=11 Hz, 1H), 4.10-4.16 (m, 1H), 3.70-3.79 (m, 1H), 1.99-2.19 (m, 2H), 1.50-1.80 (m, 4H).

Step 2. Synthesis of 4-chloro-5-methyl-2-(tetrahydro-2H-pyran-2-yl)pyridazin-3(2H)-one (C40) and 5-chloro-4-methyl-2-(tetrahydro-2H-pyran-2-yl)pyridazin-3(2H)-one (C41)

To a mixture of C39 (40 g, 0.16 mol), methylboronic acid (9.6 g, 0.16 mol) and cesium carbonate (156 g, 479 mmol) in 1,4-dioxane (500 mL) and water (50 mL) was added [1,1'-bis(diphenylphosphino)ferrocene]dichloropalladium(II) (5 g, 7 mmol). The reaction mixture was stirred at 110° C. for 2 hours, whereupon it was cooled to room temperature and concentrated in vacuo. Purification via silica gel chromatography (Gradient: 3% to 6% ethyl acetate in petroleum ether) afforded compound C40 as a pale yellow solid. Yield: 9.0 g, 39 mmol, 24%. LCMS m/z 250.8 [M+Na$^+$]. $^1$H NMR (400 MHz, CDCl$_3$) δ 7.71 (s, 1H), 6.07 (dd, J=10.7, 2.1 Hz, 1H), 4.10-4.18 (m, 1H), 3.71-3.81 (m, 1H), 2.30 (s, 3H), 1.98-2.19 (m, 2H), 1.53-1.81 (m, 4H). Also obtained was C41, as a pale yellow solid. Yield: 9.3 g, 41 mmol, 26%. LCMS m/z 250.7 [M+Na$^+$]. $^1$H NMR (400 MHz, CDCl$_3$) δ 7.77 (s, 1H), 6.02 (dd, J=10.7, 2.1 Hz, 1H), 4.10-4.17 (m, 1H), 3.71-3.79 (m, 1H), 2.27 (s, 3H), 1.99-2.22 (m, 2H), 1.51-1.79 (m, 4H).

Step 3. Synthesis of 4-(4-methoxy-2-methylphenyl)-5-methyl-2-(tetrahydro-2H-pyran-2-yl)pyridazin-3(2H)-one (C42)

A degassed aqueous potassium phosphate solution (0.5 M, 4.37 mL, 2.18 mmol) was added to a degassed solution of (4-methoxy-2-methylphenyl)boronic acid (200 mg, 1.20 mmol), C40 (250 mg, 1.09 mmol), and [2'-(azanidyl-κN)biphenyl-2-yl-κC$_2$](chloro){dicyclohexyl[2',4',6'-tri(propan-2-yl)biphenyl-2-yl]-λ$^5$-phosphanyl}palladium (22 mg, 28 μmol) in tetrahydrofuran (4 mL). After 4 hours at room temperature, the reaction mixture was diluted with ethyl acetate; the organic layer was washed twice with saturated aqueous sodium chloride solution, then dried over magnesium sulfate, filtered, and concentrated in vacuo. Silica gel chromatography (Eluent: 3:7 ethyl acetate/heptane) afforded the product as a gum. Yield: 290 mg, 0.922 mmol, 85%. LCMS m/z 315.1 [M+H$^+$]. $^1$H NMR (400 MHz, CDCl$_3$), presumed to be a mixture of diastereomeric atropisomers; δ 7.76 and 7.77 (2 s, total 1H), [6.92 (d, J=8.4 Hz) and 6.93 (d, J=8.4 Hz), total 1H], 6.79-6.82 (m, 1H), 6.76 (dd, J=8.4, 2.5 Hz, 1H), 6.06 (dd, J=10.7, 2.1 Hz, 1H), 4.09-4.17 (m, 1H), 3.78 (s, 3H), 3.66-3.76 (m, 1H), 2.09-2.26 (m, 1H), 2.08 and 2.08 (2 s, total 3H), 1.96-2.05 (m, 1H), 1.93 and 1.94 (2 s, total 3H), 1.63-1.80 (m, 3H), 1.48-1.60 (m, 1H).

Step 4. Synthesis of 4-(4-methoxy-2-methylphenyl)-5-methylpyridazin-3(2H)-one (C43)

C42 (184 mg, 0.585 mmol) was mixed with a solution of hydrogen chloride in 1,4-dioxane (4 M, 8 mL) and allowed to stir for 1 hour. Concentration in vacuo provided the product as a solid (140 mg), which was taken directly to the next step. LCMS m/z 231.1 [M+H$^+$]. $^1$H NMR (400 MHz, CD$_3$OD) δ 7.98 (br s, 1H), 6.98 (d, J=8.4 Hz, 1H), 6.89 (br d, J=2.5 Hz, 1H), 6.84 (br dd, J=8.4, 2.7 Hz, 1H), 3.82 (s, 3H), 2.09 (br s, 3H), 2.01 (s, 3H).

Step 5. Synthesis of 3-chloro-4-(4-methoxy-2-methylphenyl)-5-methylpyridazine (C44)

A mixture of C43 (from the previous step, 140 mg) and phosphorus oxychloride (1.5 mL, 16 mmol) was stirred at 90° C. for 1.5 hours. After removal of the phosphorus oxychloride in vacuo, the residue was partitioned between dichloromethane (120 mL) and water (20 mL) and neutralized with sodium bicarbonate. The organic layer was washed sequentially with aqueous sodium bicarbonate solution (2×50 mL) and water (2×50 mL), then dried over magnesium sulfate, filtered, and concentrated under reduced pressure. The product was obtained as a gum. Yield: 133 mg, 0.535 mmol, 91% over two steps. LCMS m/z 249.1 [M+H$^+$]. $^1$H NMR (400 MHz, CDCl$_3$) δ 9.03 (s, 1H), 6.94 (d, half of AB quartet, J=8.2 Hz, 1H), 6.84-6.91 (m, 2H), 3.87 (s, 3H), 2.11 (s, 3H), 2.03 (s, 3H).

Step 6. Synthesis of 4-(4-methoxy-2-methylphenyl)-3,5-dimethylpyridazine (C45)

Nitrogen was bubbled for 10 minutes into a stirring mixture of tetrakis(triphenylphosphine)palladium(0) (32 mg, 28 μmol) and C44 (133 mg, 0.535 mmol) in 1,4-dioxane (5 mL). Trimethylaluminum (2 M in toluene, 0.5 mL, 1.0 mmol) was then added, and the reaction mixture was heated at 95° C. for 1.5 hours. After cooling, the reaction mixture was quenched via drop-wise addition of methanol, then diluted with methanol. The mixture was filtered through Celite, and the filtrate was concentrated in vacuo. Silica gel chromatography (Eluent: 5% methanol in ethyl acetate) afforded the product as an oil. Yield: 94 mg, 0.41 mmol, 77%. LCMS m/z 229.1 [M+H$^+$]. $^1$H NMR (400 MHz, CDCl$_3$) δ 8.91 (s, 1H), 6.78-6.86 (m, 3H), 3.80 (s, 3H), 2.32 (s, 3H), 1.97 (s, 3H), 1.91 (s, 3H).

Step 7. Synthesis of 4-(3,5-dimethylpyridazin-4-yl)-3-methylphenol (C46)

Boron tribromide (1 M solution in dichloromethane, 13.0 mL, 13.0 mmol) was added drop-wise to a −78° C. solution of C45 (740 mg, 3.24 mmol) in dichloromethane (10 mL). After stirring at −78° C. for 15 minutes, the reaction mixture was gradually warmed to room temperature over 1 hour, and stirred at room temperature for 2 hours. It was then cooled to −78° C., quenched with anhydrous methanol (15 mL), and allowed to warm to room temperature. Solvents were removed in vacuo, and the residue was treated with methanol (20 mL) and heated at reflux for 30 minutes. The reaction mixture was cooled and concentrated under reduced pressure; the residue was partitioned between dichloromethane and water. The aqueous layer was adjusted to a pH of 14 with 1 N aqueous sodium hydroxide solution, then extracted with additional dichloromethane. The aqueous layer was brought to pH 6-7 by addition of 1 N aqueous hydrochloric acid and stirred for 10 minutes; the resulting precipitate was isolated via filtration, affording the product as an off-white solid. Yield: 599 mg, 2.80 mmol, 86%. LCMS m/z 215.1 [M+H$^+$]. $^1$H NMR (400 MHz, CD$_3$OD) δ 8.97 (s, 1H), 6.74-6.89 (m, 3H), 2.33 (s, 3H), 2.07 (s, 3H), 1.91 (s, 3H).

Step 8. Synthesis of 4-[4-(3,5-dimethylpyridazin-4-yl)-3-methylphenoxy]-1-{[2-(trimethylsilyl)ethoxy]methyl}-1H-pyrrolo[8,2-c]pyridine (C47)

C46 was converted to the product using the method described for synthesis of C15 in Example 2. In this case, purification was carried out via silica gel chromatography (Mobile phase A: dichloromethane; Mobile phase B: 80:20:1 dichloromethane/methanol/concentrated ammonium hydroxide solution; Gradient: 0% to 25% B). The product was obtained as a yellow gum. Yield: 67 mg, 0.15 mmol, 65%. LCMS m/z 461.3 [M+H$^+$]. $^1$H NMR (400 MHz, CDCl$_3$) δ 8.98 (s, 1H), 7.94 (d, J=5.7 Hz, 1H), 7.16-7.26 (m, 4H), 7.00 (d, J=8.2 Hz, 1H), 6.68-6.72 (m, 1H), 5.50 (s, 2H), 3.47-3.55 (m, 2H), 2.42 (s, 3H), 2.07 (s, 3H), 1.98 (s, 3H), 0.87-0.95 (m, 2H), −0.04 (s, 9H).

Step 9. Synthesis of 4-[4-(3,5-dimethylpyridazin-4-yl)-3-methylphenoxy]-1H-pyrrolo[8,2-c]pyridine, ENT-1 (11) and 4-[4-(3,5-dimethylpyridazin-4-yl)-3-methylphenoxy]-1H-pyrrolo[3,2-c]pyridine, ENT-2 (12)

Tetrabutylammonium fluoride (1 M solution in tetrahydrofuran, 1 mL, 1 mmol) was added to a solution of C47 (44.9 mg, 97.5 μmol) in tetrahydrofuran (1 mL), and the reaction mixture was heated at 80° C. for 2 hours. The reaction mixture was cooled and extracted with ethyl acetate. The combined organic layers were washed with water and with saturated aqueous sodium chloride solution, then dried over magnesium sulfate, filtered, and concentrated in vacuo. Purification using high-performance liquid chromatography (Column: Princeton Silica, 5 μm; Gradient: 5% to 100% ethanol in heptane) was followed by atropenantiomer separation via supercritical fluid chromatography (Column: Chiral Technologies, Chiralpak AS-H, 5 μm; Eluent: 3:1 carbon dioxide/methanol). The first-eluting atropenantiomer was designated as compound 11, obtained as a solid. Yield: 4.1 mg, 12 μmol, 12%. LCMS m/z 331.2 [M+H$^+$]. $^1$H NMR (400 MHz, CDCl$_3$) δ 8.99 (s, 1H), 8.72 (br s, 1H), 7.91 (d, J=5.9 Hz, 1H), 7.23-7.27 (m, 2H), 7.21 (br dd, J=8.2, 2.3 Hz, 1H), 7.14 (dd, J=5.8, 0.9 Hz, 1H), 7.01 (d, J=8.2 Hz, 1H), 6.72-6.74 (m, 1H), 2.43 (s, 3H), 2.07 (s, 3H), 1.99 (s, 3H). Retention time: 4.43 minutes (Column: Chiral Technologies, Chiralpak AS-H, 250×4.6 mm, 5 μm; Eluent: 3:1 carbon dioxide/methanol; Flow rate: 2.5 mL/minute).

The second-eluting atropenantiomer, designated as compound 12, was also obtained as a solid. Yield: 4.5 mg, 14 μmol, 14%. LCMS m/z 331.2 [M+H$^+$]. $^1$H NMR (400 MHz, CDCl$_3$) δ 8.99 (s, 1H), 8.73 (br s, 1H), 7.91 (d, J=5.9 Hz, 1H), 7.23-7.27 (m, 2H), 7.21 (br dd, J=8.3, 2.4 Hz, 1H), 7.14 (dd, J=5.9, 1.0 Hz, 1H), 7.01 (d, J=8.2 Hz, 1H), 6.71-6.74 (m, 1H), 2.43 (s, 3H), 2.07 (s, 3H), 1.99 (s, 3H). Retention time: 6.74 minutes (HPLC conditions identical to those described for compound 11).

Example 13

4-[4-(4,6-Dimethyl-1-oxidopyrimidin-5-yl)-3-methylphenoxy]-1H-pyrazolo[4,3-c]pyridine (13)

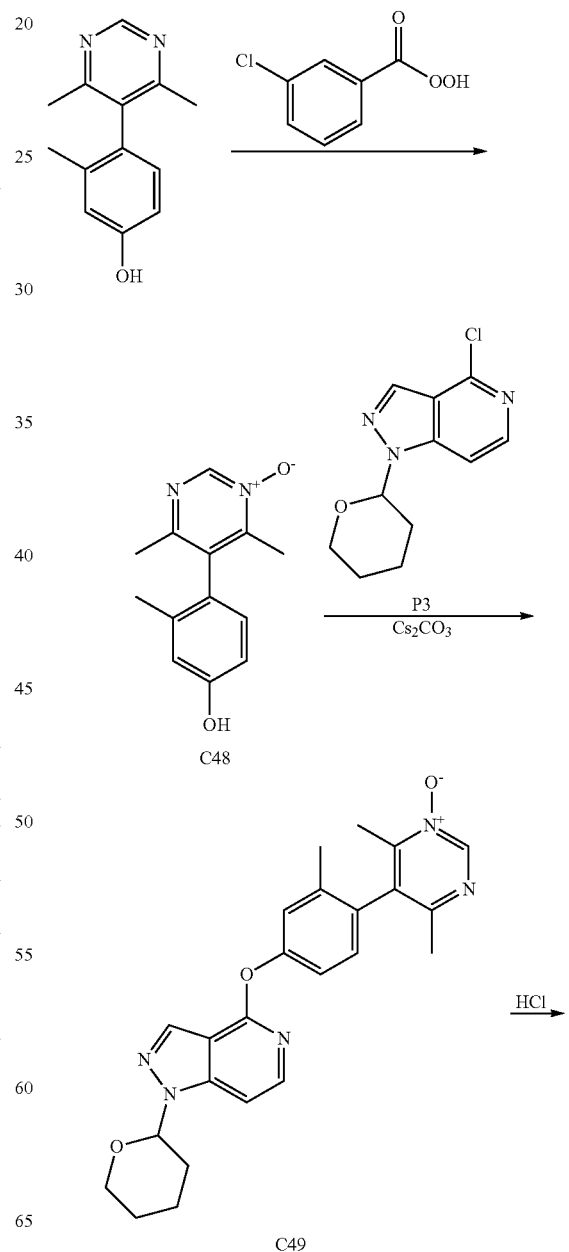

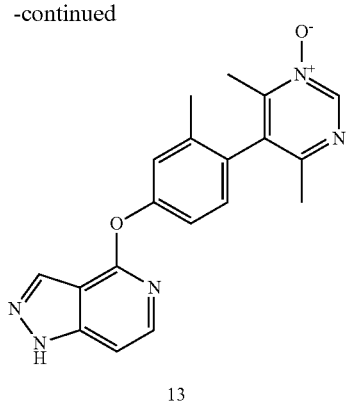

13

Step 1. Synthesis of 4-(4,6-dimethyl-1-oxidopyrimidin-5-yl)-3-methylphenol (C48)

To a solution of 4-(4,6-dimethylpyrimidin-5-yl)-3-methylphenol (1.0 g, 4.7 mmol) in dichloromethane (25 mL) was added 3-chloroperoxybenzoic acid (887 mg, 5.14 mmol) at 0° C. The reaction was stirred at 0° C. for 2 hours, then at room temperature for 14 hours. After removal of solvent in vacuo, purification by chromatography on silica gel (Gradient: 0% to 100% ethyl acetate in petroleum ether) provided the product. Yield: 742 mg, 3.22 mmol, 69%. $^1$H NMR (400 MHz, CDCl$_3$) δ 9.03 (s, 1H), 6.82-6.91 (m, 3H), 2.30 (s, 3H), 2.22 (s, 3H), 1.97 (s, 3H).

Step 2. Synthesis of 4-[4-(4,6-dimethyl-1-oxidopyrimidin-5-yl)-3-methylphenoxy]-1-(tetrahydro-2H-pyran-2-yl)-1H-pyrazolo[4,3-c]pyridine (C49)

To a solution of C48 (230 mg, 1.0 mmol) in acetonitrile (25 mL) were added P3 (238 mg, 1.00 mmol) and cesium carbonate (650 mg, 2.0 mmol), and the reaction mixture was stirred at 110° C. for 60 hours. The reaction mixture was filtered and concentrated in vacuo; silica gel chromatography (Gradient: 0% to 5% methanol in dichloromethane) afforded the product as a yellow solid. Yield: 290 mg, 0.67 mmol, 67%.

Step 3. Synthesis of 4-[4-(4,6-dimethyl-1-oxidopyrimidin-5-yl)-3-methylphenoxy]-1H-pyrazolo[4,3-c]pyridine (13)

A solution of hydrogen chloride in 1,4-dioxane (10 mL) was added to C49 (290 mg, 0.67 mmol) at 0° C. The reaction mixture was stirred for 2 hours at room temperature, and then concentrated in vacuo. The residue was neutralized with aqueous ammonium hydroxide solution until the pH reached 9. After removal of solvent under reduced pressure, purification was carried out via preparative thin layer chromatography on silica gel (Eluent: 10:1 dichloromethane/methanol) to provide the product as a white solid. Yield: 70 mg, 0.20 mmol, 30%. LCMS m/z 347.9 [M+H$^+$]. $^1$H NMR (400 MHz, CD$_3$OD) δ 9.05 (s, 1H), 8.15 (s, 1H), 7.85 (d, J=6.0 Hz, 1H), 7.33 (br s, 1H), 7.29 (d, J=5.5 Hz, 1H), 7.24-7.26 (m, 2H), 2.33 (s, 3H), 2.30 (s, 3H), 2.09 (s, 3H).

Method A

Coupling of N-protected 4-chloro-1H-pyrrolo[3,2-c]pyridines or 4-chloro-1H-pyrazolo[4,3-c]pyridines with phenols Method A describes a specific method for preparations of certain compounds of the invention.

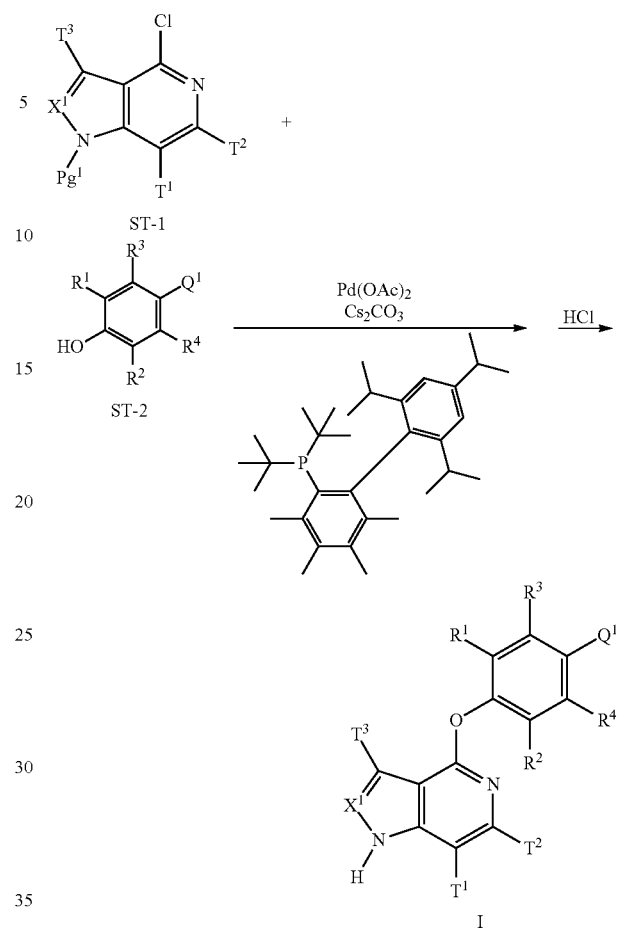

An N-protected compound of Formula ST-1 wherein Pg$^1$ is a protecting group (e.g., P2 or P3) (0.11 mmol) in degassed 1,4-dioxane (1 mL) was added to a phenol of Formula ST-2 (0.1 mmol) in a 2-dram vial. Cesium carbonate (~98 mg, 0.3 mmol), palladium(II) acetate (~2.5 mg, 10 μmol) and di-tert-butyl[3,4,5,6-tetramethyl-2',4',6'-tri(propan-2-yl)biphenyl-2-yl]phosphane (~10 mg, 20 μmol) were added, and the reaction mixture was degassed twice using sequential vacuum and nitrogen fill. The vial was shaken and heated at 80° C. for 20 hours, then cooled to room temperature. The reaction mixture was partitioned between water (1.5 mL) and ethyl acetate (2.5 mL) and filtered through Celite; the organic layer was passed through a 6 mL solid-phase extraction cartridge filled with sodium sulfate. The aqueous layer was extracted twice via the same procedure, and the combined filtrates from the sodium sulfate cartridges were concentrated in vacuo. The residue was dissolved in dichloromethane (0.5 mL) and treated with hydrogen chloride in 1,4-dioxane (4 M, 0.5 mL, 2 mmol). This reaction mixture was shaken at room temperature for 66 hours, then diluted with ethyl acetate (2.5 mL) and quenched with aqueous sodium hydroxide solution (6 N, 0.35 mL) and water (1 mL). The organic layer was passed through a 6 mL solid-phase extraction cartridge filled with sodium sulfate. The aqueous layer was extracted twice via the same procedure, and the combined filtrates from the sodium sulfate cartridges were concentrated in vacuo. Purification was carried out using reversed phase high-performance liquid chromatography (Column: Waters XBridge C18, 5 μm; Mobile phase A: 0.03% ammonium hydroxide in water (v/v); Mobile phase B: 0.03% ammonium hydroxide in acetonitrile (v/v); Gradient: 10% to 100% B) to provide the product.

TABLE 1

Examples 14-29

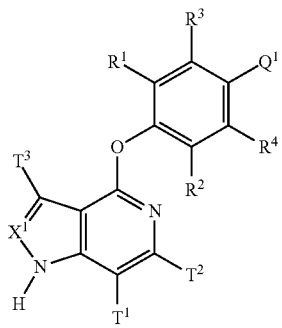

X¹ = CT⁴;
each of T¹, T², T³, and T⁴ is H

| Example Number | [R¹/R²/R³/R⁴/Q¹ structure] | Method of Preparation; Non-commercial Starting Materials | ¹H NMR (400 MHz, CDCl₃) δ (ppm); Mass spectrum, observed ion m/z [M + H⁺] or HPLC retention time (minutes); Mass spectrum m/z [M + H⁺] (unless otherwise indicated) |
|---|---|---|---|
| 14 | imidazo[1,2-a]pyrazine with 2-methylphenoxy | Example 1[1,2,3] | 9.72 (br s, 1H), 9.07 (s, 1H), 7.88 (d, J = 5.8 Hz, 1H), 7.71 (d, J = 1.0 Hz, 1H), 7.32-7.34 (m, 1H), 7.27-7.29 (m, 2H), 7.26 (dd, J = 3.1, 2.3 Hz, 1H), 7.15 (dd, J = 5.8, 0.8 Hz, 1H), 7.07-7.09 (m, 1H), 6.73-6.76 (m, 1H), 2.34 (s, 3H), 2.03 (s, 3H); 356.0 |
| 15 | imidazo[1,2-a]pyrazine with 2-methylphenoxy | Example 1[4] | 9.62 (br s, 1H), 9.16 (s, 1H), 7.89 (d, J = 6.0 Hz, 1H), 7.81-7.84 (m, 2H), 7.41 (d, J = 8.3 Hz, 1H), 7.25-7.34 (m, 4H), 7.14 (d, J = 6.0 Hz, 1H), 6.77-6.81 (m, 1H), 2.14 (s, 3H); 342.2 |
| 16 | methylpyrimidine-CN with fluorophenoxy | Example 2; C13 | ¹H NMR (400 MHz, CD₃OD) δ 9.19 (s, 1H), 7.79 (d, J = 5.8 Hz, 1H), 7.51 (dd, J = 9.3, 8.0 Hz, 1H), 7.36 (d, J = 3.0 Hz, 1H), 7.30 (d, J = 6.0 Hz, 1H), 7.14-7.20 (m, 2H), 6.57 (d, J = 3.3 Hz, 1H), 2.53 (s, 3H); 345.9 |

TABLE 1-continued

| | | | |
|---|---|---|---|
| 17 | 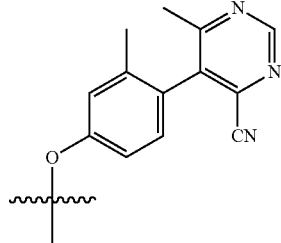 [SMILES: *Oc1ccc(-c2c(C)ncnc2C#N)c(C)c1] | Example 16 | ¹H NMR (400 MHz, CD₃OD) δ 9.18 (s, 1H), 7.76 (d, J = 5.8 Hz, 1H), 7.31 (d, J = 3.3 Hz, 1H), 7.25-7.28 (m, 2H), 7.20 (br d, J = 2.5 Hz, 1H), 7.12 (br dd, J = 8.3, 2.3 Hz, 1H), 6.47 (dd, J = 3.3, 0.8 Hz, 1H), 2.44 (s, 3H), 2.10 (br s, 3H); 342.0 |
| 18 | 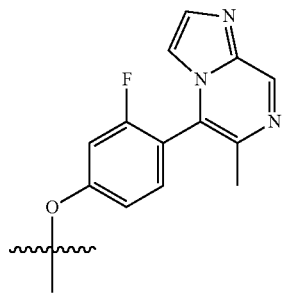 [SMILES: *Oc1ccc(-c2c(C)ncc3nccn23)c(F)c1] | Example 1[1,2] | 9.10 (s, 1H), 8.68 (br s, 1H), 7.95 (d, J = 5.8 Hz, 1H), 7.75 (d, J = 1.0 Hz 1H), 7.46 (dd, J = 8.8, 7.8 Hz, 1H), 7.36-7.38 (m, 1H), 7.25-7.32 (m, 3H, assumed; partially obscured by solvent peak), 7.21 (dd, J = 5.8, 1.0 Hz, 1H), 6.77-6.79 (m, 1H), 2.46 (s, 3H); 360.1 |
| 19 | 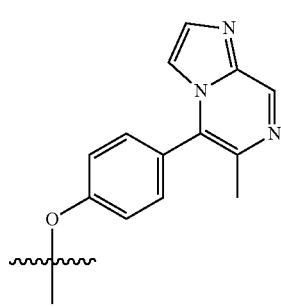 [SMILES: *Oc1ccc(-c2c(C)ncc3nccn23)cc1] | Example 5[1,5] | 9.11 (br s, 1H), 9.10 (s, 1H), 7.91 (d, J = 5.8 Hz, 1H), 7.74 (br s, 1H), 7.49 (s, 4H), 7.40 (br s, 1H), 7.26-7.29 (m, 1H, assumed; partially obscured by solvent peak), 7.18 (br d, J = 5.8 Hz, 1H), 6.74-6.78 (m, 1H), 2.46 (s, 3H); 342.0 |
| 20 | 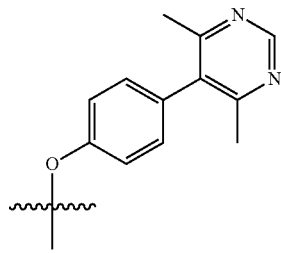 [SMILES: *Oc1ccc(-c2c(C)ncnc2C)cc1] | Examples 9 and 10[6,3] | 9.64-9.80 (br m, 1H), 8.94 (s, 1H), 7.85 (br d, J = 5.8 Hz, 1H), 7.36 (br d, J = 8.6 Hz, 2H), 7.17-7.22 (m, 3H), 7.12 (br d, J = 5.7 Hz, 1H), 6.65-6.68 (m, 1H), 2.29 (s, 6H); 317.1 |
| 21 | 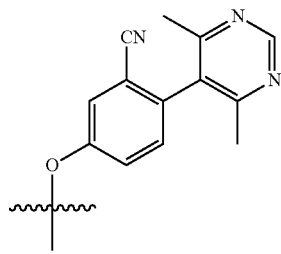 [SMILES: *Oc1ccc(-c2c(C)ncnc2C)c(C#N)c1] | Example 5[7]; P2[8] | 9.04 (s, 1H), 8.72 (br s, 1H), 7.91 (d, J = 5.9 Hz, 1H), 7.76 (dd, J = 2.5, 0.4 Hz, 1H), 7.66 (dd, J = 8.5, 2.5 Hz, 1H), 7.33 (dd, J = 8.5, 0.3 Hz, 1H), 7.29 (dd, J = 3.3, 2.3 Hz, 1H), 7.20 (dd, J = 5.9, 1.0 Hz, 1H), 6.76 (ddd, J = 3.3, 2.0, 1.0 Hz, 1H), 2.36 (s, 6H); 342.2 |
| 22 | 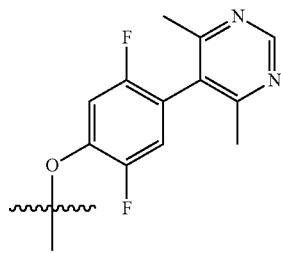 [SMILES: *Oc1cc(F)c(-c2c(C)ncnc2C)cc1F] | Example 5[9,3] | ¹H NMR (600 MHz, DMSO-d₆) δ 8.96 (s, 1H), 7.69 (d, J = 5.7 Hz, 1H), 7.55-7.60 (m, 2H), 7.48 (dd, J = 3.1, 2.6 Hz, 1H), 7.23 (br d, J = 6 Hz, 1H), 6.64-6.66 (m, 1H), 2.30 (s, 6H); 353.1 |

TABLE 1-continued
| 23 | 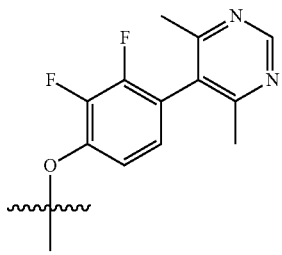 [SMILES: *Oc1ccc(-c2c(C)ncnc2C)c(F)c1F] | Example 6; P2[10] | $^1$H NMR (600 MHz, DMSO-d[6]) δ 8.98 (s, 1H), 7.69 (d, J = 5.7 Hz, 1H), 7.48-7.50 (m, 1H), 7.36-7.40 (m, 1H), 7.27-7.31 (m, 1H), 7.24 (br d, J = 5.7 Hz, 1H), 6.65-6.68 (m, 1H), 2.29 (s, 6H); 353.2 |
| --- | --- | --- | --- |
| 24 | 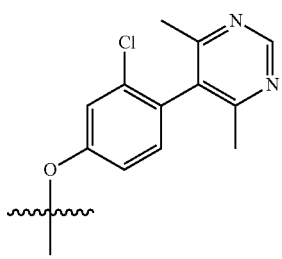 [SMILES: *Oc1ccc(-c2c(C)ncnc2C)c(Cl)c1] | Method A | 2.02 minutes[11]; 351.1, 353.1 |
| 25 | 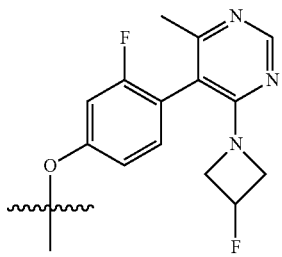 [SMILES: *Oc1ccc(-c2c(C)ncnc2N2CC(F)C2)c(F)c1] | Method A | 2.33 minutes[12]; 394.2 |
| 26 | 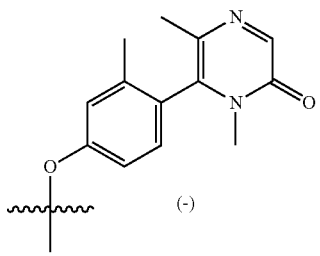 [SMILES: *Oc1ccc(-c2c(C)ncc(=O)n2C)c(C)c1] | Example 6; P2, P8[13] | $^1$H NMR (400 MHz, CD[3]OD) δ 8.09 (s, 1H), 7.73 (d, J = 5.9 Hz, 1H), 7.33 (d, J = 3.2 Hz, 1H), 7.23-7.28 (m, 2H), 7.19-7.21 (m, 1H), 7.13 (br dd, J = 8.2, 2.3 Hz, 1H), 6.54-6.56 (m, 1H), 3.28 (s, 3H), 2.12 (s, 3H), 2.06 (s, 3H); 347.1 |

TABLE 1-continued

| # | Structure | Example | Data |
|---|---|---|---|
| 27 | (+) atropenantiomer | Example 6; P2, P8[14] | $^1$H NMR (400 MHz, CD$_3$OD) δ 8.09 (s, 1H), 7.73 (d, J = 5.8 Hz, 1H), 7.33 (d, J = 3.1 Hz, 1H), 7.23-7.28 (m, 2H), 7.19-7.21 (m, 1H), 7.13 (br dd, J = 8.5, 2.4 Hz, 1H), 6.54-6.56 (m, 1H), 3.28 (s, 3H), 2.13 (s, 3H), 2.06 (s, 3H); 347.1 |
| 28 | 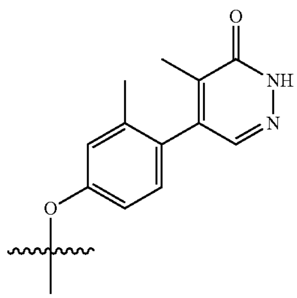 [SMILES: *Oc1ccc(-c2cn[nH]c(=O)c2C)c(C)c1] | Example 6; P2, C41[15] | $^1$H NMR (600 MHz, DMSO-d$_6$) δ 7.70 (d, J = 5.7 Hz, 1H), 7.68 (s, 1H), 7.42 (dd, J = 2.8, 2.6 Hz, 1H), 7.18-7.20 (m, 2H), 7.17 (br d, J = 2.2 Hz, 1H), 7.09 (dd, J = 8.3, 2.4 Hz, 1H), 6.54-6.56 (m, 1H), 2.11 (s, 3H), 1.86 (s, 3H); 333.0 |
| 29 | 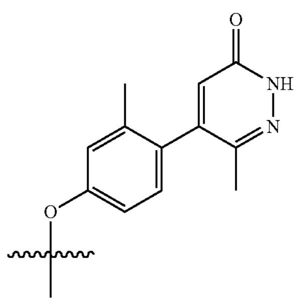 [SMILES: *Oc1ccc(-c2cc(=O)[nH]nc2C)c(C)c1] | Examples 3 and 4[16] | $^1$H NMR (400 MHz, CD$_3$OD) δ 7.72 (d, J = 6.1 Hz, 1H), 7.32 (d, J = 3.1 Hz, 1H), 7.23 (dd, J = 6.0, 0.9 Hz, 1H), 7.18 (d, J = 8.2 Hz, 1H), 7.10-7.12 (m, 1H), 7.05 (br dd, J = 8.3, 2.4 Hz, 1H), 6.76 (d, J = 0.4 Hz, 1H), 6.51 (dd, J = 3.1, 1.0 Hz, 1H), 2.16 (br s, 3H), 2.11 (d, J = 0.4 Hz, 3H); 333.2 |

[1] The requisite 5-bromo-6-methylimidazo[1,2-a]pyrazine was prepared via the method of A. R. Harris et al., Tetrahedron 2011, 67, 9063-9066.

[2] In the penultimate step, the coupling was carried out using tetrakis(triphenylphosphine)palladium(0) and sodium carbonate.

[3] The final deprotection was effected with tetrabutylammonium fluoride.

[4] The requisite 4-(imidazo[1,2-a]pyrazin-5-yl)-3-methylphenol was prepared by the general method used for synthesis of C28 in Example 5.

[5] The final deprotection was carried out using trifluoroacetic acid, followed by treatment with potassium carbonate.

[6] 4-(4,6-Dimethylpyrimidin-5-yl)phenol was prepared using the method described in Example 5.

[7] The final deprotection was carried out with trifluoroacetic acid.

[8] 5-Bromo-4,6-dimethylpyrimidine was converted to 4,6-dimethyl-5-(4,4,5,5-tetramethyl-1,3,2-dioxaborolan-2-yl)pyrimidine using the general method described for preparation of C20 in Examples 3 and 4. This compound was converted to the requisite 2-(4,6-dimethylpyrimidin-5-yl)-5-hydroxybenzonitrile via Suzuki reaction with 2-bromo-5-methoxybenzonitrile and deprotection according to the general method given in Example 5 for synthesis of C28.

[9] The requisite 4-(4,6-dimethylpyrimidin-5-yl)-2,5-difluorophenol was prepared via Suzuki reaction between (2,5-difluoro-4-methoxyphenyl)boronic acid and 5-bromo-4,6-dimethylpyrimidine, mediated by tetrakis(triphenylphosphine)palladium(0), followed by demethylation using boron tribromide.

[10] Suzuki reaction between 5-bromo-4,6-dimethylpyrimidine and (2,3-difluoro-4-methoxyphenyl)boronic acid was mediated via tris(dibenzylideneacetone)dipalladium(0) and tricyclohexylphosphine; deprotection with boron tribromide afforded the requisite 4-(4,6-dimethylpyrimidin-5-yl)-2,3-difluorophenol.

[11] Conditions for analytical HPLC. Column: Waters Atlantis dC18, 4.6 × 50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute.

[12] Conditions for analytical HPLC. Column: Waters XBridge C18, 4.6 × 50 mm, 5 μm; Mobile phase A: 0.03% ammonium hydroxide in water (v/v); Mobile phase B: 0.03% ammonium hydroxide in acetonitrile (v/v); Gradient: 5.0% to 95% B, linear over 4.0 minutes; Flow rate: 2 mL/minute).

[13] The racemic product was separated using supercritical fluid chromatography (Column: Chiral Technologies Chiralcel OJ-H, 5 μm; Eluent: 1:4 methanol/carbon dioxide). Atropenantiomer Example 26 was the first-eluting isomer, exhibiting a negative (−) rotation, and a retention time of 4.28 minutes (Column: Chiral Technologies Chiralcel OJ-H, 4.6 × 250 mm, 5 μm; Eluent: 1:4 methanol/carbon dioxide; Flow rate 2.5 mL/min).

[14] The racemic product was separated as described in footnote 13. Atropenantiomer Example 27 was the second-eluting isomer, exhibiting a positive (+) rotation and a retention time of 4.97 minutes (analytical conditions identical to those in footnote 13).

[15] Compound C41 was reacted with C20, using conditions similar to those employed for preparation of C27 in Example 5. The resulting 5-[4-(benzyloxy)-2-methylphenyl]-4-methyl-2-(tetrahydro-2H-pyran-2-yl)pyridazin-3(2H)-one was hydrogenated to provide 5-(4-hydroxy-2-methylphenyl)-4-methyl-2-(tetrahydro-2H-pyran-2-yl)pyridazin-3(2H)-one.

[16] 2-Methyl-5-oxo-2,5-dihydrofuran-3-yl trifluoromethanesulfonate was prepared from ethyl 4-bromo-3-oxopentanoate using the general methods outlined for preparation of C19 in Examples 3 and 4.

TABLE 2

Examples 30-43

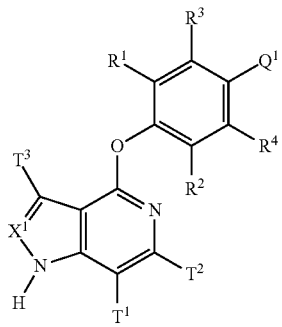

$X^1 = N$;
each of $T^1$, $T^2$, and $T^3$ is H

| Example Number | (structure with R¹, R², R³, R⁴, Q¹) | Method of Preparation; Non-commercial Starting Materials | ¹H NMR (400 MHz, CDCl₃) δ (ppm); Mass spectrum, observed ion m/z [M + H⁺] or HPLC retention time (minutes); Mass spectrum m/z [M + H⁺] (unless otherwise indicated) |
|---|---|---|---|
| 30 | (2-methyl-4-(2-methylimidazo[4,5-c]pyridin-1-yl)phenoxy) | Examples 11 and 12¹; P6² | ¹H NMR (400 MHz, CDCl₃) δ 9.10 (s, 1H), 8.41 (d, J = 5.5 Hz, 1H), 8.26 (s, 1H), 7.94 (d, J = 6.0 Hz, 1H), 7.40 (br d, J = 2.5 Hz, 1H), 7.35 (br dd, half of ABX pattern, J = 8.5, 2.4 Hz, 1H), 7.30 (d, half of AB quartet, J = 8.6 Hz, 1H), 7.25-7.29 (m, 1 H, assumed; partially obscured by solvent peak), 7.01 (dd, J = 5.5, 0.8 Hz, 1H), 2.49 (s, 3H), 2.00 (s, 3H); 357.2 |
| 31 | (2-methyl-4-(6-methyl-3-oxo-2,3-dihydropyridazin-4-yl)phenoxy) | Examples 3 and 4³ | 8.11 (br s, 1H), 7.83 (d, J = 6.3 Hz, 1H), 7.23-7.28 (m, 3H), 7.17-7.21 (m, 1H), 6.79-6.80 (m, 1H), 2.20 (br s, 3H), 2.13 (d, J = 0.4 Hz, 3H); 334.2 |
| 32 | (4-(4,6-dimethylpyrimidin-5-yl)-2-fluorophenoxy) | Example 5; P6⁴ | ¹H NMR (400 MHz, CDCl₃) δ 9.00 (s, 1H), 8.27 (s, 1H), 8.00 (d, J = 6.0 Hz, 1H), 7.19-7.28 (m, 4H, assumed; partially obscured by solvent peak), 2.38 (s, 6H); 336.1 |

TABLE 2-continued
| | | | |
|---|---|---|---|
| 33 | 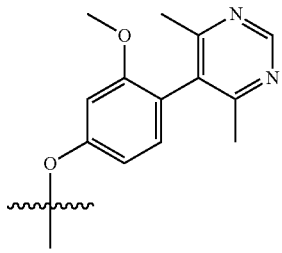 [SMILES: *Oc1ccc(-c2c(C)ncnc2C)c(OC)c1] | Example 5; P6[5] | 9.27 (s, 1H), 8.08 (d, J = 6.5 Hz, 1H), 7.62-7.69 (m, 1H), 7.58 (s, 1H), 7.45-7.55 (m, 2H), 7.27-7.33 (m, 1H), 3.84 (s, 3H), 2.55 (s, 6H); 348.1 |
| 34 | 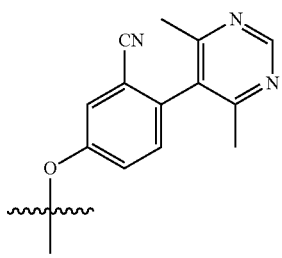 [SMILES: *Oc1ccc(-c2c(C)ncnc2C)c(C#N)c1] | Example 5[6]; P6[7] | $^1$H NMR (400 MHz, CDCl$_3$) δ 9.05 (s, 1H), 8.30 (d, J = 0.8 Hz, 1H), 7.97 (d, J = 6.0 Hz, 1H), 7.84 (d, J = 2.5 Hz, 1H), 7.70 (dd, J = 8.5, 2.5 Hz, 1H), 7.39 (d, J = 8.5 Hz, 1H), 7.24 (dd, J = 6.0, 1.0 Hz, 1H), 2.37 (s, 6H); 343.1 |
| 35 | 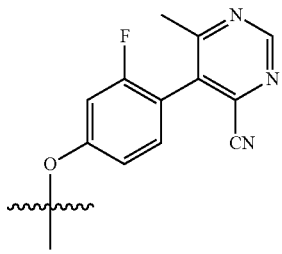 [SMILES: *Oc1ccc(-c2c(C)ncnc2C#N)c(F)c1] | Example 5[8]; P3[9] | $^1$H NMR (600 MHz, DMSO-d$_6$) δ 9.33 (s, 1H), 8.31 (br s, 1H), 7.91 (dd, J = 5.9, 0.4 Hz, 1H), 7.73 (dd, J = 8.6, 8.6 Hz, 1H), 7.56 (dd, J = 10.8, 2.2 Hz, 1H), 7.39 (dd, J = 8.4, 2.2 Hz, 1H), 7.36 (br d, J = 5.9 Hz, 1H), 2.48 (s, 3H); 347.2 |
| 36 | 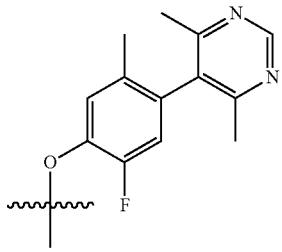 [SMILES: *Oc1cc(C)c(-c2c(C)ncnc2C)cc1F] | Method A | 2.33 minutes; 350.1[10] |
| 37 | 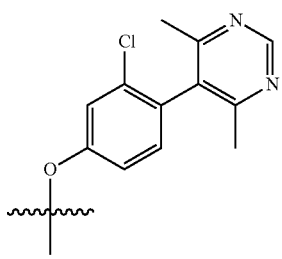 [SMILES: *Oc1ccc(-c2c(C)ncnc2C)c(Cl)c1] | Method A | 2.40 minutes; 352.1[10] |

TABLE 2-continued

| # | Structure | Source | NMR / MS |
|---|---|---|---|
| 38 | 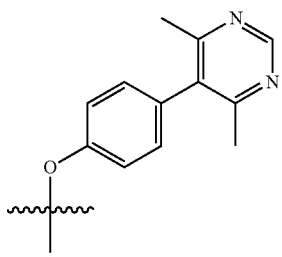 [SMILES: *Oc1ccc(-c2c(C)ncnc2C)cc1] | Example 5; P6 | $^1$H NMR (400 MHz, CDCl$_3$) δ 8.97 (s, 1H), 8.23 (s, 1H), 7.98 (d, J = 6.0 Hz, 1H), 7.42 (br d, J = 8.5 Hz, 2H), 7.24-7.29 (m, 2H, assumed; partially obscured by solvent peak), 7.17 (d, J = 6.0 Hz, 1H), 2.35 (s, 6H); 318.1 |
| 39 | 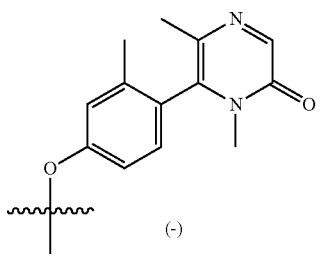 [SMILES: *Oc1ccc(-c2c(C)ncc(=O)n2C)c(C)c1] (−) | Example 6; P8[11] | 8.18 (s, 1H), 8.10 (s, 1H), 7.85 (d, J = 6.2 Hz, 1H), 7.32-7.36 (m, 2H), 7.25-7.30 (m, 2H), 3.29 (s, 3H), 2.16 (s, 3H), 2.07 (s, 3H); 348.4 |
| 40 | 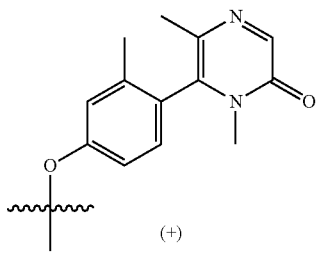 [SMILES: *Oc1ccc(-c2c(C)ncc(=O)n2C)c(C)c1] (+) | Example 6; | 8.17-8.18 (m, 1H), 8.10 (s, 1H), 7.85 (d, J = 6.1 Hz, 1H), 7.32-7.36 (m, 2H), 7.25-7.30 (m, 2H), 3.29 (s, 3H), 2.16 (s, 3H), 2.07 (s, 3H); 348.4 |
| 41 | 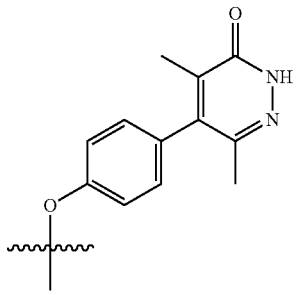 [SMILES: *Oc1ccc(-c2c(C)n[nH]c(=O)c2C)cc1] | Examples 3 and 4 | 8.12 (s, 1H), 7.86 (d, J = 6.2 Hz, 1H), 7.37 (br AB quartet, J$_{AB}$ = 8.6 Hz, Δν$_{AB}$ = 28 Hz, 4H), 7.28 (d, J = 5.8 Hz, 1H), 2.11 (s, 3H), 1.99 (s, 3H); 334.2 |
| 42 | 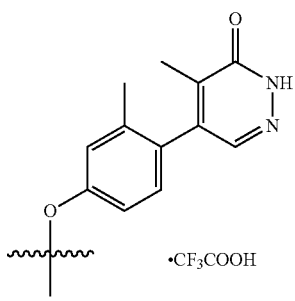 [SMILES: *Oc1ccc(-c2cn[nH]c(=O)c2C)c(C)c1 ; "·CF3COOH"] ·CF$_3$COOH | Examples 3 and 4[13,14] | $^1$H NMR (600 MHz, DMSO-d$_6$) δ 8.23 (br s, 1H), 7.84 (d, J = 6.2 Hz, 1H), 7.72 (s, 1H), 7.26-7.30 (m, 2H), 7.25 (d, half of AB quartet, J = 7.9 Hz, 1H), 7.19 (dd, half of ABX pattern, J = 7.9, 2.2 Hz, 1H), 2.13 (s, 3H), 1.86 (s, 3H); 334.0 |

TABLE 2-continued

| | | | |
|---|---|---|---|
| 43 | 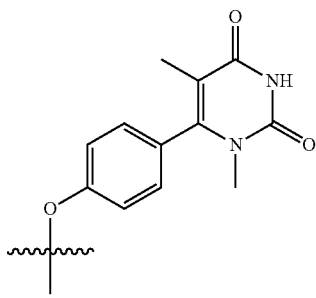 [SMILES: *Oc1ccc(-c2c(C)c(=O)[nH]c(=O)n2C)cc1] | Example 8 | 8.18 (d, J = 1.0 Hz, 1H), 7.85 (d, J = 6.1 Hz, 1H), 7.42-7.47 (m, 4H), 7.29 (dd, J = 6.1, 1.0 Hz, 1H), 3.11 (s, 3H), 1.71 (s, 3H); 350.2 |

[1]In the penultimate step, the coupling was carried out using 4,5-bis(diphenylphosphino)-9,9-dimethylxanthene rather than di-tert-butyl[3,4,5,6-tetramethyl-2',4',6-tri(propan-2-yl)biphenyl-2-yl]phosphane.

[2]The requisite 3-methyl-4-(2-methyl-1H-imidazo[4,5-c]pyridin-1-yl)phenol was prepared in the following manner: reaction of 4-methoxy-2-methylaniline with 4-chloro-3-nitropyridine provided N-(4-methoxy-2-methylphenyl)-3-nitropyridin-4-amine. After hydrogenation of the nitro group, the resulting amine was cyclized with ethyl orthoacetate and acetic anhydride to afford 1-(4-methoxy-2-methylphenyl)-2-methyl-1H-imidazo[4,5-c]pyridine, which was demethylated with boron tribromide.

[3]2-Methyl-5-oxo-2,5-dihydrofuran-3-yl trifluoromethanesulfonate was prepared from ethyl 4-bromo-3-oxopentanoate using the general methods outlined for preparation of C19 in Examples 3 and 4.

[4]1-Bromo-2-fluoro-4-methoxybenzene was converted to intermediate 5-(2-fluoro-4-methoxyphenyl)-4,6-dimethylpyrimidine using the procedure described for synthesis of C14 in Example 1.

[5]4-Bromo-3-methoxyphenol was protected as its [tri(propan-2-yl)]silane ether, and subsequently converted to [3-methoxy-4-(4,4,5,5-tetramethyl-1,3,2-dioxaborolan-2-yl)phenoxy][tri(propan-2-yl)]silane with [1,1'-bis(diphenylphosphino)ferrocene]dichloropalladium(II) catalyst. This was reacted with 5-bromo-4,6-dimethylpyrimidine using the conditions described for synthesis of C27 in Example 5 to afford 5-(2-methoxy-4-{[tri(propan-2-yl)silyl]oxy}phenyl)-4,6-dimethylpyrimidine; deprotection with tetraethylammonium fluoride provided the requisite 4-(4,6-dimethylpyrimidin-5-yl)-3-methoxyphenol.

[6]The final deprotection was carried out with trifluoroacetic acid, followed by treatment with sodium acetate in methanol.

[7]2-Bromo-5-hydroxybenzonitrile was protected as its [tri(propan-2-yl)]silane ether. Reaction with 4,6-dimethyl-5-(4,4,5,5-tetramethyl-1,3,2-dioxaborolan-2-yl)pyrimidine (prepared from 5-bromo-4,6-dimethylpyrimidine using the conditions described for synthesis of C13 in Example 1) according to the method used for preparation of C14 in Example 1 provided the requisite 2-(4,6-dimethylpyrimidin-5-yl)-5-hydroxybenzonitrile.

[8]The final deprotection was carried out with hydrochloric acid.

[9]5-Bromo-6-methylpyrimidine-4-carbonitrile was prepared from 5-bromo-4-chloro-6-methylpyrimidine via reaction with potassium cyanide and 1,4,7,10,13,16-hexaoxacyclooctadecane. 4-Bromo-3-fluorophenol was converted to [3-fluoro-4-(4,4,5,5-tetramethyl-1,3,2-dioxaborolan-2-yl)phenoxy][tri(propan-2-yl)]silane using the conditions outlined in footnote 5. These two reagents were subjected to Suzuki reaction and desilylation as described in footnote 5, affording 5-(2-fluoro-4-hydroxyphenyl)-6-methylpyrimidine-4-carbonitrile.

[10]Conditions for analytical HPLC. Column: Waters Atlantis dC18, 4.6 × 50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute.

[11]The racemic product was separated using supercritical fluid chromatography (Column: Chiral Technologies Chiralcel OJ-H, 5 μm; Eluent: 1:4 methanol/carbon dioxide). Atropenantiomer Example 39 was the first-eluting isomer, exhibiting a negative (−) rotation, and a retention time of 2.91 minutes (Column: Chiral Technologies Chiralcel OJ-H, 4.6 × 250 mm, 5 μm; Eluent: 1:4 methanol/carbon dioxide; Flow rate 2.5 mL/min).

[12]The racemic product was separated as described in footnote 11. Atropenantiomer Example 40 was the second-eluting isomer, exhibiting a positive (+) rotation and a retention time of 3.28 minutes (analytical conditions identical to those in footnote 11).

[13]In the penultimate step, the coupling was carried out using copper(I) iodide and cesium carbonate in pyridine at 100° C.

[14]Compound C41 was reacted with C20, using conditions similar to those employed for preparation of C27 in Example 5. The resulting 5-[4-(benzyloxy)-2-methylphenyl]-4-methyl-2-(tetrahydro-2H-pyran-2-yl)pyridazin-3(2H)-one was hydrogenated to provide 5-(4-hydroxy-2-methylphenyl)-4-methyl-2-(tetrahydro-2H-pyran-2-yl)pyridazin-3(2H)-one.

TABLE 3

Examples 44-47

| Example Number | Structure | Method of Preparation; Non-commercial Starting Materials | 1H NMR (400 MHz, CDCl3) δ (ppm); Mass spectrum, observed ion m/z [M + H+] |
|---|---|---|---|
| 44 | 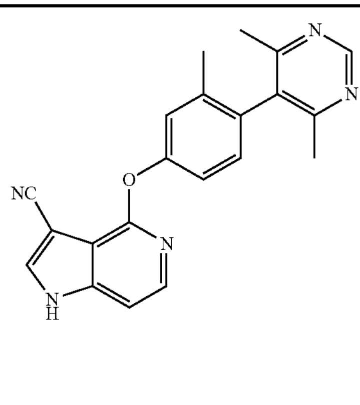 | Example 5; P7[1] | 9.44 (br s, 1H), 8.98 (s, 1H), 8.00 (d, J = 5.5 Hz, 1H), 7.79 (br d, J = 2 Hz, 1H), 7.32-7.35 (m, 1H), 7.27-7.31 (m, 1H, assumed; partially obscured by solvent peak), 7.16 (d, J = 5.5 Hz, 1H), 7.09 (d, J = 8.0 Hz, 1H), 2.27 (s, 6H), 2.04 (s, 3H); 355.9 |

TABLE 3-continued

Examples 44-47

| Example Number | Structure | Method of Preparation; Non-commercial Starting Materials | $^1$H NMR (400 MHz, CDCl$_3$) δ (ppm); Mass spectrum, observed ion m/z [M + H$^+$] |
|---|---|---|---|
| 45 | 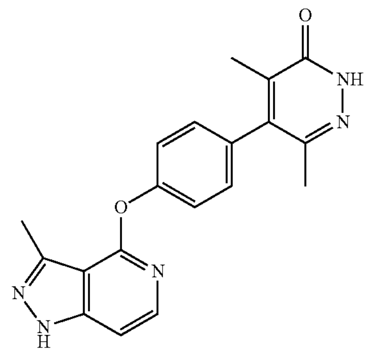 [SMILES: Cc1n[nH]c(=O)c(C)c1-c1ccc(Oc2nccc3[nH]nc(C)c23)cc1] | Examples 3 and 4$^2$ | 7.78 (d, J = 6.2 Hz, 1H), 7.35 (br AB quartet, J$_{AB}$ = 8.7 Hz, Δν$_{AB}$ = 25.9 Hz, 4H), 7.18 (d, J = 6.2 Hz, 1H), 2.73 (s, 3H), 2.10 (s, 3H), 1.99 (s, 3H); 348.3 |
| 46 | 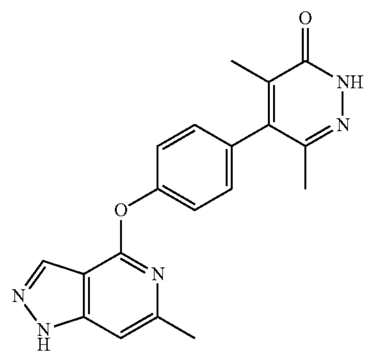 [SMILES: Cc1cc2[nH]ncc2c(Oc2ccc(-c3c(C)n[nH]c(=O)c3C)cc2)n1] | Examples 3 and 4; P4 | 7.79 (d, J = 0.6 Hz, 1H), 7.37 (br AB quartet, J$_{AB}$ = 8.8 Hz, Δν$_{AB}$ = 34.9 Hz, 4H), 7.09-7.11 (m, 1H), 2.47 (d, J = 0.8 Hz, 3H), 2.10 (s, 3H), 1.99 (s, 3H); 348.1 |
| 47 | 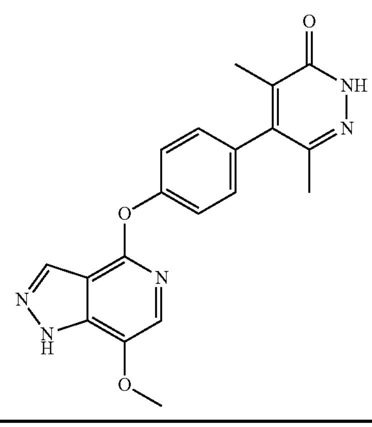 | Examples 3 and 4; P5 | $^1$H NMR (600 MHz, DMSO-d$_6$) δ 8.16 (br s, 1H), 7.50 (s, 1H), 7.32 (br AB quartet, J$_{AB}$ = 8.3 Hz, Δν$_{AB}$ = 19.3 Hz, 4H), 3.97 (s, 3H), 1.97 (s, 3H), 1.83 (s, 3H); 364.0 |

$^1$The final deprotection was carried out with trifluoroacetic acid, followed by treatment with sodium acetate in methanol.
$^2$4-Chloro-3-methyl-1-(tetrahydro-2H-pyran-2-yl)-1H-pyrazolo[4,3-c]pyridine was prepared using the method described in Preparation P3.

Example AA

Human D1 Receptor Binding Assay and Data

The affinity of the compounds described herein was determined by competition binding assays similar to those described in Ryman-Rasmussen et al., "Differential activation of adenylate cyclase and receptor internalization by novel dopamine D1 receptor agonists", *Molecular Pharmacology* 68(4):1039-1048 (2005). This radioligand binding assay used [$^3$H]-SCH23390, a radiolabeled D1 ligand, to evaluate the ability of a test compound to compete with the radioligand when binding to a D1 receptor.

D1 binding assays were performed using over-expressing LTK human cell lines. To determine basic assay parameters, ligand concentrations were determined from saturation binding studies where the K$_d$ for [$^3$H]-SCH23390 was found to be 1.3 nM. From tissue concentration curve studies, the optimal amount of tissue was determined to be 1.75 mg/mL per 96 well plate using 0.5 nM of [$^3$H]-SCH23390. These ligand and tissue concentrations were used in time course studies to determine linearity and equilibrium conditions for binding.

Binding was at equilibrium with the specified amount of tissue in 30 minutes at 37° C. From these parameters, $K_i$ values were determined by homogenizing the specified amount of tissue for each species in 50 mM Tris (pH 7.4 at 4° C.) containing 2.0 mM $MgCl_2$ using a Polytron and spun in a centrifuge at 40,000×g for 10 minutes. The pellet was resuspended in assay buffer [50 mM Tris (pH 7.4@ RT) containing 4 mM $MgSO_4$ and 0.5 mM EDTA]. Incubations were initiated by the addition of 200 µL of tissue to 96-well plates containing test drugs (2.5 µL) and 0.5 nM [$^3$H]-SCH23390 (50 µL) in a final volume of 250 µL. Non-specific binding was determined by radioligand binding in the presence of a saturating concentration of (+)-Butaclamol (10 µM), a D1 antagonist. After a 30 minute incubation period at 37° C., assay samples were rapidly filtered through Unifilter-96 GF/B PEI-coated filter plates and rinsed with 50 mM Tris buffer (pH 7.4 at 4° C.). Membrane bound [$^3$H]-SCH23390 levels were determined by liquid scintillation counting of the filterplates in Ecolume. The $IC_{50}$ value (concentration at which 50% inhibition of specific binding occurs) was calculated by linear regression of the concentration-response data in Microsoft Excel. $K_i$ values were calculated according to the Cheng-Prusoff equation:

$$K_i = \frac{IC_{50}}{1 + ([L]/K_d)}$$

where [L]=concentration of free radioligand and $K_d$=dissociation constant of radioligand for D1 receptor (1.3 nM for [$^3$H]-SCH23390).

Example BB

D1 cAMP HTRF Assay and Data

The D1 cAMP (Cyclic Adenosine Monophosphate) HTRF (Homogeneous Time-Resolved Fluorescence) Assay used and described herein is a competitive immunoassay between native cAMP produced by cells and cAMP labeled with XL-665. This assay was used to determine the ability of a test compound to agonize (including partially agonize) D1. A Mab anti-cAMP labeled Cryptate visualizes the tracer. The maximum signal is achieved if the samples do not contain free cAMP due to the proximity of donor (Eu-cryptate) and acceptor (XL665) entities. The signal, therefore, is inversely proportional to the concentration of cAMP in the sample. A time-resolved and ratiometric measurement (em 665 nm/em 620 nm) minimizes the interference with medium. cAMP HTRF assays are commercially available, for example, from Cisbio Bioassays, IBA group.

Materials and Methods
Materials:
The cAMP Dynamic kit was obtained from Cisbio International (Cisbio 62AM4PEJ). Multidrop Combi (Thermo Scientific) was used for assay additions. An EnVision (PerkinElmer) reader was used to read HTRF.

Cell Culture:
A HEK293T/hD1#1 stable cell line was constructed internally (Pfizer Ann Arbor). The cells were grown as adherent cells in $NuncT_{500}$ flasks in high glucose DMEM (Invitrogen 11995-065), 10% fetal bovine serum dialyzed (Invitrogen 26400-044), 1×MEM NEAA (Invitrogen 1140, 25 mM HEPES (Invitrogen 15630), 1× Pen/Strep (Invitrogen 15070-063) and 500 µg/mL Genenticin (Invitrogen 10131-035) at 37° C. and 5% $CO_2$. At 72 or 96 hours post-growth, cells were rinsed with DPBS, and 0.25% Trypsin-EDTA was added to dislodge the cells. Media was then added and cells were centrifuged and media removed. The cell pellets were re-suspended in Cell Culture Freezing Medium (Invitrogen 12648-056) at a density of 4e7 cells/mL. One mL aliquots of the cells were made in Cryo-vials and frozen at −80° C. for future use in the D1HTRF assay.

D1 cAMP HTRF Assay Procedure:
Frozen cells were quickly thawed, re-suspended in 50 mL warm media and allowed to sit for 5 min prior to centrifugation (1000 rpm) at room temperature. Media was removed and cell pellet was re-suspended in PBS/0.5 µM IBMX generating 2e5 cells/mL. Using a Multidrop Combi, 5 µL cells/well was added to the assay plate (Greiner 784085), which already contained 5 µL of a test compound. Compound controls [5 µM dopamine (final) and 0.5% DMSO (final)] were also included on every plate for data analysis. Cells and compounds were incubated at room temperature for 30 min. Working solutions of cAMP-D2 and anti-cAMP-cryptate were prepared according to Cisbio instructions. Using Multidrop, 5 µL cAMP-D2 working solution was added to the assay plate containing the test compound and cells. Using Multidrop, 5 µL anti-cAMP-cryptate working solutions was added to assay plate containing test compound, cells and cAMP-D2. The assay plate was incubated for 1 hour at room temperature. The assay plate was read on an EnVision plate reader using Cisbio recommended settings. A cAMP standard curve was generated using cAMP stock solution provided in the Cisbio kit.

Data Analysis:
Data analysis was done using computer software. Percent effects were calculated from the compound controls. Ratio $EC_{50}$ was determined using the raw ratio data from the EnVision reader. The cAMP standard curve was used in an analysis program to determine cAMP concentrations from raw ratio data. cAMP $EC_{50}$ was determined using the calculated cAMP data.

TABLE 4

Biological Data for Examples 1-47

| Example Number | Compound IUPAC Name | Human D1 Receptor Binding, $K_i$ (µM); Geometric mean of 2-3 determinations | Human D1 cAMP HTRF, $EC_{50}$ (µM); Geometric mean of 2-6 determinations |
|---|---|---|---|
| 1 | 4-[4-(4,6-dimethylpyrimidin-5-yl)-3-fluorophenoxy]-1H-pyrrolo[3,2-c]pyridine | 0.0303[c] | 0.176[a] |
| 2 | 4-[4-(1,4-dimethyl-1H-pyrazol-5-yl)-3-methylphenoxy]-1H-pyrrolo[3,2-c]pyridine | 0.0348[b] | 0.355 |

TABLE 4-continued

Biological Data for Examples 1-47

| Example Number | Compound IUPAC Name | Human D1 Receptor Binding, $K_i$ (μM); Geometric mean of 2-3 determinations | Human D1 cAMP HTRF, $EC_{50}$ (μM); Geometric mean of 2-6 determinations |
|---|---|---|---|
| 3 | (+)-4,6-dimethyl-5-[2-methyl-4-(1H-pyrazolo[4,3-c]pyridin-4-yloxy)phenyl]pyridazin-3(2H)-one | 0.00976 | 0.0151 |
| 4 | (−)-4,6-dimethyl-5-[2-methyl-4-(1H-pyrazolo[4,3-c]pyridin-4-yloxy)phenyl]pyridazin-3(2H)-one | 0.0104 | 0.0105 |
| 5 | 4-[4-(4,6-dimethylpyrimidin-5-yl)-3-methylphenoxy]-1H-pyrrolo[3,2-c]pyridine | $0.0130^c$ | $0.146^a$ |
| 6 | 4-[4-(4,6-dimethylpyrimidin-5-yl)-3-methylphenoxy]-1H-pyrazolo[4,3-c]pyridine | $0.113^c$ | $0.568^a$ |
| 7 | 4,6-dimethyl-5-[4-(1H-pyrrolo[3,2-c]pyridin-4-yloxy)phenyl]pyridazin-3(2H)-one | 0.00412 | $0.0192^a$ |
| 8 | (−)-1,5-dimethyl-6-[2-methyl-4-(1H-pyrazolo[4,3-c]pyridin-4-yloxy)phenyl]pyrimidine-2,4(1H,3H)-dione | 0.00183 | $<0.00222^a$ |
| 9 | 4,6-dimethyl-5-[2-methyl-4-(1H-pyrrolo[3,2-c]pyridin-4-yloxy)phenyl]pyridazin-3(2H)-one, ENT-1 | 0.00487 | $0.00733^a$ |
| 10 | 4,6-dimethyl-5-[2-methyl-4-(1H-pyrrolo[3,2-c]pyridin-4-yloxy)phenyl]pyridazin-3(2H)-one, ENT-2 | 0.00504 | 0.00431 |
| 11 | 4-[4-(3,5-dimethylpyridazin-4-yl)-3-methylphenoxy]-1H-pyrrolo[3,2-c]pyridine, ENT-1 | $0.0141^b$ | 0.117 |
| 12 | 4-[4-(3,5-dimethylpyridazin-4-yl)-3-methylphenoxy]-1H-pyrrolo[3,2-c]pyridine, ENT-2 | $0.0883^b$ | 0.520 |
| 13 | 4-[4-(4,6-dimethyl-1-oxidopyrimidin-5-yl)-3-methylphenoxy]-1H-pyrazolo[4,3-c]pyridine | $0.0931^b$ | 0.260 |
| 14 | 6-methyl-5-[2-methyl-4-(1H-pyrrolo[3,2-c]pyridin-4-yloxy)phenyl]imidazo[1,2-a]pyrazine | $0.00798^c$ | 0.137 |
| 15 | 5-[2-methyl-4-(1H-pyrrolo[3,2-c]pyridin-4-yloxy)phenyl]imidazo[1,2-a]pyrazine | 0.0975 | 0.417 |
| 16 | 5-[2-fluoro-4-(1H-pyrrolo[3,2-c]pyridin-4-yloxy)phenyl]-6-methylpyrimidine-4-carbonitrile | 0.0283 | 0.396 |
| 17 | 6-methyl-5-[2-methyl-4-(1H-pyrrolo[3,2-c]pyridin-4-yloxy)phenyl]pyrimidine-4-carbonitrile | 0.0392 | 0.374 |
| 18 | 5-[2-fluoro-4-(1H-pyrrolo[3,2-c]pyridin-4-yloxy)phenyl]-6-methylimidazo[1,2-a]pyrazine | $0.0294^c$ | 0.141 |
| 19 | 6-methyl-5-[4-(1H-pyrrolo[3,2-c]pyridin-4-yloxy)phenyl]imidazo[1,2-a]pyrazine | 0.0159 | $0.464^a$ |
| 20 | 4-[4-(4,6-dimethylpyrimidin-5-yl)phenoxy]-1H-pyrrolo[3,2-c]pyridine | 0.0443 | 0.238 |
| 21 | 2-(4,6-dimethylpyrimidin-5-yl)-5-(1H-pyrrolo[3,2-c]pyridin-4-yloxy)benzonitrile | 0.102 | 0.247 |
| 22 | 4-[4-(4,6-dimethylpyrimidin-5-yl)-2,5-difluorophenoxy]-1H-pyrrolo[3,2-c]pyridine | 0.0548 | 0.538 |
| 23 | 4-[4-(4,6-dimethylpyrimidin-5-yl)-2,3-difluorophenoxy]-1H-pyrrolo[3,2-c]pyridine | $0.0538^c$ | $0.590^a$ |
| 24 | 4-[3-chloro-4-(4,6-dimethylpyrimidin-5-yl)phenoxy]-1H-pyrrolo[3,2-c]pyridine | 0.00984 | 0.102 |
| 25 | 4-{3-fluoro-4-[4-(3-fluoroazetidin-1-yl)-6-methylpyrimidin-5-yl]phenoxy}-1H-pyrrolo[3,2-c]pyridine | 0.00509 | 0.156 |
| 26 | (−)-1,5-dimethyl-6-[2-methyl-4-(1H-pyrrolo[3,2-c]pyridin-4-yloxy)phenyl]pyrazin-2(1H)-one | 0.00456 | 0.0730 |
| 27 | (+)-1,5-dimethyl-6-[2-methyl-4-(1H-pyrrolo[3,2-c]pyridin-4-yloxy)phenyl]pyrazin-2(1H)-one | 0.0106 | 0.0646 |
| 28 | 4-methyl-5-[2-methyl-4-(1H-pyrrolo[3,2-c]pyridin-4-yloxy)phenyl]pyridazin-3(2H)-one | 0.0357 | 0.0549 |
| 29 | 6-methyl-5-[2-methyl-4-(1H-pyrrolo[3,2-c]pyridin-4-yloxy)phenyl]pyridazin-3(2H)-one | $0.0679^b$ | 0.119 |
| 30 | 4-[3-methyl-4-(2-methyl-1H-imidazo[4,5-c]pyridin-1-yl)phenoxy]-1H-pyrazolo[4,3-c]pyridine | $0.268^b$ | 2.76 |
| 31 | 6-methyl-5-[2-methyl-4-(1H-pyrazolo[4,3-c]pyridin-4-yloxy)phenyl]pyridazin-3(2H)-one | $0.287^b$ | 0.548 |
| 32 | 4-[4-(4,6-dimethylpyrimidin-5-yl)-3-fluorophenoxy]-1H-pyrazolo[4,3-c]pyridine | $0.0723^b$ | $0.903^a$ |
| 33 | 4-[4-(4,6-dimethylpyrimidin-5-yl)-3-methoxyphenoxy]-1H-pyrazolo[4,3-c]pyridine | $0.124^b$ | $2.08^a$ |
| 34 | 2-(4,6-dimethylpyrimidin-5-yl)-5-(1H-pyrazolo[4,3-c]pyridin-4-yloxy)benzonitrile | $0.391^b$ | 2.38 |
| 35 | 5-[2-fluoro-4-(1H-pyrazolo[4,3-c]pyridin-4-yloxy)phenyl]-6-methylpyrimidine-4-carbonitrile | $0.0696^b$ | 1.34 |
| 36 | 4-[4-(4,6-dimethylpyrimidin-5-yl)-2-fluoro-5-methylphenoxy]-1H-pyrazolo[4,3-c]pyridine | $0.118^b$ | 0.733 |
| 37 | 4-[3-chloro-4-(4,6-dimethylpyrimidin-5-yl)phenoxy]-1H-pyrazolo[4,3-c]pyridine | 0.0523 | $0.248^a$ |

TABLE 4-continued

Biological Data for Examples 1-47

| Example Number | Compound IUPAC Name | Human D1 Receptor Binding, $K_i$ (μM); Geometric mean of 2-3 determinations | Human D1 cAMP HTRF, $EC_{50}$ (μM); Geometric mean of 2-6 determinations |
|---|---|---|---|
| 38 | 4-[4-(4,6-dimethylpyrimidin-5-yl)phenoxy]-1H-pyrazolo[4,3-c]pyridine | $0.129^b$ | $2.52^a$ |
| 39 | (−)-1,5-dimethyl-6-[2-methyl-4-(1H-pyrazolo[4,3-c]pyridin-4-yloxy)phenyl]pyrazin-2(1H)-one | $0.0418^c$ | $0.168^a$ |
| 40 | (+)-1,5-dimethyl-6-[2-methyl-4-(1H-pyrazolo[4,3-c]pyridin-4-yloxy)phenyl]pyrazin-2(1H)-one | $0.0281^b$ | 0.674 |
| 41 | 4,6-dimethyl-5-[4-(1H-pyrazolo[4,3-c]pyridin-4-yloxy)phenyl]pyridazin-3(2H)-one | $0.0409^c$ | $0.127^a$ |
| 42 | 4-methyl-5-[2-methyl-4-(1H-pyrazolo[4,3-c]pyridin-4-yloxy)phenyl]pyridazin-3(2H)-one, trifluoroacetate salt | 0.123 | 0.340 |
| 43 | 1,5-dimethyl-6-[4-(1H-pyrazolo[4,3-c]pyridin-4-yloxy)phenyl]pyrimidine-2,4(1H,3H)-dione | 0.0175 | 0.0282 |
| 44 | 4-[4-(4,6-dimethylpyrimidin-5-yl)-3-methylphenoxy]-1H-pyrrolo[3,2-c]pyridine-3-carbonitrile | 0.00460 | $0.0553^a$ |
| 45 | 4,6-dimethyl-5-{4-[(3-methyl-1H-pyrazolo[4,3-c]pyridin-4-yl)oxy]phenyl}pyridazin-3(2H)-one | 0.0103 | $0.0663^a$ |
| 46 | 4,6-dimethyl-5-{4-[(6-methyl-1H-pyrazolo[4,3-c]pyridin-4-yl)oxy]phenyl}pyridazin-3(2H)-one | 0.0247 | 0.0891 |
| 47 | 5-{4-[(7-methoxy-1H-pyrazolo[4,3-c]pyridin-4-yl)oxy]phenyl}-4,6-dimethylpyridazin-3(2H)-one | $0.695^b$ | 1.30 |

$^a$Value represents the geometric mean of ≥7 determinations.
$^b$Value represents a single determination.
$^c$Value represents the geometric mean of ≥4 determinations.

Various modifications of the invention, in addition to those described herein, will be apparent to those skilled in the art from the foregoing description. Such modifications are also intended to fall within the scope of the appendant claims. Each reference (including all patents, patent applications, journal articles, books, and any other publications) cited in the present application is hereby incorporated by reference in its entirety.

What is claimed is:
1. A compound of Formula I:

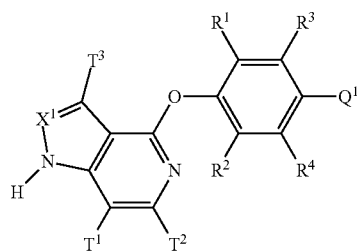

I or a pharmaceutically acceptable salt thereof, wherein:
each of $T^1$, $T^2$, $T^3$, and $T^4$ is independently selected from the group consisting of H, halogen, —CN, $C_{1-4}$ alkyl, $C_{1-4}$ haloalkyl, cyclopropyl, fluorocyclopropyl, $C_{1-4}$ alkoxy, $C_{1-4}$ haloalkoxy, and —C(═O)—O—($C_{1-4}$ alkyl);
$X^1$ is N or CH;
each of $R^1$ and $R^2$ is independently selected from the group consisting of H, halogen, —CN, $C_{1-4}$ alkyl, $C_{1-4}$ haloalkyl, $C_{1-4}$ alkoxy, $C_{1-4}$ haloalkoxy, and $C_{3-4}$ cycloalkyl;
each of $R^3$ and $R^4$ is independently selected from the group consisting of H, halogen, —OH, —CN, $C_{1-4}$ alkyl, $C_{1-4}$ haloalkyl, $C_{1-4}$ haloalkoxy, $C_{3-4}$ cycloalkyl, a 4- to 7-membered heterocycloalkyl, —N($R^5$)($R^6$), and —$OR^8$;
each of $R^5$ and $R^6$ independently is H or selected from the group consisting of $C_{1-4}$ alkyl, $C_{1-4}$ haloalkyl, and $C_{3-7}$ cycloalkyl;
or $R^5$ and $R^6$ together with the N atom to which they are attached form a 4- to 7-membered heterocycloalkyl or a 5-membered heteroaryl, each optionally substituted with 1, 2, or 3 substituents each independently selected from the group consisting of halogen, —CN, $C_{1-4}$ alkyl, $C_{1-4}$ alkoxy, $C_{3-6}$ cycloalkyl, $C_{1-4}$ haloalkyl, and $C_{1-4}$ haloalkoxy;
$R^8$ is selected from the group consisting of $C_{1-4}$ alkyl, $C_{3-6}$ cycloalkyl, a 4- to 7-membered heterocycloalkyl, phenyl, and a 5- to 6-membered heteroaryl, each optionally substituted with 1, 2, or 3 substituents each independently selected from the group consisting of halogen, —CN, $C_{1-4}$ alkyl, $C_{1-4}$ haloalkyl, $C_{3-6}$ cycloalkyl, $C_{1-4}$ alkoxy, and $C_{1-4}$ haloalkoxy;
$Q^1$ is a moiety of

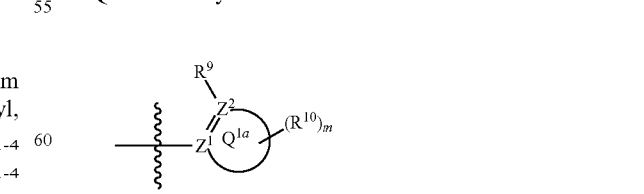

("Moiety $M^1$");
$Q^1$ or ring $Q^{1a}$ is an optionally substituted pyridinyl, pyrimidinyl, pyridazinyl, or pyrazinyl;
══ represents a single bond or double bond;

$Z^1$ is C;

$Z^2$ is C or N;

$R^9$ is $C_{1-4}$ alkyl, $C_{1-4}$ haloalkyl, $C_{3-7}$ cycloalkyl, —CN, —N($R^5$)($R^6$), $C_{1-6}$ alkoxy, $C_{1-6}$ haloalkoxy, or $C_{3-7}$ cycloalkoxy, wherein each of the $C_{1-4}$ alkyl and $C_{3-7}$ cycloalkyl is optionally substituted with 1, 2, 3, 4, or 5 substituents each independently selected from the group consisting of halogen, —N($R^5$)($R^6$), $C_{1-4}$ alkyl, $C_{1-4}$ haloalkyl, $C_{3-7}$ cycloalkyl, $C_{1-4}$ alkoxy, and $C_{1-4}$ haloalkoxy;

each $R^{10}$ is independently selected from the group consisting of halogen, —OH, —CN, —NO₂, oxo, thiono, $C_{1-6}$ alkyl, $C_{1-6}$ haloalkyl, $C_{1-6}$ hydroxylalkyl, $C_{1-6}$ alkoxy, $C_{1-6}$ haloalkoxy, $C_{3-7}$ cycloalkyl, $C_{2-6}$ alkenyl, $C_{2-6}$ alkynyl, $C_{6-10}$ aryl, a 4- to 10-membered heterocycloalkyl, a 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, (5- to 10-membered heteroaryl)-$C_{1-4}$ alkyl-, (5- to 10-membered heteroaryl)-$C_{2-4}$ alkenyl-, —N($R^5$)($R^6$), —N($R^7$)(C(=O)$R^8$), —S(=O)₂N($R^5$)($R^6$), —C(=O)—N($R^5$)($R^6$), —C(=O)—$R^8$, —C(=O)—$OR^8$, and —$OR^8$, wherein each of said $C_{1-6}$ alkyl, $C_{3-7}$ cycloalkyl, $C_{6-10}$ aryl, 4- to 10-membered heterocycloalkyl, 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, (5- to 10-membered heteroaryl)-$C_{1-4}$ alkyl-, and (5- to 10-membered heteroaryl)-$C_{2-4}$ alkenyl- is optionally substituted with 1, 2, 3 or 4 substituents each independently selected from the group consisting of halogen, OH, —CN, —NO₂, $C_{1-4}$ alkyl, $C_{1-4}$ hydroxyalkyl, $C_{1-4}$ alkoxy, —N($R^5$)($R^6$), —S—($C_{1-4}$ alkyl), —S(=O)₂—($C_{1-4}$ alkyl), $C_{6-10}$ aryloxy, ($C_{6-10}$ aryl)-$C_{1-4}$ alkyloxy- optionally substituted with 1 or 2 $C_{1-4}$ alkyl, oxo, —C(=O)H, —C(=O)—$C_{1-4}$ alkyl, —CO(=O)O—$C_{1-4}$ alkyl, —C(=O)NH₂, —NHC(=O)H, —NHC(=O)—($C_{1-4}$ alkyl), $C_{3-7}$ cycloalkyl, a 5- or 6-membered heteroaryl, $C_{1-4}$ haloalkyl, and $C_{1-4}$ haloalkoxy;

or $R^9$ and the adjacent $R^{10}$ together with the two ring atoms on ring $Q^{1a}$ to which they are attached form a fused benzene ring or a fused 5- or 6-membered heteroaryl, each optionally substituted with 1, 2, 3, 4, or 5 independently selected $R^{10a}$;

each $R^{10a}$ is independently selected from the group consisting of halogen, —OH, —C(=O)OH, —C(=O)—$C_{1-4}$ alkyl, —C(=O)—NH₂, —C(=O)—N($C_{1-4}$ alkyl)₂, —CN, $C_{1-4}$ alkyl, $C_{1-4}$ alkoxy, $C_{1-4}$ hydroxyalkyl, $C_{1-4}$ haloalkyl, and $C_{1-4}$ haloalkoxy; and m is 0, 1, 2, 3, or 4.

2. A compound of Formula I:

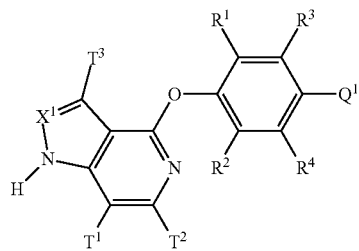

I or a pharmaceutically acceptable salt thereof, wherein:

each of $T^1$, $T^2$, $T^3$, and $T^4$ is independently selected from the group consisting of H, halogen, —CN, $C_{1-4}$ alkyl, $C_{1-4}$ haloalkyl, cyclopropyl, fluorocyclopropyl, $C_{1-4}$ alkoxy, $C_{1-4}$ haloalkoxy, and —C(=O)—O—($C_{1-4}$ alkyl);

$X^1$ is N or CH;

each of $R^1$ and $R^2$ is independently selected from the group consisting of H, halogen, —CN, $C_{1-4}$ alkyl, $C_{1-4}$ haloalkyl, $C_{1-4}$ alkoxy, $C_{1-4}$ haloalkoxy, and $C_{3-4}$ cycloalkyl;

each of $R^3$ and $R^4$ is independently selected from the group consisting of H, halogen, —OH, —CN, $C_{1-4}$ alkyl, $C_{1-4}$ haloalkyl, $C_{1-4}$ haloalkoxy, $C_{3-4}$ cycloalkyl, a 4- to 7-membered heterocycloalkyl, —N($R^5$)($R^6$), and —$OR^8$;

each of $R^5$ and $R^6$ independently is H or selected from the group consisting of $C_{1-4}$ alkyl, $C_{1-4}$ haloalkyl, and $C_{3-7}$ cycloalkyl;

or $R^5$ and $R^6$ together with the N atom to which they are attached form a 4- to 7-membered heterocycloalkyl or a 5-membered heteroaryl, each optionally substituted with 1, 2, or 3 substituents each independently selected from the group consisting of halogen, —CN, $C_{1-4}$ alkyl, $C_{1-4}$ alkoxy, $C_{3-6}$ cycloalkyl, $C_{1-4}$ haloalkyl, and $C_{1-4}$ haloalkoxy;

$R^8$ is selected from the group consisting of $C_{1-4}$ alkyl, $C_{3-6}$ cycloalkyl, a 4- to 7-membered heterocycloalkyl, phenyl, and a 5- to 6-membered heteroaryl, each optionally substituted with 1, 2, or 3 substituents each independently selected from the group consisting of halogen, —CN, $C_{1-4}$ alkyl, $C_{1-4}$ haloalkyl, $C_{3-6}$ cycloalkyl, $C_{1-4}$ alkoxy, and $C_{1-4}$ haloalkoxy;

$Q^1$ is a moiety of

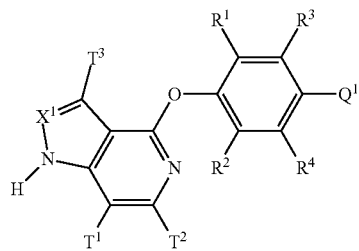

("Moiety $M^1$");

═══ represents a single bond or double bond;

$Z^1$ is C;

$Z^2$ is C or N;

Moiety $M^1$ is selected from the group consisting of quinolinyl, isoquinolinyl, 1H-imidazo[4,5-c]pyridinyl, imidazo[1,2-a]pyridinyl, 1H-pyrrolo[3,2-c]pyridinyl, imidazo[1,2-a]pyrazinyl, imidazo[2,1-c][1,2,4]triazinyl, imidazo[1,5-a]pyrazinyl, imidazo[1,2-a]pyrimidinyl, 1H-indazolyl, 9H-purinyl, imidazo[1,2-a]pyrimidinyl, [1,2,4]triazolo[1,5-a]pyrimidinyl, isoxazolo[5,4-c]pyridazinyl, isoxazolo[3,4-c]pyridazinyl, and [1,2,4]triazolo[4,3-b]pyridazinyl, each optionally substituted with 1, 2, or 3 $R^{10}$ and further optionally substituted with 1 or 2 $R^{10a}$; or wherein Moiety $M^1$ is selected from the group consisting of pyrimidinyl, pyrazinyl, pyridinyl, pyridazinyl, 1H-pyrazolyl, 1H-pyrrolyl, 4H-pyrazolyl, 3-oxo-2H-pyridazinyl, 1H-2-oxo-pyrimidinyl, 1H-2-oxo-pyridinyl, 2,4(1H,3H)-dioxo-pyrimidinyl, and 1H-2-oxo-pyrazinyl, each substituted with $R^9$ and further optionally substituted with 1, 2, or 3 $R^{10}$;

$R^9$ is $C_{1-4}$ alkyl, $C_{1-4}$ haloalkyl, $C_{3-7}$ cycloalkyl, —CN, —N($R^5$)($R^6$), $C_{1-6}$ alkoxy, $C_{1-6}$ haloalkoxy, or $C_{3-7}$ cycloalkoxy, wherein each of the $C_{1-4}$ alkyl and $C_{3-7}$ cycloalkyl is optionally substituted with 1, 2, 3, 4, or 5 substituents each independently selected from the group consisting of halogen, —N(R$^5$)(R$^6$), C$_{1-4}$ alkyl, C$_{1-4}$ haloalkyl, C$_{3-7}$ cycloalkyl, C$_{1-4}$ alkoxy, and C$_{1-4}$ haloalkoxy;

each R$^{10}$ is independently selected from the group consisting of halogen, —OH, —CN, —NO$_2$, oxo, thiono, C$_{1-6}$ alkyl, C$_{1-6}$ haloalkyl, C$_{1-6}$ hydroxylalkyl, C$_{1-6}$ alkoxy, C$_{1-6}$ haloalkoxy, C$_{3-7}$ cycloalkyl, C$_{2-6}$ alkenyl, C$_{2-6}$ alkynyl, C$_{6-10}$ aryl, a 4- to 10-membered heterocycloalkyl, a 5- to 10-membered heteroaryl, (C$_{3-7}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, (5- to 10-membered heteroaryl)-C$_{1-4}$ alkyl-, (5- to 10-membered heteroaryl)-C$_{2-4}$ alkenyl-, —N(R$^5$)(R$^6$), —N(R$^7$)(C(=O)R$^8$), —S(=O)$_2$N(R$^5$)(R$^6$), —C(=O)—N(R$^5$)(R$^6$), —C(=O)—R$^8$, —C(=O)—OR$^8$, and —OR$^8$, wherein each of said C$_{1-6}$ alkyl, C$_{3-7}$ cycloalkyl, C$_{6-10}$ aryl, 4- to 10-membered heterocycloalkyl, 5- to 10-membered heteroaryl, (C$_{3-7}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, (5- to 10-membered heteroaryl)-C$_{1-4}$ alkyl-, and (5- to 10-membered heteroaryl)-C$_{2-4}$ alkenyl- is optionally substituted with 1, 2, 3 or 4 substituents each independently selected from the group consisting of halogen, OH, —CN, —NO$_2$, C$_{1-4}$ alkyl, C$_{1-4}$ hydroxyalkyl, C$_{1-4}$ alkoxy, —N(R$^5$)(R$^6$), —S—(C$_{1-4}$ alkyl), —S(=O)$_2$—(C$_{1-4}$ alkyl), C$_{6-10}$ aryloxy, (C$_{6-10}$ aryl)-C$_{1-4}$ alkyloxy- optionally substituted with 1 or 2 C$_{1-4}$ alkyl, oxo, —C(=O)H, —C(=O)—C$_{1-4}$ alkyl, —CO(=O)O—C$_{1-4}$ alkyl, —C(=O)NH$_2$, —NHC(=O)H, —NHC(=O)—(C$_{1-4}$ alkyl), C$_{3-7}$ cycloalkyl, a 5- or 6-membered heteroaryl, C$_{1-4}$ haloalkyl, and C$_{1-4}$ haloalkoxy;

or R$^9$ and the adjacent R$^{10}$ together with the two ring atoms on ring Q$^{1a}$ to which they are attached form a fused benzene ring or a fused 5- or 6-membered heteroaryl, each optionally substituted with 1, 2, 3, 4, or 5 independently selected R$^{10a}$;

each R$^{10a}$ is independently selected from the group consisting of halogen, —OH, —C(=O)OH, —C(=O)—C$_{1-4}$ alkyl, —C(=O)—NH$_2$, —C(=O)—N(C$_{1-4}$ alkyl)$_2$, —CN, C$_{1-4}$ alkyl, C$_{1-4}$ alkoxy, C$_{1-4}$ hydroxyalkyl, C$_{1-4}$ haloalkyl, and C$_{1-4}$ haloalkoxy; and m is 0, 1, 2, 3, or 4.

3. A compound of Formula I:

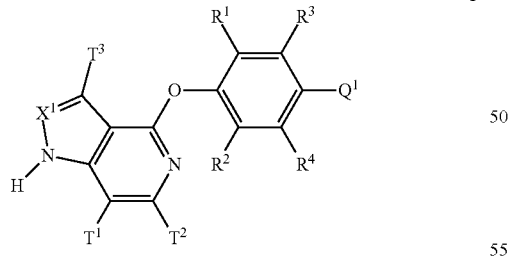

or a pharmaceutically acceptable salt thereof, wherein:
each of T$^1$, T$^2$, T$^3$, and T$^4$ is independently selected from the group consisting of H, halogen, —CN, C$_{1-4}$ alkyl, C$_{1-4}$ haloalkyl, cyclopropyl, fluorocyclopropyl, C$_{1-4}$ alkoxy, C$_{1-4}$ haloalkoxy, and —C(=O)—O—(C$_{1-4}$ alkyl);

X$^1$ is N or CH;

each of R$^1$ and R$^2$ is independently selected from the group consisting of H, halogen, —CN, C$_{1-4}$ alkyl, C$_{1-4}$ haloalkyl, C$_{1-4}$ alkoxy, C$_{1-4}$ haloalkoxy, and C$_{3-4}$ cycloalkyl;

each of R$^3$ and R$^4$ is independently selected from the group consisting of H, halogen, —OH, —CN, C$_{1-4}$ alkyl, C$_{1-4}$ haloalkyl, C$_{1-4}$ haloalkoxy, C$_{3-4}$ cycloalkyl, a 4- to 7-membered heterocycloalkyl, —N(R$^5$)(R$^6$), and —OR$^8$;

each of R$^5$ and R$^6$ independently is H or selected from the group consisting of C$_{1-4}$ alkyl, C$_{1-4}$ haloalkyl, and C$_{3-7}$ cycloalkyl;

or R$^5$ and R$^6$ together with the N atom to which they are attached form a 4- to 7-membered heterocycloalkyl or a 5-membered heteroaryl, each optionally substituted with 1, 2, or 3 substituents each independently selected from the group consisting of halogen, —CN, C$_{1-4}$ alkyl, C$_{1-4}$ alkoxy, C$_{3-6}$ cycloalkyl, C$_{1-4}$ haloalkyl, and C$_{1-4}$ haloalkoxy;

R$^8$ is selected from the group consisting of C$_{1-4}$ alkyl, C$_{3-6}$ cycloalkyl, a 4- to 7-membered heterocycloalkyl, phenyl, and a 5- to 6-membered heteroaryl, each optionally substituted with 1, 2, or 3 substituents each independently selected from the group consisting of halogen, —CN, C$_{1-4}$ alkyl, C$_{1-4}$ haloalkyl, C$_{3-6}$ cycloalkyl, C$_{1-4}$ alkoxy, and C$_{1-4}$ haloalkoxy;

Q$^1$ is a moiety of

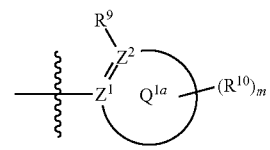

("Moiety M$^1$");

Moiety M$^1$ is

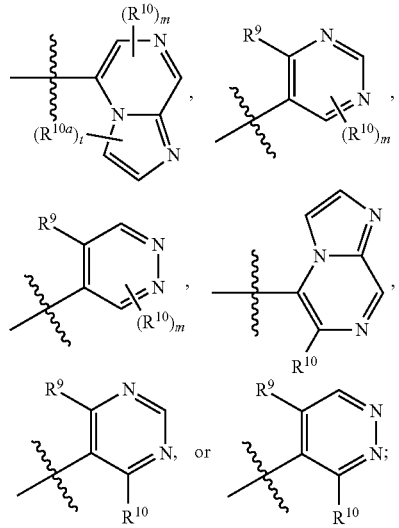

R$^9$ is C$_{1-4}$ alkyl, C$_{1-4}$ haloalkyl, C$_{3-7}$ cycloalkyl, —CN, —N(R$^5$)(R$^6$), C$_{1-6}$ alkoxy, C$_{1-6}$ haloalkoxy, or C$_{3-7}$ cycloalkoxy, wherein each of the C$_{1-4}$ alkyl and C$_{3-7}$ cycloalkyl is optionally substituted with 1, 2, 3, 4, or 5 substituents each independently selected from the group consisting of halogen, —N(R$^5$)(R$^6$), C$_{1-4}$ alkyl, C$_{1-4}$ haloalkyl, C$_{3-7}$ cycloalkyl, C$_{1-4}$ alkoxy, and C$_{1-4}$ haloalkoxy;

each R$^{10}$ is independently selected from the group consisting of halogen, —OH, —CN, —NO$_2$, oxo, thiono, C$_{1-6}$ alkyl, $C_{1-6}$ haloalkyl, $C_{1-6}$ hydroxylalkyl, $C_{1-6}$ alkoxy, $C_{1-6}$ haloalkoxy, $C_{3-7}$ cycloalkyl, $C_{2-6}$ alkenyl, $C_{2-6}$ alkynyl, $C_{6-10}$ aryl, a 4- to 10-membered heterocycloalkyl, a 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, (5- to 10-membered heteroaryl)-$C_{1-4}$ alkyl-, (5- to 10-membered heteroaryl)-$C_{2-4}$ alkenyl-, —N($R^5$)($R^6$), —N($R^7$)(C(=O)$R^8$), —S(=O)$_2$N($R^5$)($R^6$), —C(=O)—N($R^5$)($R^6$), —C(=O)—$R^8$, —C(=O)—O$R^8$, and —O$R^8$, wherein each of said $C_{1-6}$ alkyl, $C_{3-7}$ cycloalkyl, $C_{6-10}$ aryl, 4- to 10-membered heterocycloalkyl, 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, (5- to 10-membered heteroaryl)-$C_{1-4}$ alkyl-, and (5- to 10-membered heteroaryl)-$C_{2-4}$ alkenyl- is optionally substituted with 1, 2, 3 or 4 substituents each independently selected from the group consisting of halogen, OH, —CN, —NO$_2$, $C_{1-4}$ alkyl, $C_{1-4}$ hydroxyalkyl, $C_{1-4}$ alkoxy, —N($R^5$)($R^6$), —S—($C_{1-4}$ alkyl), —S(=O)$_2$—($C_{1-4}$ alkyl), $C_{6-10}$ aryloxy, ($C_{6-10}$ aryl)-$C_{1-4}$ alkyloxy- optionally substituted with 1 or 2 $C_{1-4}$ alkyl, oxo, —C(=O)H, —C(=O)—$C_{1-4}$ alkyl, —CO(=O)O—$C_{1-4}$ alkyl, —C(=O)NH$_2$, —NHC(=O)H, —NHC(=O)—($C_{1-4}$ alkyl), $C_{3-7}$ cycloalkyl, a 5- or 6-membered heteroaryl, $C_{1-4}$ haloalkyl, and $C_{1-4}$ haloalkoxy;

m is 0, 1, or 2;

$R^{10a}$ is $C_{1-4}$ alkyl, $C_{1-4}$ haloalkyl, or $C_{3-7}$ cycloalkyl; and t is 0 or 1.

4. A compound of Formula I:

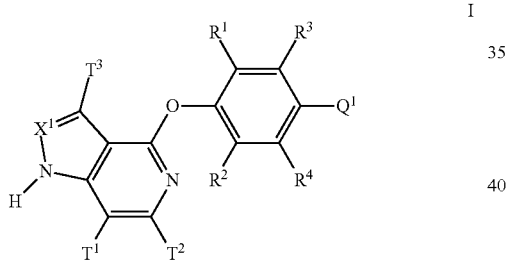

I or a pharmaceutically acceptable salt thereof, wherein:
each of $T^1$, $T^2$, $T^3$, and $T^4$ is independently selected from the group consisting of H, halogen, —CN, $C_{1-4}$ alkyl, $C_{1-4}$ haloalkyl, cyclopropyl, fluorocyclopropyl, $C_{1-4}$ alkoxy, $C_{1-4}$ haloalkoxy, and —C(=O)—O—($C_{1-4}$ alkyl);

$X^1$ is N or CH;

each of $R^1$ and $R^2$ is independently selected from the group consisting of H, halogen, —CN, $C_{1-4}$ alkyl, $C_{1-4}$ haloalkyl, $C_{1-4}$ alkoxy, $C_{1-4}$ haloalkoxy, and $C_{3-4}$ cycloalkyl;

each of $R^3$ and $R^4$ is independently selected from the group consisting of H, halogen, —OH, —CN, $C_{1-4}$ alkyl, $C_{1-4}$ haloalkyl, $C_{1-4}$ haloalkoxy, $C_{3-4}$ cycloalkyl, a 4- to 7-membered heterocycloalkyl, —N($R^5$)($R^6$), and —O$R^8$;

each of $R^5$ and $R^6$ independently is H or selected from the group consisting of $C_{1-4}$ alkyl, $C_{1-4}$ haloalkyl, and $C_{3-7}$ cycloalkyl;

or $R^5$ and $R^6$ together with the N atom to which they are attached form a 4- to 7-membered heterocycloalkyl or a 5-membered heteroaryl, each optionally substituted with 1, 2, or 3 substituents each independently selected from the group consisting of halogen, —CN, $C_{1-4}$ alkyl, $C_{1-4}$ alkoxy, $C_{3-6}$ cycloalkyl, $C_{1-4}$ haloalkyl, and $C_{1-4}$ haloalkoxy;

$R^8$ is selected from the group consisting of $C_{1-4}$ alkyl, $C_{3-6}$ cycloalkyl, a 4- to 7-membered heterocycloalkyl, phenyl, and a 5- to 6-membered heteroaryl, each optionally substituted with 1, 2, or 3 substituents each independently selected from the group consisting of halogen, —CN, $C_{1-4}$ alkyl, $C_{1-4}$ haloalkyl, $C_{3-6}$ cycloalkyl, $C_{1-4}$ alkoxy, and $C_{1-4}$ haloalkoxy;

$Q^1$ is a moiety of

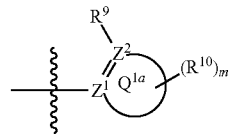

("Moiety $M^1$");

Moiety $M^1$ is

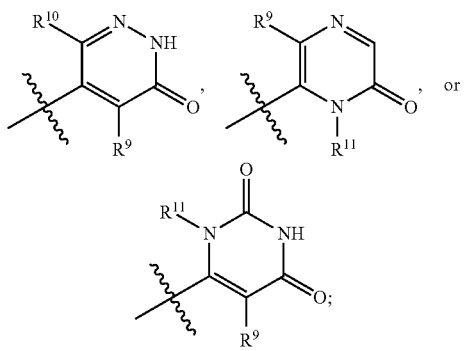

$R^9$ is $C_{1-4}$ alkyl, $C_{1-4}$ haloalkyl, $C_{3-7}$ cycloalkyl, —CN, —N($R^5$)($R^6$), $C_{1-6}$ alkoxy, $C_{1-6}$ haloalkoxy, or $C_{3-7}$ cycloalkoxy, wherein each of the $C_{1-4}$ alkyl and $C_{3-7}$ cycloalkyl is optionally substituted with 1, 2, 3, 4, or 5 substituents each independently selected from the group consisting of halogen, —N($R^5$)($R^6$), $C_{1-4}$ alkyl, $C_{1-4}$ haloalkyl, $C_{3-7}$ cycloalkyl, $C_{1-4}$ alkoxy, and $C_{1-4}$ haloalkoxy;

each $R^{10}$ is independently selected from the group consisting of halogen, —OH, —CN, —NO$_2$, oxo, thiono, $C_{1-6}$ alkyl, $C_{1-6}$ haloalkyl, $C_{1-6}$ hydroxylalkyl, $C_{1-6}$ alkoxy, $C_{1-6}$ haloalkoxy, $C_{3-7}$ cycloalkyl, $C_{2-6}$ alkenyl, $C_{2-6}$ alkynyl, $C_{6-10}$ aryl, a 4- to 10-membered heterocycloalkyl, a 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, (5- to 10-membered heteroaryl)-$C_{1-4}$ alkyl-, (5- to 10-membered heteroaryl)-$C_{2-4}$ alkenyl-, —N($R^5$)($R^6$), —N($R^7$)(C(=O)$R^8$), —S(=O)$_2$N($R^5$)($R^6$), —C(=O)—N($R^5$)($R^6$), —C(=O)—$R^8$, —C(=O)—O$R^8$, and —O$R^8$, wherein each of said $C_{1-6}$ alkyl, $C_{3-7}$ cycloalkyl, $C_{6-10}$ aryl, 4- to 10-membered heterocycloalkyl, 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, (5- to 10-membered heteroaryl)-$C_{1-4}$ alkyl-, and (5- to 10-membered heteroaryl)-$C_{2-4}$ alkenyl- is optionally substituted with 1, 2, 3 or 4 substituents each independently selected from the group consisting of halogen, OH, —CN, —NO$_2$, $C_{1-4}$ alkyl, $C_{1-4}$ hydroxyalkyl, $C_{1-4}$ alkoxy, —N($R^5$)($R^6$), —S—($C_{1-4}$ alkyl), —S(=O)$_2$—($C_{1-4}$ alkyl), $C_{6-10}$ aryloxy, ($C_{6-10}$ aryl)-$C_{1-4}$ alkyloxy- optionally substituted with 1 or 2 $C_{1-4}$ alkyl, oxo, —C(=O)H, —C(=O)—$C_{1-4}$ alkyl, —CO(=O)O—$C_{1-4}$ alkyl, —C(=O)NH$_2$, —NHC(=O)H, —NHC(=O)—($C_{1-4}$ alkyl), $C_{3-7}$ cycloalkyl, a 5- or 6-membered heteroaryl, $C_{1-4}$ haloalkyl, and $C_{1-4}$ haloalkoxy; and $R^{11}$ is H, $C_{1-4}$ alkyl, $C_{1-4}$ haloalkyl, or $C_{3-7}$ cycloalkyl.

5. The compound or pharmaceutically acceptable salt according to claim 3, wherein $R^9$ is $C_{1-4}$ alkyl or —CN; and each $R^{10}$ is independently $C_{1-4}$ alkyl.

6. A compound selected from:
4-[4-(4,6-dimethylpyrimidin-5-yl)-3-fluorophenoxy]-1H-pyrrolo[3,2-c]pyridine;
(+)-4,6-dimethyl-5-[2-methyl-4-(1H-pyrazolo[4,3-c]pyridin-4-yloxy)phenyl]pyridazin-3(2H)-one;
(−)-4,6-dimethyl-5-[2-methyl-4-(1H-pyrazolo[4,3-c]pyridin-4-yloxy)phenyl]pyridazin-3(2H)-one;
4-[4-(4,6-dimethylpyrimidin-5-yl)-3-methylphenoxy]-1H-pyrrolo[3,2-c]pyridine;
4-[4-(4,6-dimethylpyrimidin-5-yl)-3-methylphenoxy]-1H-pyrazolo[4,3-c]pyridine;
4,6-dimethyl-5-[4-(1H-pyrrolo[3,2-c]pyridin-4-yloxy)phenyl]pyridazin-3(2H)-one;
(−)-1,5-dimethyl-6-[2-methyl-4-(1H-pyrazolo[4,3-c]pyridin-4-yloxy)phenyl]pyrimidine-2,4(1H,3H)-dione;
4,6-dimethyl-5-[2-methyl-4-(1H-pyrrolo[3,2-c]pyridin-4-yloxy)phenyl]pyridazin-3(2H)-one, ENT-1;
4,6-dimethyl-5-[2-methyl-4-(1H-pyrrolo[3,2-c]pyridin-4-yloxy)phenyl]pyridazin-3(2H)-one, ENT-2;
4-[4-(4,6-dimethyl-1-oxidopyrimidin-5-yl)-3-methyl phenoxy]-1H-pyrazolo[4,3-c]pyridine;
6-methyl-5-[2-methyl-4-(1H-pyrrolo[3,2-c]pyridin-4-yloxy)phenyl]imidazo[1,2-a]pyrazine;
4-[4-(4,6-dimethylpyrimidin-5-yl)phenoxy]-1H-pyrrolo[3,2-c]pyridine;
2-(4,6-dimethylpyrimidin-5-yl)-5-(1H-pyrrolo[3,2-c]pyridin-4-yloxy)benzonitrile;
4-[3-chloro-4-(4,6-dimethylpyrimidin-5-yl)phenoxy]-1H-pyrrolo[3,2-c]pyridine;
(−)-1,5-dimethyl-6-[2-methyl-4-(1H-pyrrolo[3,2-c]pyridin-4-yloxy)phenyl]pyrazin-2(1H)-one;
4-[4-(4,6-dimethylpyrimidin-5-yl)-3-fluorophenoxy]-1H-pyrazolo[4,3-c]pyridine;
4-[4-(4,6-dimethylpyrimidin-5-yl)-3-methoxyphenoxy]-1H-pyrazolo[4,3-c]pyridine;
4-[3-chloro-4-(4,6-dimethylpyrimidin-5-yl)phenoxy]-1H-pyrazolo[4,3-c]pyridine;
(+)-1,5-dimethyl-6-[2-methyl-4-(1H-pyrazolo[4,3-c]pyridin-4-yloxy)phenyl]pyrazin-2(1H)-one;
4,6-dimethyl-5-[4-(1H-pyrazolo[4,3-c]pyridin-4-yloxy)phenyl]pyridazin-3(2H)-one; and
1,5-dimethyl-6-[4-(1H-pyrazolo[4,3-c]pyridin-4-yloxy)phenyl]pyrimidine-2,4(1H,3H)-dione, or a pharmaceutically acceptable salt thereof.

7. A pharmaceutical composition comprising the compound or pharmaceutically acceptable salt according to claim 1 and a pharmaceutically acceptable carrier.

8. A pharmaceutical composition comprising the compound or pharmaceutically acceptable salt according to claim 2 and a pharmaceutically acceptable carrier.

9. A pharmaceutical composition comprising the compound or pharmaceutically acceptable salt according to claim 3 and a pharmaceutically acceptable carrier.

10. A pharmaceutical composition comprising the compound or pharmaceutically acceptable salt according to claim 4 and a pharmaceutically acceptable carrier.

11. A pharmaceutical composition comprising the compound or pharmaceutically acceptable salt according to claim 5 and a pharmaceutically acceptable carrier.

12. A pharmaceutical composition comprising the compound or pharmaceutically acceptable salt according to claim 6 and a pharmaceutically acceptable carrier.

13. A compound that is 4-[4-(4,6-dimethylpyrimidin-5-yl)-3-fluorophenoxy]-1H-pyrrolo[3,2-c]pyridine or a pharmaceutically acceptable salt thereof.

14. The compound according to claim 13 that is 4-[4-(4,6-dimethylpyrimidin-5-yl)-3-fluorophenoxy]-1H-pyrrolo[3,2-c]pyridine.

15. The pharmaceutically acceptable salt according to claim 13 that is a pharmaceutically acceptable salt of 4-[4-(4,6-dimethylpyrimidin-5-yl)-3-fluorophenoxy]-1H-pyrrolo[3,2-c]pyridine.

16. A pharmaceutical composition comprising the compound or pharmaceutically acceptable salt according to claim 13 and a pharmaceutically acceptable carrier.

17. A pharmaceutical composition comprising the compound according to claim 14 and a pharmaceutically acceptable carrier.

18. A pharmaceutical composition comprising the pharmaceutically acceptable salt according to claim 15 and a pharmaceutically acceptable carrier.

19. A compound that is 4-[4-(4,6-dimethylpyrimidin-5-yl)-3-methylphenoxy]-1H-pyrazolo[4,3-c]pyridine or a pharmaceutically acceptable salt thereof.

20. The compound according to claim 19 that is 4-[4-(4,6-dimethylpyrimidin-5-yl)-3-methylphenoxy]-1H-pyrazolo[4,3-c]pyridine.

21. The pharmaceutically acceptable salt according to claim 19 that is a pharmaceutically acceptable salt of 4-[4-(4,6-dimethylpyrimidin-5-yl)-3-methylphenoxy]-1H-pyrazolo[4,3-c]pyridine.

22. A pharmaceutical composition comprising the compound or pharmaceutically acceptable salt according to claim 19 and a pharmaceutically acceptable carrier.

23. A pharmaceutical composition comprising the compound according to claim 20 and a pharmaceutically acceptable carrier.

24. A pharmaceutical composition comprising the pharmaceutically acceptable salt according to claim 21 and a pharmaceutically acceptable carrier.

25. A compound that is (−)-1,5-dimethyl-6-[2-methyl-4-(1H-pyrazolo[4,3-c]pyridin-4-yloxy)phenyl]pyrimidine-2,4(1H,3H)-dione or a pharmaceutically acceptable salt thereof.

26. The compound according to claim 25 that is (−)-1,5-dimethyl-6-[2-methyl-4-(1H-pyrazolo[4,3-c]pyridin-4-yloxy)phenyl]pyrimidine-2,4(1H,3H)-dione.

27. The pharmaceutically acceptable salt according to claim 25 that is a pharmaceutically acceptable salt of (−)-1,5-dimethyl-6-[2-methyl-4-(1H-pyrazolo[4,3-c]pyridin-4-yloxy)phenyl]pyrimidine-2,4(1H,3H)-dione.

28. A pharmaceutical composition comprising the compound or pharmaceutically acceptable salt according to claim 25 and a pharmaceutically acceptable carrier.

29. A pharmaceutical composition comprising the compound according to claim 26 and a pharmaceutically acceptable carrier.

30. A pharmaceutical composition comprising the pharmaceutically acceptable salt according to claim 27 and a pharmaceutically acceptable carrier.

31. A compound that is 4,6-dimethyl-5-[2-methyl-4-(1H-pyrrolo[3,2-c]pyridin-4-yloxy)phenyl]pyridazin-3(2H)-one, ENT-1 or a pharmaceutically acceptable salt thereof.

32. The compound according to claim 31 that is 4,6-dimethyl-5-[2-methyl-4-(1H-pyrrolo[3,2-c]pyridin-4-yloxy)phenyl]pyridazin-3(2H)-one, ENT-1.

33. The pharmaceutically acceptable salt according to claim 31 that is a pharmaceutically acceptable salt of 4,6-dimethyl-5-[2-methyl-4-(1H-pyrrolo[3,2-c]pyridin-4-yloxy)phenyl]pyridazin-3(2H)-one, ENT-1.

34. A pharmaceutical composition comprising the compound or pharmaceutically acceptable salt according to claim 31 and a pharmaceutically acceptable carrier.

35. A pharmaceutical composition comprising the compound according to claim 32 and a pharmaceutically acceptable carrier.

36. A pharmaceutical composition comprising the pharmaceutically acceptable salt according to claim 33 and a pharmaceutically acceptable carrier.

37. A compound that is 4,6-dimethyl-5-[2-methyl-4-(1H-pyrrolo[3,2-c]pyridin-4-yloxy)phenyl]pyridazin-3(2H)-one, ENT-2 or a pharmaceutically acceptable salt thereof.

38. The compound according to claim 31 that is 4,6-dimethyl-5-[2-methyl-4-(1H-pyrrolo[3,2-c]pyridin-4-yloxy)phenyl]pyridazin-3(2H)-one, ENT-2.

39. The pharmaceutically acceptable salt according to claim 31 that is a pharmaceutically acceptable salt of 4,6-dimethyl-5-[2-methyl-4-(1H-pyrrolo[3,2-c]pyridin-4-yloxy)phenyl]pyridazin-3(2H)-one, ENT-2.

40. A pharmaceutical composition comprising the compound or pharmaceutically acceptable salt according to claim 37 and a pharmaceutically acceptable carrier.

41. A pharmaceutical composition comprising the compound according to claim 38 and a pharmaceutically acceptable carrier.

42. A pharmaceutical composition comprising the pharmaceutically acceptable salt according to claim 39 and a pharmaceutically acceptable carrier.

43. A compound that is 2-(4,6-dimethylpyrimidin-5-yl)-5-(1H-pyrrolo[3,2-c]pyridin-4-yloxy)benzonitrile or a pharmaceutically acceptable salt thereof.

44. The compound according to claim 43 that is 2-(4,6-dimethylpyrimidin-5-yl)-5-(1H-pyrrolo[3,2-c]pyridin-4-yloxy)benzonitrile.

45. The pharmaceutically acceptable salt according to claim 43 that is a pharmaceutically acceptable salt of 2-(4,6-dimethylpyrimidin-5-yl)-5-(1H-pyrrolo[3,2-c]pyridin-4-yloxy)benzonitrile.

46. A pharmaceutical composition comprising the compound or pharmaceutically acceptable salt according to claim 43 and a pharmaceutically acceptable carrier.

47. A pharmaceutical composition comprising the compound according to claim 44 and a pharmaceutically acceptable carrier.

48. A pharmaceutical composition comprising the pharmaceutically acceptable salt according to claim 45 and a pharmaceutically acceptable carrier.

49. A compound that is (+)-1,5-dimethyl-6-[2-methyl-4-(1H-pyrazolo[4,3-c]pyridin-4-yloxy)phenyl]pyrazin-2(1H)-one or a pharmaceutically acceptable salt thereof.

50. The compound according to claim 43 that is (+)-1,5-dimethyl-6-[2-methyl-4-(1H-pyrazolo[4,3-c]pyridin-4-yloxy)phenyl]pyrazin-2(1H)-one.

51. The pharmaceutically acceptable salt according to claim 43 that is a pharmaceutically acceptable salt of (+)-1,5-dimethyl-6-[2-methyl-4-(1H-pyrazolo[4,3-c]pyridin-4-yloxy)phenyl]pyrazin-2(1H)-one.

52. A pharmaceutical composition comprising the compound or pharmaceutically acceptable salt according to claim 49 and a pharmaceutically acceptable carrier.

53. A pharmaceutical composition comprising the compound according to claim 50 and a pharmaceutically acceptable carrier.

54. A pharmaceutical composition comprising the pharmaceutically acceptable salt according to claim 51 and a pharmaceutically acceptable carrier.

* * * * *